(12) United States Patent
Fangrow

(10) Patent No.: US 11,517,733 B2
(45) Date of Patent: Dec. 6, 2022

(54) MEDICAL FLUID CONNECTORS AND METHODS FOR PROVIDING ADDITIVES IN MEDICAL FLUID LINES

(71) Applicant: ICU Medical, Inc., San Clemente, CA (US)

(72) Inventor: Thomas F. Fangrow, Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 318 days.

(21) Appl. No.: 16/669,303

(22) Filed: Oct. 30, 2019

(65) Prior Publication Data

US 2020/0069931 A1    Mar. 5, 2020

Related U.S. Application Data

(63) Continuation of application No. PCT/US2018/030015, filed on Apr. 27, 2018.

(60) Provisional application No. 62/662,149, filed on Apr. 24, 2018, provisional application No. 62/558,618, filed on Sep. 14, 2017, provisional application No.
(Continued)

(51) Int. Cl.
*A61M 39/16* (2006.01)
*A61M 5/14* (2006.01)

(52) U.S. Cl.
CPC ........ *A61M 39/162* (2013.01); *A61M 5/1409* (2013.01)

(58) Field of Classification Search
CPC .. A61M 39/162; A61M 5/1409; A61M 39/10; A61M 5/1408
See application file for complete search history.

(56) References Cited

U.S. PATENT DOCUMENTS

| | | |
|---|---|---|
| 382,297 A | 5/1888 | Fry |
| 559,697 A | 5/1896 | Tiugti et al. |
| 877,946 A | 2/1908 | Overton |

(Continued)

FOREIGN PATENT DOCUMENTS

| | | |
|---|---|---|
| CA | 2 148 847 | 12/1995 |
| CA | 2825217 | 3/2007 |

(Continued)

OTHER PUBLICATIONS

Invitation to Pay Additional Search Fees in corresponding International Patent Application No. PCT/US2018/030015, dated Jun. 19, 2018, in 2 pages.

(Continued)

*Primary Examiner* — Bradley J Osinski
(74) *Attorney, Agent, or Firm* — Knobbe, Martens, Olson & Bear, LLP

(57) ABSTRACT

Disclosed is a medical fluid connector configured to receive and dispense medical liquid. The medical connector can be structured to include an initial stage in which medical liquid is infused into the connector and dispensed out of the connector essentially unchanged. The medical connector also can be structured to include a subsequent stage in which medical liquid is not infused into the connector and a volume of therapeutic liquid is dispensed out of the connector. The therapeutic liquid can include a portion of the volume of the medical liquid that was infused into the connector in the initial stage plus a therapeutic additive.

20 Claims, 24 Drawing Sheets

Related U.S. Application Data

62/520,300, filed on Jun. 15, 2017, provisional application No. 62/492,887, filed on May 1, 2017.

(56) References Cited

U.S. PATENT DOCUMENTS

| | | |
|---|---|---|
| 975,939 A | 11/1910 | William et al. |
| 1,445,642 A | 2/1923 | O'Neill |
| 1,793,068 A | 2/1931 | Dickinson |
| 2,098,340 A | 11/1937 | Henahan |
| 2,436,297 A | 2/1948 | Guarnaschelli |
| 2,457,052 A | 12/1948 | Le Clair |
| 2,771,644 A | 11/1956 | Martin |
| 2,842,382 A | 7/1958 | Franck |
| 2,968,497 A | 1/1961 | Treleman |
| 3,127,892 A | 4/1964 | Bellamy, Jr. et al. |
| 3,262,448 A | 7/1966 | Ring et al. |
| 3,270,743 A | 9/1966 | Gingras |
| 3,301,392 A | 1/1967 | Eddingfield |
| 3,304,047 A | 2/1967 | Martin |
| 3,334,860 A | 8/1967 | Bolton, Jr. |
| 3,411,665 A | 11/1968 | Blum |
| 3,484,121 A | 12/1969 | Quinton |
| 3,485,416 A | 12/1969 | Fohrman |
| 3,538,950 A | 11/1970 | Porteners |
| 3,595,241 A | 7/1971 | Sheridan |
| 3,604,582 A | 9/1971 | Boudin |
| 3,707,972 A | 1/1973 | Villari et al. |
| 3,729,031 A | 4/1973 | Baldwin |
| 3,882,858 A | 5/1975 | Klemm |
| 3,977,401 A | 8/1976 | Pike |
| 3,977,517 A | 8/1976 | Kadlecik et al. |
| 3,987,930 A | 10/1976 | Fuson |
| 3,993,066 A | 11/1976 | Virag |
| 4,041,934 A | 8/1977 | Genese |
| 4,046,889 A | 9/1977 | Ondetti et al. |
| 4,052,511 A | 10/1977 | Cushman et al. |
| 4,053,052 A | 10/1977 | Jasper |
| 4,053,651 A | 10/1977 | Ondetti et al. |
| 4,066,067 A | 1/1978 | Micheli |
| 4,076,285 A | 2/1978 | Martinez |
| 4,078,686 A | 3/1978 | Karesh et al. |
| 4,079,738 A | 3/1978 | Dunn et al. |
| 4,095,810 A | 6/1978 | Kulle |
| 4,113,751 A | 9/1978 | Arnold |
| 4,121,585 A | 10/1978 | Becker, Jr. |
| 4,129,571 A | 12/1978 | Ondetti et al. |
| 4,133,441 A | 1/1979 | Mittleman et al. |
| 4,143,853 A | 3/1979 | Abramson |
| 4,150,845 A | 4/1979 | Kopacz et al. |
| 4,154,840 A | 5/1979 | Ondetti et al. |
| 4,154,960 A | 5/1979 | Ondetti et al. |
| 4,192,443 A | 3/1980 | McLaren |
| 4,194,509 A | 3/1980 | Pickering et al. |
| 4,195,632 A | 4/1980 | Parker et al. |
| 4,233,982 A | 11/1980 | Bauer et al. |
| 4,243,035 A | 1/1981 | Barrett |
| 4,245,635 A | 1/1981 | Kontos |
| 4,264,664 A | 4/1981 | Kunz |
| 4,280,632 A | 7/1981 | Yuhara |
| 4,294,370 A | 10/1981 | Toeppen |
| 4,317,446 A | 3/1982 | Ambrosio et al. |
| 4,324,239 A | 4/1982 | Gordon et al. |
| 4,325,368 A | 4/1982 | Kaemmerer |
| 4,331,783 A | 5/1982 | Stoy |
| 4,334,551 A | 6/1982 | Pfister |
| 4,335,756 A | 6/1982 | Sharp et al. |
| 4,337,327 A | 6/1982 | Stoy |
| 4,340,049 A | 7/1982 | Munsch |
| 4,340,052 A | 7/1982 | Dennehey et al. |
| 4,354,490 A | 10/1982 | Rogers |
| 4,369,294 A | 1/1983 | Stoy |
| 4,370,451 A | 1/1983 | Stoy |
| 4,379,458 A | 4/1983 | Bauer et al. |
| 4,379,874 A | 4/1983 | Stoy |
| 4,384,589 A | 5/1983 | Morris |
| 4,387,879 A | 6/1983 | Tauschinski |
| 4,390,016 A | 6/1983 | Riess |
| 4,397,442 A | 8/1983 | Larkin |
| 4,402,691 A | 9/1983 | Rosenthal et al. |
| 4,405,312 A | 9/1983 | Gross et al. |
| 4,417,890 A | 11/1983 | Dennehey et al. |
| 4,420,589 A | 12/1983 | Stoy |
| 4,427,126 A | 1/1984 | Ostrowsky |
| 4,430,073 A | 2/1984 | Bemis et al. |
| 4,432,764 A | 2/1984 | Lopez |
| 4,432,766 A | 2/1984 | Bellotti et al. |
| 4,436,125 A | 3/1984 | Blenkush |
| 4,439,179 A | 3/1984 | Lueders et al. |
| 4,439,184 A | 3/1984 | Wheeler |
| 4,440,207 A | 4/1984 | Genatempo et al. |
| 4,444,310 A | 4/1984 | Odell |
| 4,446,967 A | 5/1984 | Halkyard |
| 4,447,419 A | 5/1984 | Quadro |
| 4,457,749 A | 7/1984 | Bellotti et al. |
| 4,461,368 A | 7/1984 | Plourde |
| 4,461,896 A | 7/1984 | Portlock |
| 4,480,940 A | 11/1984 | Woodruff |
| 4,507,111 A | 3/1985 | Gordon et al. |
| 4,511,359 A | 4/1985 | Vaillancourt |
| 4,534,764 A | 8/1985 | Mittleman et al. |
| 4,538,836 A | 9/1985 | Kruetten |
| 4,559,043 A | 12/1985 | Whitehouse |
| 4,568,675 A | 2/1986 | Bush et al. |
| 4,585,758 A | 4/1986 | Huang et al. |
| 4,602,042 A | 7/1986 | Chantler et al. |
| 4,610,469 A | 9/1986 | Wolff-Mooij |
| 4,619,640 A | 10/1986 | Potolsky et al. |
| 4,623,332 A | 11/1986 | Lindmayer et al. |
| 4,624,664 A | 11/1986 | Peluso et al. |
| 4,626,545 A | 12/1986 | Taub |
| 4,629,159 A | 12/1986 | Wellenstam |
| 4,631,188 A | 12/1986 | Stoy |
| 4,642,091 A | 2/1987 | Richmond |
| 4,660,803 A | 4/1987 | Johnston et al. |
| 4,662,878 A | 5/1987 | Lindmayer |
| 4,666,057 A | 5/1987 | Come et al. |
| 4,666,427 A | 5/1987 | Larsson et al. |
| 4,671,306 A | 6/1987 | Spector |
| 4,671,412 A | 6/1987 | Gatten |
| 4,681,886 A | 7/1987 | Haugwitz et al. |
| 4,692,458 A | 9/1987 | Ryan et al. |
| 4,692,459 A | 9/1987 | Ryan et al. |
| 4,700,744 A | 10/1987 | Rutter et al. |
| 4,703,762 A | 11/1987 | Rathbone et al. |
| 4,705,790 A | 11/1987 | Hubele et al. |
| 4,723,603 A | 2/1988 | Plummer |
| 4,728,075 A | 3/1988 | Paradis |
| 4,728,321 A | 3/1988 | Chen |
| 4,738,668 A | 4/1988 | Bellotti et al. |
| 4,745,950 A | 5/1988 | Mathieu |
| 4,747,502 A | 5/1988 | Luenser |
| 4,748,160 A | 5/1988 | Bennion et al. |
| 4,752,983 A | 6/1988 | Grieshaber |
| 4,769,013 A | 9/1988 | Lorenz et al. |
| 4,774,964 A | 10/1988 | Bonaldo |
| 4,774,965 A | 10/1988 | Rodriguez et al. |
| 4,778,447 A | 10/1988 | Velde et al. |
| 4,781,702 A | 11/1988 | Herrli |
| 4,799,926 A | 1/1989 | Haber |
| 4,804,015 A | 2/1989 | Albinsson |
| 4,808,158 A | 2/1989 | Kreuzer et al. |
| 4,810,241 A | 3/1989 | Rogers |
| 4,811,847 A | 3/1989 | Reif et al. |
| 4,813,933 A | 3/1989 | Turner |
| 4,816,024 A | 3/1989 | Sitar et al. |
| 4,834,271 A | 5/1989 | Litwin |
| 4,862,913 A | 9/1989 | Wildfang |
| 4,874,366 A * | 10/1989 | Zdeb .......... A61M 5/1409 604/518 |
| 4,883,483 A | 11/1989 | Lindmayer |
| 4,889,255 A | 12/1989 | Schiemann et al. |
| 4,894,056 A | 1/1990 | Bommarito |
| 4,898,580 A | 2/1990 | Crowley |
| 4,915,687 A | 4/1990 | Sivert |

(56) References Cited

U.S. PATENT DOCUMENTS

| | | |
|---|---|---|
| 4,917,669 A | 4/1990 | Bonaldo |
| 4,919,658 A | 4/1990 | Badia |
| 4,927,019 A | 5/1990 | Haber et al. |
| 4,935,010 A | 6/1990 | Cox et al. |
| 4,941,873 A | 7/1990 | Fischer |
| 4,950,260 A | 8/1990 | Bonaldo |
| 4,957,637 A | 9/1990 | Cornell |
| 4,963,132 A | 10/1990 | Gibson |
| D313,277 S | 12/1990 | Haining |
| D314,050 S | 1/1991 | Sone |
| 4,983,161 A | 1/1991 | Dadson et al. |
| 4,985,017 A | 1/1991 | Theeuwes |
| 4,989,733 A | 2/1991 | Patry |
| 4,991,629 A | 2/1991 | Ernesto et al. |
| 4,997,371 A | 3/1991 | Fischer |
| 4,999,210 A * | 3/1991 | Solomon ............... A61L 29/06 427/2.25 |
| 5,002,964 A | 3/1991 | Loscalzo |
| 5,006,114 A | 4/1991 | Rogers et al. |
| 5,015,238 A | 5/1991 | Solomon et al. |
| 5,019,096 A | 5/1991 | Fox, Jr. et al. |
| 5,021,059 A | 6/1991 | Kensey et al. |
| 5,024,657 A | 6/1991 | Needham et al. |
| 5,025,001 A | 6/1991 | Loscalzo et al. |
| 5,026,359 A | 6/1991 | Burroughs |
| 5,031,622 A | 7/1991 | LaHaye |
| 5,033,961 A | 7/1991 | Kandler et al. |
| 5,047,021 A | 9/1991 | Utterberg |
| 5,049,139 A | 9/1991 | Gilchrist |
| 5,059,186 A | 10/1991 | Yamamoto et al. |
| 5,065,783 A | 11/1991 | Ogle, II |
| 5,070,885 A | 12/1991 | Bonaldo |
| 5,071,411 A | 12/1991 | Hillstead |
| 5,071,413 A | 12/1991 | Utterberg |
| 5,098,385 A | 3/1992 | Walsh |
| 5,108,376 A | 4/1992 | Bonaldo |
| 5,122,123 A | 6/1992 | Vaillancourt |
| 5,127,626 A | 7/1992 | Hilal et al. |
| 5,129,824 A | 7/1992 | Keller |
| 5,139,483 A | 8/1992 | Ryan |
| 5,143,104 A | 9/1992 | Iba et al. |
| 5,147,333 A | 9/1992 | Raines |
| 5,154,703 A | 10/1992 | Bonaldo |
| 5,154,920 A | 10/1992 | Flesher et al. |
| 5,184,742 A | 2/1993 | DeCaprio et al. |
| 5,190,534 A | 3/1993 | Kendell |
| 5,195,957 A | 3/1993 | Tollini |
| RE34,223 E | 4/1993 | Bonaldo |
| 5,199,948 A | 4/1993 | McPhee |
| 5,201,725 A | 4/1993 | Kling |
| 5,203,775 A | 4/1993 | Frank et al. |
| 5,205,820 A | 4/1993 | Kriesel |
| 5,205,821 A | 4/1993 | Kruger et al. |
| 5,207,706 A | 5/1993 | Menaker |
| 5,211,634 A | 5/1993 | Vaillancourt |
| 5,212,204 A | 5/1993 | Keefer et al. |
| 5,215,537 A | 6/1993 | Lynn et al. |
| 5,240,675 A | 8/1993 | Wilk et al. |
| 5,242,421 A | 9/1993 | Chan |
| 5,246,011 A | 9/1993 | Caillouette |
| 5,250,550 A | 10/1993 | Keefer et al. |
| 5,251,873 A | 10/1993 | Atkinson et al. |
| D342,134 S | 12/1993 | Mongeon |
| 5,269,771 A | 12/1993 | Thomas et al. |
| 5,278,192 A | 1/1994 | Fung et al. |
| 5,281,206 A | 1/1994 | Lopez |
| 5,284,475 A | 2/1994 | Mackal |
| 5,295,657 A | 3/1994 | Atkinson |
| 5,297,310 A | 3/1994 | Cox et al. |
| 5,301,686 A | 4/1994 | Newman |
| 5,304,130 A | 4/1994 | Button |
| 5,306,243 A | 4/1994 | Bonaldo |
| 5,312,377 A | 5/1994 | Dalton |
| 5,324,270 A | 6/1994 | Kayan et al. |
| 5,324,647 A | 6/1994 | Rubens et al. |
| 5,330,426 A | 7/1994 | Kriesel et al. |
| 5,330,450 A | 7/1994 | Lopez |
| 5,330,899 A | 7/1994 | Devaughn et al. |
| 5,337,730 A | 8/1994 | Maguire |
| 5,344,414 A | 9/1994 | Lopez et al. |
| 5,352,410 A | 10/1994 | Hansen et al. |
| 5,354,267 A | 10/1994 | Niermann et al. |
| 5,356,396 A | 10/1994 | Wyatt et al. |
| 5,360,413 A | 11/1994 | Leason et al. |
| 5,366,505 A | 11/1994 | Farber |
| 5,366,997 A | 11/1994 | Keefer et al. |
| 5,370,614 A | 12/1994 | Amundson et al. |
| 5,370,636 A | 12/1994 | Von Witzleben |
| 5,370,640 A | 12/1994 | Kolff |
| 5,375,589 A | 12/1994 | Bhatta |
| 5,380,306 A | 1/1995 | Brinon |
| 5,380,758 A | 1/1995 | Stamler et al. |
| 5,391,150 A | 2/1995 | Richmond |
| 5,402,826 A | 4/1995 | Molnar et al. |
| 5,405,331 A | 4/1995 | Behnke et al. |
| 5,405,333 A | 4/1995 | Richmond |
| 5,405,919 A | 4/1995 | Keefer et al. |
| 5,407,807 A | 4/1995 | Markus |
| 5,409,012 A | 4/1995 | Sahatjian |
| 5,411,499 A | 5/1995 | Dudar et al. |
| 5,417,673 A | 5/1995 | Gordon |
| 5,425,465 A | 6/1995 | Healy |
| 5,428,070 A | 6/1995 | Cooke et al. |
| 5,433,330 A | 7/1995 | Yatsko et al. |
| 5,433,705 A | 7/1995 | Giebel et al. |
| 5,439,451 A | 8/1995 | Collinson et al. |
| 5,441,487 A | 8/1995 | Vedder |
| 5,445,623 A | 8/1995 | Richmond |
| 5,456,668 A | 10/1995 | Ogle, II |
| 5,456,675 A | 10/1995 | Wolbring et al. |
| 5,464,399 A | 11/1995 | Boettger |
| 5,470,307 A | 11/1995 | Lindall |
| 5,470,327 A | 11/1995 | Helgren et al. |
| 5,471,706 A | 12/1995 | Wallock et al. |
| 5,474,536 A | 12/1995 | Bonaldo |
| 5,480,393 A | 1/1996 | Bommarito |
| 5,492,147 A | 2/1996 | Challender et al. |
| 5,496,288 A | 3/1996 | Sweeney |
| 5,501,426 A | 3/1996 | Atkinson et al. |
| 5,507,733 A | 4/1996 | Larkin et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,485,827 A | 6/1996 | Zapol et al. |
| 5,525,357 A | 6/1996 | Keefer et al. |
| 5,531,695 A | 7/1996 | Swisher |
| 5,533,708 A | 7/1996 | Atkinson et al. |
| 5,533,983 A | 7/1996 | Haining |
| 5,535,785 A | 7/1996 | Werge et al. |
| 5,536,241 A | 7/1996 | Zapol |
| 5,536,258 A | 7/1996 | Folden |
| 5,540,661 A | 7/1996 | Tomisaka et al. |
| 5,545,614 A | 8/1996 | Stamler et al. |
| 5,549,566 A | 8/1996 | Elias et al. |
| 5,549,651 A | 8/1996 | Lynn |
| 5,552,115 A | 9/1996 | Malchesky |
| 5,552,118 A | 9/1996 | Mayer |
| 5,554,127 A | 9/1996 | Crouther et al. |
| 5,554,135 A | 9/1996 | Menyhay |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,580,530 A | 12/1996 | Kowatsch et al. |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,599,352 A | 2/1997 | Dinh et al. |
| 5,605,696 A | 2/1997 | Eury et al. |
| 5,607,072 A | 3/1997 | Rigney et al. |

(56) References Cited

U.S. PATENT DOCUMENTS

| | | |
|---|---|---|
| 5,613,615 A | 3/1997 | Zeyfang et al. |
| 5,616,130 A | 4/1997 | Mayer |
| 5,620,088 A | 4/1997 | Martin et al. |
| 5,620,427 A | 4/1997 | Werschmidt et al. |
| 5,624,402 A | 4/1997 | Imbert |
| 5,628,733 A | 5/1997 | Zinreich et al. |
| RE35,539 E | 6/1997 | Bonaldo |
| 5,645,538 A | 7/1997 | Richmond |
| 5,665,077 A | 9/1997 | Resen et al. |
| 5,674,206 A | 10/1997 | Allton et al. |
| 5,676,346 A | 10/1997 | Leinsing |
| 5,685,866 A | 11/1997 | Lopez |
| 5,685,868 A | 11/1997 | Lundquist |
| 5,688,253 A | 11/1997 | Lundquist |
| 5,694,978 A | 12/1997 | Heilmann et al. |
| 5,699,821 A | 12/1997 | Paradis |
| 5,700,248 A | 12/1997 | Lopez |
| 5,702,017 A | 12/1997 | Goncalves |
| 5,716,339 A | 2/1998 | Tanaka et al. |
| 5,722,537 A | 3/1998 | Sigler |
| 5,735,826 A | 4/1998 | Richmond |
| 5,738,144 A | 4/1998 | Rogers |
| 5,743,892 A | 4/1998 | Loh et al. |
| 5,749,861 A | 5/1998 | Guala et al. |
| 5,763,409 A | 6/1998 | Bayol et al. |
| 5,770,645 A | 6/1998 | Stamler et al. |
| 5,776,116 A | 7/1998 | Lopez |
| 5,782,808 A | 7/1998 | Folden |
| 5,782,816 A | 7/1998 | Werschmidt et al. |
| 5,785,693 A | 7/1998 | Haining |
| 5,792,120 A | 8/1998 | Menyhay |
| 5,797,887 A | 8/1998 | Rosen et al. |
| 5,806,831 A | 9/1998 | Paradis |
| 5,810,792 A | 9/1998 | Fangrow, Jr. et al. |
| 5,814,024 A | 9/1998 | Thompson et al. |
| 5,814,666 A | 9/1998 | Green et al. |
| 5,820,601 A | 10/1998 | Mayer |
| 5,820,604 A | 10/1998 | Fox et al. |
| 5,827,244 A | 10/1998 | Boettger |
| 5,839,715 A | 11/1998 | Leinsing |
| 5,848,994 A | 12/1998 | Richmond |
| 5,902,631 A | 5/1999 | Wang et al. |
| 5,941,857 A | 8/1999 | Nguyen et al. |
| 5,947,954 A | 9/1999 | Bonaldo |
| 5,951,519 A | 9/1999 | Utterberg |
| 5,954,957 A | 9/1999 | Chin-Loy et al. |
| 5,971,972 A | 10/1999 | Rosenbaum |
| D416,086 S | 11/1999 | Parris et al. |
| 5,989,229 A | 11/1999 | Chiappetta |
| 5,994,444 A | 11/1999 | Trescony |
| 6,029,946 A | 2/2000 | Doyle |
| 6,036,171 A | 3/2000 | Weinheimer et al. |
| 6,041,805 A | 3/2000 | Gydesen et al. |
| 6,045,539 A | 4/2000 | Menyhay |
| 6,045,623 A | 4/2000 | Cannon |
| 6,050,978 A | 4/2000 | Orr et al. |
| 6,059,107 A | 5/2000 | Nosted et al. |
| 6,063,062 A | 5/2000 | Paradis |
| 6,068,011 A | 5/2000 | Paradis |
| 6,068,475 A | 5/2000 | Stoyka, Jr. et al. |
| 6,068,617 A | 5/2000 | Richmond |
| 6,071,413 A | 6/2000 | Dyke |
| 6,079,432 A | 6/2000 | Paradis |
| 6,087,479 A | 7/2000 | Stamler et al. |
| 6,093,743 A | 7/2000 | Lai et al. |
| 6,095,356 A | 8/2000 | Rits |
| 6,099,519 A | 8/2000 | Olsen et al. |
| 6,105,812 A | 8/2000 | Riordan |
| 6,106,502 A | 8/2000 | Richmond |
| 6,113,068 A | 9/2000 | Ryan |
| 6,113,572 A | 9/2000 | Gailey et al. |
| 6,116,468 A | 9/2000 | Nilson |
| 6,117,114 A | 9/2000 | Paradis |
| 6,126,640 A | 10/2000 | Tucker et al. |
| 6,142,446 A | 11/2000 | Leinsing |
| 6,143,318 A | 11/2000 | Gilchrist et al. |
| 6,146,363 A | 11/2000 | Giebel et al. |
| 6,152,913 A | 11/2000 | Feith et al. |
| 6,158,614 A | 12/2000 | Haines et al. |
| 6,170,522 B1 | 1/2001 | Tanida |
| 6,171,287 B1 | 1/2001 | Lynn et al. |
| 6,174,539 B1 | 1/2001 | Stamler et al. |
| 6,179,141 B1 | 1/2001 | Nakamura |
| 6,183,450 B1 | 2/2001 | Lois |
| 6,202,870 B1 | 3/2001 | Pearce |
| 6,202,901 B1 | 3/2001 | Gerber et al. |
| 6,206,134 B1 | 3/2001 | Stark et al. |
| 6,206,860 B1 | 3/2001 | Richmond |
| 6,207,855 B1 | 3/2001 | Toone et al. |
| 6,217,564 B1 | 4/2001 | Peters et al. |
| 6,227,391 B1 | 5/2001 | King |
| 6,232,406 B1 | 5/2001 | Stoy |
| 6,232,434 B1 | 5/2001 | Stamler et al. |
| 6,237,800 B1 | 5/2001 | Barrett et al. |
| 6,242,393 B1 | 6/2001 | Ishida et al. |
| 6,245,048 B1 | 6/2001 | Fangrow et al. |
| 6,245,056 B1 | 6/2001 | Walker et al. |
| 6,248,380 B1 | 6/2001 | Kocher et al. |
| 6,250,315 B1 | 6/2001 | Ernster |
| 6,255,277 B1 | 7/2001 | Stamler et al. |
| 6,267,754 B1 | 7/2001 | Peters |
| 6,299,132 B1 | 10/2001 | Weinheimer et al. |
| 6,315,113 B1 | 11/2001 | Britton et al. |
| 6,315,761 B1 | 11/2001 | Shcherbina et al. |
| 6,359,167 B2 | 3/2002 | Toone et al. |
| 6,359,182 B1 | 3/2002 | Stamler et al. |
| 6,375,231 B1 | 4/2002 | Picha et al. |
| 6,379,660 B1 | 4/2002 | Saavedra et al. |
| 6,379,691 B1 | 4/2002 | Tedeschi et al. |
| 6,394,983 B1 | 5/2002 | Mayoral et al. |
| 6,402,207 B1 | 6/2002 | Segal et al. |
| 6,403,759 B2 | 6/2002 | Stamler et al. |
| 6,409,716 B1 | 6/2002 | Sahatjian et al. |
| 6,428,520 B1 | 8/2002 | Lopez |
| 6,431,219 B1 | 8/2002 | Redler et al. |
| 6,444,318 B1 | 9/2002 | Guire et al. |
| 6,468,259 B1 | 10/2002 | Djokic et al. |
| 6,471,978 B1 | 10/2002 | Stamler et al. |
| 6,488,951 B2 | 12/2002 | Toone et al. |
| 6,491,965 B1 | 12/2002 | Berry et al. |
| 6,499,719 B1 | 12/2002 | Clancy et al. |
| 6,508,792 B2 | 1/2003 | Szames et al. |
| 6,508,807 B1 | 1/2003 | Peters |
| 6,538,116 B2 | 3/2003 | Stamler et al. |
| 6,541,802 B2 | 4/2003 | Doyle |
| 6,543,745 B1 | 4/2003 | Enerson |
| 6,550,493 B2 | 4/2003 | Williamson et al. |
| 6,555,504 B1 | 4/2003 | Ayai et al. |
| 6,562,781 B1 | 5/2003 | Berry et al. |
| 6,581,906 B2 | 6/2003 | Pott et al. |
| 6,583,311 B2 | 6/2003 | Toone et al. |
| 6,585,691 B1 | 7/2003 | Vitello |
| 6,595,964 B2 | 7/2003 | Finley et al. |
| 6,595,981 B2 | 7/2003 | Huet |
| 6,605,294 B2 | 8/2003 | Sawhney |
| 6,605,751 B1 | 8/2003 | Gibbins et al. |
| 6,609,696 B2 | 8/2003 | Enerson |
| 6,632,199 B1 | 10/2003 | Tucker et al. |
| 6,634,498 B2 | 10/2003 | Kayerod et al. |
| 6,656,217 B1 | 12/2003 | Herzog, Jr. et al. |
| 6,666,852 B2 | 12/2003 | Niedospial, Jr. |
| 6,673,891 B2 | 1/2004 | Stamler et al. |
| 6,679,395 B1 | 1/2004 | Pfefferkorn et al. |
| 6,679,870 B1 | 1/2004 | Finch et al. |
| 6,681,803 B2 | 1/2004 | Taneya et al. |
| 6,685,694 B2 | 2/2004 | Finch et al. |
| 6,692,468 B1 | 2/2004 | Waldenburg |
| 6,695,817 B1 | 2/2004 | Fangrow |
| 6,716,396 B1 | 4/2004 | Anderson |
| 6,722,705 B2 | 4/2004 | Korkor |
| 6,725,492 B2 | 4/2004 | Moore et al. |
| 6,745,998 B2 | 6/2004 | Doyle |
| 6,786,884 B1 | 9/2004 | DeCant, Jr. et al. |
| 6,808,510 B1 | 10/2004 | DiFiore |

(56) References Cited

U.S. PATENT DOCUMENTS

| | | |
|---|---|---|
| 6,827,766 B2 | 12/2004 | Carnes et al. |
| 6,840,501 B2 | 1/2005 | Doyle |
| 6,871,087 B1 | 3/2005 | Hughes et al. |
| 6,875,205 B2 | 4/2005 | Leinsing |
| 6,875,840 B2 | 4/2005 | Stamler et al. |
| 6,887,994 B2 | 5/2005 | Stamler et al. |
| 6,899,315 B2 | 5/2005 | Mailville et al. |
| 6,911,025 B2 | 6/2005 | Miyahar |
| 6,916,051 B2 | 7/2005 | Fisher |
| 6,929,005 B2 | 8/2005 | Sullivan et al. |
| 6,943,035 B1 | 9/2005 | Davies et al. |
| 6,955,669 B2 | 10/2005 | Curutcharry |
| 6,964,406 B2 | 11/2005 | Doyle |
| 7,004,934 B2 | 2/2006 | Vaillancourt |
| 7,015,347 B2 | 3/2006 | Toone et al. |
| 7,030,238 B2 | 4/2006 | Stamler et al. |
| 7,037,302 B2 | 5/2006 | Vaillancourt |
| 7,040,598 B2 | 5/2006 | Raybuck |
| 7,044,441 B2 | 5/2006 | Doyle |
| 7,045,585 B2 | 5/2006 | Berry et al. |
| 7,049,308 B2 | 5/2006 | Stamler et al. |
| 7,052,711 B2 | 5/2006 | West et al. |
| 7,056,308 B2 | 6/2006 | Utterberg |
| 7,067,659 B2 | 6/2006 | Stamler et al. |
| 7,081,109 B2 | 7/2006 | Tighe et al. |
| 7,083,605 B2 | 8/2006 | Miyahara |
| 7,087,709 B2 | 8/2006 | Stamler et al. |
| 7,097,850 B2 | 8/2006 | Chappa et al. |
| 7,100,891 B2 | 9/2006 | Doyle |
| 7,125,396 B2 | 10/2006 | Leinsing et al. |
| 7,140,592 B2 | 11/2006 | Phillips |
| 7,147,625 B2 | 12/2006 | Sarangapani et al. |
| 7,160,272 B1 | 1/2007 | Eyal et al. |
| 7,182,313 B2 | 2/2007 | Doyle |
| 7,195,615 B2 | 3/2007 | Tan |
| 7,198,611 B2 | 4/2007 | Connell et al. |
| 7,244,249 B2 | 7/2007 | Leinsing et al. |
| 7,259,250 B2 | 8/2007 | Stamler et al. |
| 7,279,176 B1 | 10/2007 | West et al. |
| 7,282,186 B2 | 10/2007 | Lake, Jr. et al. |
| 7,306,197 B2 | 12/2007 | Parrino et al. |
| 7,306,198 B2 | 12/2007 | Doyle |
| 7,306,566 B2 | 12/2007 | Raybuck |
| 7,309,326 B2 | 12/2007 | Fangrow, Jr. |
| 7,316,669 B2 | 1/2008 | Ranalletta |
| 7,347,458 B2 | 3/2008 | Rome et al. |
| 7,347,853 B2 | 3/2008 | DiFiore et al. |
| 7,350,764 B2 | 4/2008 | Raybuck |
| 7,361,164 B2 | 4/2008 | Simpson et al. |
| 7,417,109 B2 | 8/2008 | Stamler et al. |
| 7,431,712 B2 | 10/2008 | Kim |
| 7,442,402 B2 | 10/2008 | Chudzik et al. |
| 7,452,349 B2 | 11/2008 | Miyahar |
| 7,485,107 B2 | 2/2009 | DiFiore et al. |
| 7,491,192 B2 | 2/2009 | DiFiore |
| 7,497,484 B2 | 3/2009 | Ziman |
| 7,516,846 B2 | 4/2009 | Hansen |
| 7,588,563 B2 | 9/2009 | Guala |
| 7,611,505 B2 | 11/2009 | Ranalletta et al. |
| 7,614,426 B2 | 11/2009 | Kitani et al. |
| 7,615,034 B2 | 11/2009 | DiFiore |
| 7,625,907 B2 | 12/2009 | Stamler et al. |
| 7,635,344 B2 | 12/2009 | Tennican et al. |
| D607,325 S | 1/2010 | Rogers et al. |
| 7,645,274 B2 | 1/2010 | Whitley |
| 7,651,481 B2 | 1/2010 | Raybuck |
| 7,666,170 B2 | 2/2010 | Guala |
| 7,708,714 B2 | 5/2010 | Connell et al. |
| 7,731,678 B2 | 6/2010 | Tennican et al. |
| 7,731,679 B2 | 6/2010 | Tennican et al. |
| 7,749,189 B2 | 7/2010 | Tennican et al. |
| 7,753,891 B2 | 7/2010 | Tennican et al. |
| 7,758,530 B2 | 7/2010 | DiFiore et al. |
| 7,758,566 B2 | 7/2010 | Simpson et al. |
| 7,762,524 B2 | 7/2010 | Cawthon et al. |
| 7,763,006 B2 | 7/2010 | Tennican |
| 7,766,182 B2 | 8/2010 | Trent et al. |
| 7,766,897 B2 | 8/2010 | Ramsey et al. |
| 7,776,011 B2 | 8/2010 | Tennican et al. |
| 7,780,794 B2 | 8/2010 | Rogers et al. |
| 7,785,616 B2 | 8/2010 | Stamler et al. |
| 7,794,675 B2 | 9/2010 | Lynn |
| 7,799,010 B2 | 9/2010 | Tennican |
| 7,803,139 B2 | 9/2010 | Fangrow, Jr. |
| 7,803,140 B2 | 9/2010 | Fangrow, Jr. |
| 7,815,614 B2 | 10/2010 | Fangrow, Jr. |
| 7,857,793 B2 | 12/2010 | Raulerson et al. |
| 7,922,701 B2 | 4/2011 | Buchman |
| 7,922,711 B2 | 4/2011 | Ranalletta et al. |
| 7,928,079 B2 | 4/2011 | Hrabie et al. |
| 7,938,795 B2 | 5/2011 | DiFiore et al. |
| 7,956,062 B2 | 6/2011 | Stamler et al. |
| 7,959,026 B2 | 6/2011 | Bertani |
| 7,963,565 B2 | 6/2011 | Suter |
| 7,972,137 B2 | 7/2011 | Rosen |
| 7,972,322 B2 | 7/2011 | Tennican |
| 7,981,090 B2 | 7/2011 | Plishka et al. |
| 7,985,302 B2 | 7/2011 | Rogers et al. |
| 7,993,309 B2 | 8/2011 | Schweikert |
| 7,998,134 B2 | 8/2011 | Fangrow et al. |
| 8,034,454 B2 | 10/2011 | Terry |
| 8,065,773 B2 | 11/2011 | Vaillancourt et al. |
| 8,066,670 B2 | 11/2011 | Cluff et al. |
| 8,069,523 B2 | 12/2011 | Vaillancourt et al. |
| 8,113,837 B2 | 2/2012 | Zegarelli |
| 8,146,757 B2 | 4/2012 | Abreu et al. |
| 8,162,899 B2 | 4/2012 | Tennican |
| 8,167,847 B2 | 5/2012 | Anderson et al. |
| 8,172,825 B2 | 5/2012 | Solomon et al. |
| 8,177,761 B2 | 5/2012 | Howlett et al. |
| 8,177,772 B2 | 5/2012 | Christensen et al. |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,231,602 B2 | 7/2012 | Anderson et al. |
| 8,252,247 B2 | 8/2012 | Ferlic |
| 8,262,628 B2 | 9/2012 | Fangrow, Jr. |
| 8,262,643 B2 | 9/2012 | Tennican |
| 8,273,303 B2 | 9/2012 | Ferlic et al. |
| 8,281,824 B2 | 10/2012 | Molema et al. |
| 8,328,767 B2 | 12/2012 | Solomon et al. |
| 8,336,152 B2 | 12/2012 | Kerr et al. |
| 8,343,112 B2 | 1/2013 | Solomon et al. |
| 8,361,408 B2 | 1/2013 | Lynn |
| 8,372,045 B2 | 2/2013 | Needle et al. |
| 8,377,040 B2 | 2/2013 | Burkholz et al. |
| 8,414,547 B2 | 4/2013 | DiFiore et al. |
| 8,419,713 B1 | 4/2013 | Solomon et al. |
| 8,454,579 B2 | 6/2013 | Fangrow, Jr. |
| 8,480,968 B2 | 7/2013 | Lynn |
| 8,491,546 B2 | 7/2013 | Hoang et al. |
| 8,500,717 B2 | 8/2013 | Becker |
| 8,506,527 B2 | 8/2013 | Carlyon |
| 8,506,538 B2 | 8/2013 | Chelak |
| 8,523,798 B2 | 9/2013 | DiFiore |
| 8,523,830 B2 | 9/2013 | Solomon et al. |
| 8,523,831 B2 | 9/2013 | Solomon et al. |
| 8,533,887 B2 | 9/2013 | Hirst |
| 8,545,479 B2 | 10/2013 | Kitani et al. |
| 8,568,371 B2 | 10/2013 | Siopes et al. |
| 8,622,995 B2 | 1/2014 | Ziebol et al. |
| 8,622,996 B2 | 1/2014 | Ziebol et al. |
| 8,641,681 B2 | 2/2014 | Solomon et al. |
| 8,641,684 B2 | 2/2014 | Utterberg et al. |
| 8,647,308 B2 | 2/2014 | Solomon et al. |
| 8,647,326 B2 | 2/2014 | Solomon et al. |
| 8,651,271 B1 | 2/2014 | Shen |
| 8,671,496 B2 | 3/2014 | Kerr et al. |
| 8,740,864 B2 | 6/2014 | Hoang et al. |
| 8,758,307 B2 | 6/2014 | Grimm et al. |
| 8,777,504 B2 | 7/2014 | Shaw et al. |
| 8,791,073 B2 | 7/2014 | West et al. |
| 8,845,593 B2 | 9/2014 | Anderson et al. |
| 8,877,231 B2 | 11/2014 | Rosen |

(56) References Cited

U.S. PATENT DOCUMENTS

| | | |
|---|---|---|
| 8,910,919 B2 | 12/2014 | Bonnal et al. |
| 8,920,404 B2 | 12/2014 | DiFiore et al. |
| 8,968,268 B2 | 3/2015 | Anderson et al. |
| 8,981,139 B2 | 3/2015 | Schoenfisch et al. |
| 8,999,073 B2 | 4/2015 | Rogers et al. |
| 9,022,984 B2 | 5/2015 | Ziebol et al. |
| 9,072,296 B2 | 7/2015 | Mills et al. |
| 9,072,868 B2 | 7/2015 | Ziebol et al. |
| 9,078,992 B2 | 7/2015 | Ziebol et al. |
| 9,089,680 B2 | 7/2015 | Ueda et al. |
| 9,095,500 B2 | 8/2015 | Brandenburger et al. |
| 9,095,667 B2 | 8/2015 | Von Schuckmann |
| 9,101,685 B2 | 8/2015 | Li et al. |
| 9,101,750 B2 | 8/2015 | Solomon et al. |
| 9,114,915 B2 | 8/2015 | Solomon et al. |
| 9,125,600 B2 | 9/2015 | Steube et al. |
| 9,149,624 B2 | 10/2015 | Lewis |
| 9,180,252 B2 | 11/2015 | Gelblum et al. |
| 9,192,449 B2 | 11/2015 | Kerr et al. |
| 9,205,248 B2 | 12/2015 | Wu et al. |
| 9,216,440 B2 | 12/2015 | Ma et al. |
| 9,233,208 B2 | 1/2016 | Tekeste |
| 9,242,084 B2 | 1/2016 | Solomon et al. |
| 9,248,093 B2 | 2/2016 | Kelley, III et al. |
| 9,248,229 B2 | 2/2016 | Devouassoux et al. |
| 9,259,284 B2 | 2/2016 | Rogers et al. |
| 9,259,535 B2 | 2/2016 | Anderson et al. |
| 9,283,367 B2 | 3/2016 | Hoang et al. |
| 9,283,368 B2 | 3/2016 | Hoang et al. |
| 9,283,369 B2 | 3/2016 | Ma et al. |
| 9,289,588 B2 | 3/2016 | Chen |
| 9,296,525 B2 | 3/2016 | Murphy et al. |
| 9,302,049 B2 | 4/2016 | Tekeste |
| 9,320,858 B2 | 4/2016 | Grimm et al. |
| 9,320,859 B2 | 4/2016 | Grimm et al. |
| 9,320,860 B2 | 4/2016 | Grimm et al. |
| 9,352,080 B2 | 5/2016 | Goodall et al. |
| 9,352,140 B2 | 5/2016 | Kerr et al. |
| 9,352,141 B2 | 5/2016 | Wong |
| 9,352,142 B2 | 5/2016 | Ziebol et al. |
| 9,381,339 B2 | 7/2016 | Wu et al. |
| 9,399,125 B2 | 7/2016 | Burkholz |
| 9,408,971 B2 | 8/2016 | Carlyon |
| 9,527,660 B2 | 12/2016 | Tennican |
| 9,592,375 B2 | 3/2017 | Tennican |
| 9,700,676 B2 | 7/2017 | Anderson et al. |
| 9,700,677 B2 | 7/2017 | Anderson et al. |
| 9,700,710 B2 | 7/2017 | Anderson et al. |
| 9,707,348 B2 | 7/2017 | Anderson et al. |
| 9,707,349 B2 | 7/2017 | Anderson et al. |
| 9,707,350 B2 | 7/2017 | Anderson et al. |
| 9,809,355 B2 | 11/2017 | Solomon et al. |
| 9,849,276 B2 | 12/2017 | Ziebol et al. |
| 9,867,975 B2 | 1/2018 | Gardner et al. |
| 9,907,617 B2 | 3/2018 | Rogers |
| 9,933,094 B2 | 4/2018 | Fangrow |
| 9,999,471 B2 | 6/2018 | Rogers et al. |
| 10,016,587 B2 | 7/2018 | Gardner et al. |
| 10,046,156 B2 | 8/2018 | Gardner et al. |
| 10,159,829 B2 | 12/2018 | Ziebol et al. |
| 10,166,381 B2 | 1/2019 | Gardner et al. |
| 10,195,000 B2 | 2/2019 | Rogers et al. |
| 10,201,692 B2 | 2/2019 | Chang |
| 10,328,207 B2 | 6/2019 | Anderson et al. |
| 10,525,250 B1 | 1/2020 | Ziebol et al. |
| 10,695,550 B2 | 6/2020 | Gardner et al. |
| 10,744,316 B2 | 8/2020 | Fangrow |
| 10,806,919 B2 | 10/2020 | Gardner et al. |
| 10,821,278 B2 | 11/2020 | Gardner et al. |
| 11,160,932 B2 | 11/2021 | Anderson et al. |
| 11,229,746 B2 | 1/2022 | Anderson et al. |
| 2002/0077693 A1 | 6/2002 | Barclay et al. |
| 2002/0082682 A1 | 6/2002 | Barclay et al. |
| 2002/0098278 A1 | 6/2002 | Bates et al. |
| 2003/0039697 A1 | 2/2003 | Zhao et al. |
| 2003/0062376 A1 | 4/2003 | Sears et al. |
| 2003/0072783 A1 | 4/2003 | Stamler et al. |
| 2003/0153865 A1 | 8/2003 | Connell et al. |
| 2003/0199835 A1 | 10/2003 | Leinsing et al. |
| 2003/0208165 A1 | 11/2003 | Christensen et al. |
| 2004/0034042 A1 | 2/2004 | Tsuji et al. |
| 2004/0034329 A1 | 2/2004 | Mankus et al. |
| 2004/0037836 A1 | 2/2004 | Stamler et al. |
| 2004/0048542 A1 | 3/2004 | Thomaschefsky et al. |
| 2004/0052689 A1 | 3/2004 | Yao |
| 2004/0052831 A1 | 3/2004 | Modak et al. |
| 2004/0156908 A1 | 8/2004 | Polaschegg et al. |
| 2004/0210201 A1 | 10/2004 | Farnan |
| 2004/0215148 A1 | 10/2004 | Hwang et al. |
| 2004/0247640 A1 | 12/2004 | Zhao et al. |
| 2004/0249337 A1 | 12/2004 | DiFiore |
| 2004/0249338 A1 | 12/2004 | DeCant, Jr. et al. |
| 2005/0013836 A1 | 1/2005 | Raad |
| 2005/0015075 A1 | 1/2005 | Wright et al. |
| 2005/0065479 A1 | 3/2005 | Schiller et al. |
| 2005/0098527 A1 | 5/2005 | Yates et al. |
| 2005/0124942 A1 | 6/2005 | Richmond |
| 2005/0124970 A1 | 6/2005 | Kunin et al. |
| 2005/0147524 A1 | 7/2005 | Bousquet |
| 2005/0147525 A1 | 7/2005 | Bousquet |
| 2005/0148930 A1 | 7/2005 | Hseih et al. |
| 2005/0152891 A1 | 7/2005 | Toone et al. |
| 2005/0171493 A1 | 8/2005 | Nicholls |
| 2005/0214185 A1 | 9/2005 | Castaneda |
| 2005/0220882 A1 | 10/2005 | Pritchard et al. |
| 2005/0228362 A1 | 10/2005 | Vaillancourt |
| 2005/0228482 A1 | 10/2005 | Herzog et al. |
| 2005/0256461 A1 | 11/2005 | DiFiore et al. |
| 2005/0265958 A1 | 12/2005 | West et al. |
| 2005/0267421 A1 | 12/2005 | Wing |
| 2005/0271711 A1* | 12/2005 | Lynch .............. A61K 47/24 424/443 |
| 2005/0288551 A1 | 12/2005 | Callister et al. |
| 2006/0004316 A1 | 1/2006 | DiFiore et al. |
| 2006/0024372 A1 | 2/2006 | Utterberg et al. |
| 2006/0058734 A1 | 3/2006 | Phillips |
| 2006/0096348 A1 | 5/2006 | DiFiore |
| 2006/0118122 A1 | 6/2006 | Martens et al. |
| 2006/0129109 A1 | 6/2006 | Shaw et al. |
| 2006/0142730 A1 | 6/2006 | Proulx et al. |
| 2006/0149191 A1 | 7/2006 | DiFiore |
| 2006/0161115 A1 | 7/2006 | Fangrow |
| 2006/0195117 A1 | 8/2006 | Rucker et al. |
| 2006/0202146 A1 | 9/2006 | Doyle |
| 2006/0206178 A1 | 9/2006 | Kim |
| 2006/0253084 A1 | 11/2006 | Nordgren |
| 2006/0261076 A1 | 11/2006 | Anderson |
| 2007/0003603 A1 | 1/2007 | Karandikar et al. |
| 2007/0088292 A1 | 4/2007 | Fangrow |
| 2007/0088293 A1 | 4/2007 | Fangrow |
| 2007/0088294 A1 | 4/2007 | Fangrow |
| 2007/0106205 A1 | 5/2007 | Connell et al. |
| 2007/0167910 A1 | 7/2007 | Tennican et al. |
| 2007/0179453 A1 | 8/2007 | Lim et al. |
| 2007/0187353 A1 | 8/2007 | Fox et al. |
| 2007/0212381 A1 | 9/2007 | DiFiore et al. |
| 2007/0231315 A1 | 10/2007 | Lichte et al. |
| 2007/0248676 A1 | 10/2007 | Stamler et al. |
| 2007/0249996 A1 | 10/2007 | Tennican et al. |
| 2007/0265578 A1 | 11/2007 | Tennican et al. |
| 2007/0287989 A1 | 12/2007 | Crawford et al. |
| 2008/0027399 A1 | 1/2008 | Harding et al. |
| 2008/0027401 A1 | 1/2008 | Ou-Yang |
| 2008/0033371 A1 | 2/2008 | Updegraff et al. |
| 2008/0039803 A1 | 2/2008 | Lynn |
| 2008/0058733 A1 | 3/2008 | Vogt et al. |
| 2008/0093245 A1 | 4/2008 | Periasamy et al. |
| 2008/0095680 A1 | 4/2008 | Steffens et al. |
| 2008/0097315 A1 | 4/2008 | Miner et al. |
| 2008/0097407 A1 | 4/2008 | Plishka |
| 2008/0103485 A1 | 5/2008 | Kruger |
| 2008/0287920 A1 | 5/2008 | Fangrow et al. |
| 2008/0014005 A1 | 6/2008 | Shirley |
| 2008/0128646 A1 | 6/2008 | Clawson |

(56) References Cited

U.S. PATENT DOCUMENTS

| | | |
|---|---|---|
| 2008/0147047 A1 | 6/2008 | Davis et al. |
| 2008/0161763 A1 | 7/2008 | Harding et al. |
| 2008/0172007 A1 | 7/2008 | Bousquet |
| 2008/0177250 A1 | 7/2008 | Howlett et al. |
| 2008/0187460 A1 | 8/2008 | Utterberg et al. |
| 2008/0188791 A1 | 8/2008 | DiFiore et al. |
| 2008/0190485 A1 | 8/2008 | Guala |
| 2008/0262465 A1 | 10/2008 | Zinger et al. |
| 2008/0318333 A1 | 12/2008 | Nielsen et al. |
| 2008/0319423 A1 | 12/2008 | Tanghoj et al. |
| 2009/0008393 A1 | 1/2009 | Howlett et al. |
| 2009/0012426 A1 | 1/2009 | Tennican |
| 2009/0024096 A1 | 1/2009 | Hai et al. |
| 2009/0028750 A1 | 1/2009 | Ryan |
| 2009/0062766 A1 | 3/2009 | Howlett et al. |
| 2009/0093757 A1 | 4/2009 | Tennican |
| 2009/0126867 A1 | 5/2009 | Decant, Jr. et al. |
| 2009/0137969 A1 | 5/2009 | Colantonio et al. |
| 2009/0149820 A1 | 6/2009 | DiFiore |
| 2009/0163876 A1 | 6/2009 | Chebator et al. |
| 2009/0205151 A1 | 8/2009 | Fisher et al. |
| 2009/0205656 A1 | 8/2009 | Nishibayashi et al. |
| 2009/0247485 A1 | 10/2009 | Ahmed et al. |
| 2009/0259194 A1 | 10/2009 | Pinedjian et al. |
| 2009/0270832 A1 | 10/2009 | Vancaillie et al. |
| 2009/0293882 A1 | 12/2009 | Terry |
| 2010/0004510 A1 | 1/2010 | Kuroshima |
| 2010/0049170 A1 | 2/2010 | Solomon et al. |
| 2010/0050351 A1 | 3/2010 | Colantonio et al. |
| 2010/0064456 A1 | 3/2010 | Ferlic |
| 2010/0074932 A1 | 3/2010 | Talsma |
| 2010/0137472 A1 | 6/2010 | Ou-Yang |
| 2010/0143427 A1 | 6/2010 | King et al. |
| 2010/0152670 A1 | 6/2010 | Low |
| 2010/0160894 A1 | 6/2010 | Julian et al. |
| 2010/0172794 A1 | 7/2010 | Ferlic et al. |
| 2010/0242993 A1 | 9/2010 | Hoang et al. |
| 2010/0253070 A1 | 10/2010 | Cheon et al. |
| 2010/0280805 A1 | 11/2010 | DiFiore |
| 2010/0292673 A1 | 11/2010 | Korogi et al. |
| 2010/0292674 A1 | 11/2010 | Jepson et al. |
| 2010/0306938 A1 | 12/2010 | Rogers et al. |
| 2010/0318040 A1 | 12/2010 | Kelley, III et al. |
| 2011/0030726 A1 | 2/2011 | Vaillancourt et al. |
| 2011/0044850 A1 | 2/2011 | Solomon et al. |
| 2011/0046564 A1 | 2/2011 | Zhong |
| 2011/0046603 A1 | 2/2011 | Felsovalyi et al. |
| 2011/0062703 A1 | 3/2011 | Lopez |
| 2011/0064512 A1 | 3/2011 | Shaw et al. |
| 2011/0071475 A1 | 3/2011 | Horvath et al. |
| 2011/0082431 A1 | 4/2011 | Burgess et al. |
| 2011/0184338 A1 | 7/2011 | McKay |
| 2011/0184382 A1 | 7/2011 | Cady |
| 2011/0208128 A1 | 8/2011 | Wu et al. |
| 2011/0217212 A1 | 9/2011 | Solomon et al. |
| 2011/0276031 A1 | 11/2011 | Hoang et al. |
| 2011/0282302 A1 | 11/2011 | Lopez et al. |
| 2011/0311602 A1 | 12/2011 | Mills et al. |
| 2011/0314619 A1 | 12/2011 | Schweikert |
| 2012/0022469 A1 | 1/2012 | Albert et al. |
| 2012/0031904 A1 | 2/2012 | Kuhn et al. |
| 2012/0039764 A1 | 2/2012 | Solomon et al. |
| 2012/0083730 A1 | 4/2012 | Rush et al. |
| 2012/0083750 A1 | 4/2012 | Sansoucy |
| 2012/0157965 A1 | 6/2012 | Wotton et al. |
| 2012/0191029 A1 | 7/2012 | Hopf et al. |
| 2012/0195807 A1 | 8/2012 | Ferlic |
| 2012/0216359 A1 | 8/2012 | Rogers et al. |
| 2012/0216360 A1 | 8/2012 | Rogers et al. |
| 2012/0220955 A1 | 8/2012 | Maseda et al. |
| 2012/0283696 A1 | 11/2012 | Cronenberg et al. |
| 2012/0302968 A1 | 11/2012 | Tennican |
| 2012/0302970 A1 | 11/2012 | Tennican |
| 2012/0302997 A1 | 11/2012 | Gardner et al. |
| 2012/0315201 A1 | 12/2012 | Ferlic et al. |
| 2013/0030414 A1 | 1/2013 | Gardner et al. |
| 2013/0035667 A1 | 2/2013 | Anderson et al. |
| 2013/0039953 A1 | 2/2013 | Dudnyk et al. |
| 2013/0053751 A1 | 2/2013 | Holtham |
| 2013/0072908 A1 | 3/2013 | Solomon et al. |
| 2013/0085313 A1 | 4/2013 | Fowler et al. |
| 2013/0085474 A1 | 4/2013 | Charles et al. |
| 2013/0098398 A1 | 4/2013 | Kerr et al. |
| 2013/0098938 A1 | 4/2013 | Efthimiadis |
| 2013/0102950 A1 | 4/2013 | DiFiore |
| 2013/0123754 A1 | 5/2013 | Solomon et al. |
| 2013/0134161 A1 | 5/2013 | Fogel et al. |
| 2013/0138085 A1 | 5/2013 | Tennican |
| 2013/0144258 A1 | 6/2013 | Ziebol et al. |
| 2013/0150795 A1 | 6/2013 | Snow |
| 2013/0164189 A1 | 6/2013 | Hadden |
| 2013/0171030 A1 | 7/2013 | Ferlic et al. |
| 2013/0183635 A1 | 7/2013 | Wilhoit |
| 2013/0197485 A1 | 8/2013 | Gardner et al. |
| 2014/0042116 A1 | 2/2014 | Shen et al. |
| 2014/0048079 A1 | 2/2014 | Gardner et al. |
| 2014/0052074 A1 | 2/2014 | Tekeste |
| 2014/0101876 A1 | 4/2014 | Rogers et al. |
| 2014/0155868 A1 | 6/2014 | Nelson et al. |
| 2014/0227144 A1 | 8/2014 | Liu et al. |
| 2014/0228775 A1 | 8/2014 | Burkholz et al. |
| 2014/0228809 A1 | 8/2014 | Wong |
| 2014/0243797 A1 | 8/2014 | Jensen et al. |
| 2014/0249476 A1 | 9/2014 | Grimm et al. |
| 2014/0249477 A1 | 9/2014 | Grimm et al. |
| 2014/0249486 A1 | 9/2014 | Grimm et al. |
| 2014/0336610 A1* | 11/2014 | Michel .............. A61M 5/1409 366/152.2 |
| 2014/0339812 A1 | 11/2014 | Carney et al. |
| 2014/0339813 A1 | 11/2014 | Cederschiöld et al. |
| 2015/0141934 A1 | 5/2015 | Gardner et al. |
| 2015/0148287 A1 | 5/2015 | Woo et al. |
| 2015/0165127 A1 | 6/2015 | Haefele et al. |
| 2015/0217106 A1 | 8/2015 | Banik et al. |
| 2015/0231380 A1 | 8/2015 | Hoang et al. |
| 2015/0237854 A1 | 8/2015 | Mills et al. |
| 2015/0238703 A1 | 8/2015 | Glocker |
| 2015/0258324 A1 | 9/2015 | Chida et al. |
| 2015/0273199 A1 | 10/2015 | Adams et al. |
| 2015/0297455 A1 | 10/2015 | Sanders et al. |
| 2015/0297881 A1 | 10/2015 | Sanders et al. |
| 2015/0306367 A1 | 10/2015 | DiFiore |
| 2015/0306369 A1 | 10/2015 | Burkholz et al. |
| 2015/0314119 A1 | 11/2015 | Anderson et al. |
| 2015/0320926 A1 | 11/2015 | Fitzpatrick et al. |
| 2015/0320992 A1 | 11/2015 | Bonnet et al. |
| 2015/0343174 A1 | 12/2015 | Ziebol et al. |
| 2015/0374968 A1 | 12/2015 | Solomon et al. |
| 2016/0001056 A1 | 1/2016 | Nelson et al. |
| 2016/0001058 A1 | 1/2016 | Ziebol et al. |
| 2016/0015863 A1 | 1/2016 | Gupta et al. |
| 2016/0015931 A1 | 1/2016 | Ryan et al. |
| 2016/0015959 A1 | 1/2016 | Solomon et al. |
| 2016/0045629 A1 | 2/2016 | Gardner et al. |
| 2016/0067365 A1 | 3/2016 | Ma et al. |
| 2016/0067471 A1 | 3/2016 | Ingram et al. |
| 2016/0088995 A1 | 3/2016 | Ueda et al. |
| 2016/0089530 A1 | 3/2016 | Sathe |
| 2016/0101223 A1 | 4/2016 | Kelley, III et al. |
| 2016/0101276 A1 | 4/2016 | Tekeste |
| 2016/0106969 A1 | 4/2016 | Neftel |
| 2016/0121097 A1 | 5/2016 | Steele |
| 2016/0144118 A1 | 5/2016 | Solomon et al. |
| 2016/0158520 A1 | 6/2016 | Ma et al. |
| 2016/0158521 A1 | 6/2016 | Hoang et al. |
| 2016/0158522 A1 | 6/2016 | Hoang et al. |
| 2016/0184527 A1 | 6/2016 | Tekeste |
| 2016/0213912 A1 | 7/2016 | Daneluzzi |
| 2016/0250420 A1 | 9/2016 | Maritan et al. |
| 2016/0354596 A1 | 12/2016 | DiFiore |
| 2017/0020911 A1 | 1/2017 | Berry et al. |
| 2017/0042636 A1 | 2/2017 | Young |
| 2017/0143447 A1 | 5/2017 | Rogers et al. |
| 2017/0182241 A1 | 6/2017 | DiFiore |

(56) References Cited

U.S. PATENT DOCUMENTS

| | | | |
|---|---|---|---|
| 2017/0203092 A1 | 7/2017 | Ryan et al. |
| 2017/0239443 A1 | 8/2017 | Abitabilo et al. |
| 2017/0361023 A1 | 12/2017 | Anderson et al. |
| 2018/0028403 A1 | 2/2018 | Fangrow |
| 2018/0200500 A1 | 7/2018 | Ziebol et al. |
| 2018/0214684 A1 | 8/2018 | Avula et al. |
| 2018/0369562 A1 | 12/2018 | Gardner |
| 2019/0038888 A1 | 2/2019 | Gardner |
| 2019/0111245 A1 | 4/2019 | Gardner et al. |
| 2019/0201681 A1 | 7/2019 | Ziebol et al. |
| 2019/0282795 A1 | 9/2019 | Fangrow |
| 2020/0085690 A1 | 3/2020 | Fangrow |
| 2020/0139037 A1 | 5/2020 | Ziebol et al. |
| 2020/0139101 A1 | 5/2020 | Ziebol et al. |
| 2020/0139102 A1 | 5/2020 | Ziebol et al. |
| 2020/0139103 A1 | 5/2020 | Ziebol et al. |
| 2020/0139104 A1 | 5/2020 | Ziebol et al. |
| 2020/0155794 A1 | 5/2020 | Ziebol |
| 2020/0324102 A1 | 10/2020 | Fangrow |
| 2020/0330741 A1 | 10/2020 | Fangrow |
| 2020/0406020 A1 | 12/2020 | Fangrow |
| 2021/0093791 A1 | 4/2021 | Anderson |
| 2021/0162194 A1 | 6/2021 | Gardner |
| 2021/0205596 A1 | 7/2021 | Ziebol et al. |
| 2021/0308442 A1 | 10/2021 | Gardner |

FOREIGN PATENT DOCUMENTS

| | | |
|---|---|---|
| CA | 2 841 832 | 6/2019 |
| CN | 2402327 Y | 10/2000 |
| CN | 2815392 Y | 9/2006 |
| CN | 201150420 Y | 11/2008 |
| CN | 201519335 U | 7/2010 |
| CN | 106902402 | 6/2017 |
| DE | 3515665 | 5/1986 |
| DE | 89 06 628 U1 | 9/1989 |
| DE | 43 34 272 | 4/1995 |
| DE | 29617133 | 1/1997 |
| EP | 0 088 341 | 9/1983 |
| EP | 0 108 785 | 5/1984 |
| EP | 0 174 162 | 3/1986 |
| EP | 0 227 219 | 7/1987 |
| EP | 0 237 239 | 9/1987 |
| EP | 0 245 872 | 11/1987 |
| EP | 0 257 485 | 3/1988 |
| EP | 0 639 385 | 2/1995 |
| EP | 0 734 721 | 10/1996 |
| EP | 0 769 265 | 4/1997 |
| EP | 1 061 000 | 10/2000 |
| EP | 1 331 020 | 7/2003 |
| EP | 1 471 011 | 10/2004 |
| EP | 1 442 753 | 2/2007 |
| EP | 1 813 293 | 8/2007 |
| EP | 1 977 714 | 10/2008 |
| EP | 2 444 117 | 4/2012 |
| EP | 2 606 930 | 6/2013 |
| EP | 2 671 604 | 12/2013 |
| EP | 2 731 658 | 5/2014 |
| FR | 2 493 149 A | 5/1982 |
| FR | 2 506 162 | 11/1982 |
| FR | 2 782 910 | 3/2000 |
| GB | 123221 | 2/1919 |
| GB | 2 296 182 | 6/1996 |
| GB | 2 333 097 | 7/1999 |
| GB | 2 387 772 | 10/2003 |
| JP | 57-131462 U | 8/1982 |
| JP | 04-99950 | 2/1992 |
| JP | 09-216661 A | 8/1997 |
| JP | 2000-157630 A | 6/2000 |
| JP | 2002-234567 A | 8/2002 |
| JP | 2002-291906 | 10/2002 |
| JP | 2005-218649 | 8/2005 |
| JP | 2006-182663 A | 7/2006 |
| JP | 2011-036691 | 2/2011 |
| JP | 2011-528647 | 11/2011 |
| JP | 2013-520287 | 6/2013 |
| JP | 2014-117461 | 6/2014 |
| RU | 2 246 321 C1 | 2/2005 |
| WO | WO 83/03975 | 11/1983 |
| WO | WO 85/05040 | 11/1985 |
| WO | WO 93/20806 | 10/1993 |
| WO | WO 95/07691 | 3/1995 |
| WO | WO 96/35416 | 11/1996 |
| WO | WO 96/38136 | 12/1996 |
| WO | WO 1997/19701 | 6/1997 |
| WO | WO 98/12125 | 3/1998 |
| WO | WO 1999/44665 | 9/1999 |
| WO | WO 2001/70199 A1 | 9/2001 |
| WO | WO 2002/05188 | 1/2002 |
| WO | WO 2002/47581 | 6/2002 |
| WO | WO 2002/49544 | 6/2002 |
| WO | WO 2003/015677 | 2/2003 |
| WO | WO 2003/070296 | 8/2003 |
| WO | WO 2004/035129 | 4/2004 |
| WO | WO 2004/112846 | 12/2004 |
| WO | WO 2005/112954 A1 | 12/2005 |
| WO | WO 2005/112974 A2 | 12/2005 |
| WO | WO 2006/007690 | 1/2006 |
| WO | WO 2006/044236 | 4/2006 |
| WO | WO 2006/102756 | 10/2006 |
| WO | WO 2007/008511 | 1/2007 |
| WO | WO 2007/056773 | 5/2007 |
| WO | WO 2007/137056 | 11/2007 |
| WO | WO 2008/042285 | 4/2008 |
| WO | WO 2008/086631 | 7/2008 |
| WO | WO 2008/089196 | 7/2008 |
| WO | WO 2008/100950 | 8/2008 |
| WO | WO 2008/140807 | 11/2008 |
| WO | WO 2009/002474 | 12/2008 |
| WO | WO 2009/060322 | 5/2009 |
| WO | WO 2009/117135 | 9/2009 |
| WO | WO 2009/123709 | 10/2009 |
| WO | WO 2009/136957 | 11/2009 |
| WO | WO 2009/153224 | 12/2009 |
| WO | WO 2010/002757 | 1/2010 |
| WO | WO 2010/002808 | 1/2010 |
| WO | WO 2010/011616 | 1/2010 |
| WO | WO 2010/034470 | 4/2010 |
| WO | WO 2010/039171 | 4/2010 |
| WO | WO 2010/062589 | 6/2010 |
| WO | WO 2011/028722 | 3/2011 |
| WO | WO 2011/053924 | 5/2011 |
| WO | WO 2011/106374 | 9/2011 |
| WO | WO 2011/119021 | 9/2011 |
| WO | WO 2012/118829 | 9/2012 |
| WO | WO 2012/162006 | 11/2012 |
| WO | WO 2013/009998 | 1/2013 |
| WO | WO 2013/023146 | 2/2013 |
| WO | WO 2012/184716 | 12/2013 |
| WO | WO 2013/192574 | 12/2013 |
| WO | WO 2014/074929 | 5/2014 |
| WO | WO 2014/140949 | 9/2014 |
| WO | WO 14/159346 | 10/2014 |
| WO | WO 2015/074087 | 5/2015 |
| WO | WO 2015/119940 | 8/2015 |
| WO | WO 2015/120336 | 8/2015 |
| WO | WO 2015/164129 | 10/2015 |
| WO | WO 2015/168677 | 11/2015 |
| WO | WO 2015/174953 | 11/2015 |
| WO | WO 2016/025775 | 2/2016 |
| WO | WO 2016/182822 | 11/2016 |
| WO | WO 2017/015047 | 1/2017 |
| WO | WO 2017/127364 | 7/2017 |
| WO | WO 2017/127365 | 7/2017 |
| WO | WO 2018/009653 | 1/2018 |
| WO | WO 2018/071717 | 4/2018 |
| WO | WO 2018/204206 A2 | 11/2018 |
| WO | WO 2018/237090 | 12/2018 |
| WO | WO 2018/237122 | 12/2018 |
| WO | WO 2019/178560 | 9/2019 |
| WO | WO 2019/246472 | 12/2019 |
| WO | WO 2020/097366 | 5/2020 |
| WO | WO 2020/251947 | 12/2020 |

(56) References Cited

FOREIGN PATENT DOCUMENTS

OTHER PUBLICATIONS

International Search Report and Written Opinion in corresponding International Patent Application No. PCT/US2018/030015, dated Aug. 27, 2018, in 12 pages.
Antibiotic Lock Therapy Guidline, Stanford Hospital and Clinics, Pharmacy Department Policies and Procedures, issued Jun. 2011.
"Small-bore connectors for liquids and gases in healthcare applications—Part : Connectors for intravascular or hypodermic applications," ISO 80369-7, Corrected version dated Dec. 1, 2016 (50 pages).
Hospira, "You Work in Neverland," Lifeshield Product Brochure in 2 pages, Published 2009.
Baxter Minicap: Photographs of the Baxter Minicap (Sep. 1, 1998) (4 pages).
Baxter, "Peritoneal Dialysis Patient Connectology," Product Descriptions in 1 page, downloaded Jul. 1, 2011.
Beta Cap II Advertisement from Quinton Instrument Co. (Aug. 1981).
Catheter Connections, "Introducing DualCap," Product Brochure in 1 page, Copyright 2011.
Charney, "Baxter Healthcare InterlinkTM IV Access System" in 1 page, from Handbook of Modern Hospital Safety. Published Mar. 1999.
Clave® Needlefree Connector, icumedial, human connections, 2 page brochure. 2012, M1-1065 Rev. 04.
Conical Fittings: International Standard, "Conical fittings with 6% (Luer) Taper for Syringes, Needles and certain Other Medical Equipment—Part 2: Lock Fittings", Ref. No. ISO 594-2:1998. International Organization for Standardization (Sep. 1, 1998) 2nd ed. (16 pages).

Devine, Redacted version of letter from David A. Divine, Esq. of Lee & Hayes, dated May 16, 2011 (3 pages).
Devine, Redacted version of letter from David A. Divine, Esq. of Lee & Hayes, dated May 27, 2011 (3 pages).
Du. Y, et al. Protein adsorption on polyurethane catheters modified with a novel antithrombin-heparin covalent complex, Journal of Biomedical Materials Research Part A, 2006, 216-225.
Holmer, E. et al. The molecular-weight dependence of the rate-enhancing effect of heparin on the inhibition of thrombin, Factor Xa, Factor IXa, Factor XIa, Factor XIIa and kallikrein by antithrombin, Biochem. J. (1981) 193, 395-400.
Hyprotek, "Port Protek," Product Brochure in 1 page, downloaded Sep. 19, 2011 from http://www.hyprotek.com/products.html.
ICU Medical Antimicrobial Microclave, first sold Jan. 21, 2010, p. 1-2.
Klement, P. et al. Chronic performance of polyurethane catheters covalently coated with ATH complex: A rabbit jugular vein model, Biomaterials, (2006), 27, 5107-5117.
Menyhay et al., "Disinfection of Needleless Catheter Connectors and Access Ports with Alcohol May Not Prevent Microbial Entry: The Promise of a Novel Antiseptic-Barrier Cap" Infection Control Hospital and Epidemiology, vol. 27, No. 1 (Jan. 2006) (5 pages).
Otto, Mosby's Pocket Guide to Infusion Therapy. Elsevier Health Sciences, 2004. Pages 65-66. Accessed at: http://books.google.com/books?id=j8T14HwWdS4C&lpg=PP1&pg=PP1#v=onepage&f=false (Year: 2004).
Photographs of the Baxter Minicap (Sep. 1, 1998) (4 pages).
Quinton Beta Capp II advertisement, in 3 pages.
V-Link Luer Activated Device, with VitalShield Protective Coating, 2 page brochure, Baxter Dec. 2009.
International Preliminary Report on Patentability, re PCT Application No. PCT/US2018/030015, dated Mar. 10, 2020.

* cited by examiner

MEDICAL FLUID CONNECTORS AND METHODS FOR PROVIDING ADDITIVES IN MEDICAL FLUID LINES

PRIORITY CLAIM AND INCORPORATION BY REFERENCE

This application claims the benefit under 35 U.S.C. § 120 and 35 U.S.C. § 365(c) as a continuation of International Application No. PCT/US2018/030015, designating the United States, with an international filing date of Apr. 27, 2018, titled "MEDICAL FLUID CONNECTORS AND METHODS FOR PROVIDING ADDITIVES IN MEDICAL FLUID LINES," which claims the benefit under 35 U.S.C. § 119(e) of U.S. Provisional Patent Application No. 62/492,887, filed on May 1, 2017, U.S. Provisional Patent Application No. 62/520,300, filed on Jun. 15, 2017, U.S. Provisional Patent Application No. 62/558,618, filed on Sep. 14, 2017, and U.S. Provisional Patent Application No. 62/662,149, filed on Apr. 24, 2018, which are hereby incorporated by reference herein in their entireties, forming part of the present disclosure. Any feature, structure, material, method, or step that is described and/or illustrated in any embodiment in any of the foregoing provisional patent applications can be used with or instead of any feature, structure, material, method, or step that is described and/or illustrated in the following paragraphs of this specification or the accompanying drawings.

BACKGROUND

Field

This disclosure relates generally to medical fluid connectors, and specifically to medical fluid connectors for providing additives in medical fluid lines.

Description of the Related Art

In healthcare settings where an intravenous (IV) catheter is inserted into a patient, there is an ever-present risk of microbial invasion into the catheter, which can lead to a catheter-related bloodstream infection (CRBSI) in the patient. There are many negative effects of CRBSI's, including serious health risks and increased costs for additional patient treatment. It is common practice in situations where the risk of contracting a CRBSI is particularly high, such as in long-term uses of central venous catheters, to utilize an anti-microbial lock procedure to provide a static anti-microbial solution in the catheter when fluid is not being transferring to or from the patient through the catheter.

SUMMARY

Disclosed are embodiments of medical fluid connectors and/or fluid-modifying devices configured to receive, convey, and/or dispense medical liquid, methods of making the same, and methods of using the same. In some embodiments, the medical connector or fluid-modifying device can be structured to include an initial stage in which medical liquid is infused into the connector and at least a portion of the medical liquid (or all of the medical liquid) is dispensed out of the connector essentially unchanged. The medical connector or fluid-modifying device also can be structured to include a subsequent or final stage in which medical liquid is not infused into the connector and a volume of therapeutic liquid is dispensed out of the connector. In some embodiments, as illustrated, the connector or fluid-modifying device transitions automatically from the initial stage to the subsequent or final stage (e.g., without mechanical actuation or manipulation by a user of a switch or product setting or device configuration), such as by operation of fluid flow only and/or by one or more changes in a force propagated in or through a fluid. In some embodiments, the connector transitions from the initial stage to the subsequent stage by manual actuation by a user, such as by moving or changing a fluid pathway and/or opening a valve within or on the connector. The therapeutic liquid can include a portion of the volume of the medical liquid that was infused into the connector in the initial stage plus a therapeutic additive.

Some embodiments disclosed or claimed in this specification, or in any applications that claim priority to this specification, will overcome one or more of the identified shortcomings in the prior art. However, not all embodiments disclosed or claimed in this specification, or in any applications that claim priority to this specification, will overcome any or all of the identified shortcomings of the prior art, but can be useful for one or more other purposes.

DETAILED DESCRIPTION

Figure 1:
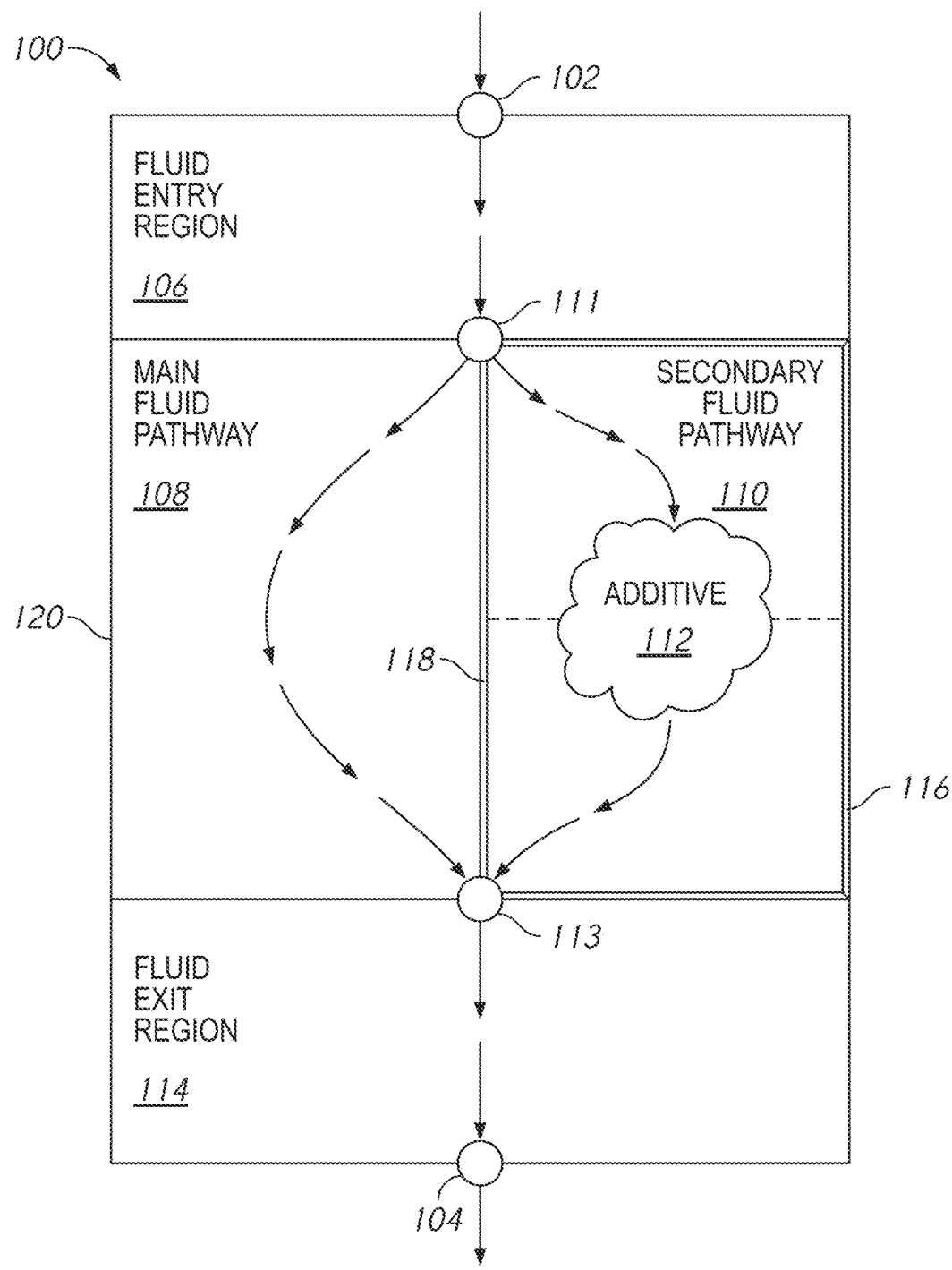
FIG. 1 is a schematic illustration of a medical fluid connector.

Some embodiments disclosed herein pertain to medical connectors, fluid dispensers, and/or fluid modifiers. In some embodiments, the medical connectors include fluid modifiers that infuse a medical fluid with one or more additives, or permit the addition of one or more additives into a medical fluid, or modify a medical fluid in some other way, as the medical fluid passes through or is dispensed from the connector. In some embodiments, methods of making and/or using the disclosed connectors are provided. The following description provides context and examples, but should not be interpreted to limit the scope of the inventions covered by the claims that follow in this specification or in any other application that claims priority to this specification. No single component or collection of components is essential or indispensable. For example, some embodiments may not include a fluid modifier. Any feature, structure, component, material, step, or method that is described and/or illustrated in any embodiment in this specification can be used with or instead of any feature, structure, component, material, step, or method that is described and/or illustrated in any other embodiment in this specification. The relative sizes and dimensions of components shown in the drawings are not limiting if not present in a claim, but are intended to form part of the supporting disclosure in this specification when claimed.

While conventional procedures for achieving anti-microbial locks exist, those procedures are time-consuming, require the acquisition, storage, and use of multiple liquids, may be highly dependent on the techniques employed by healthcare providers for successful outcomes (subject to human error or variation), and may not deliver the antimicrobial solution in an effective dosage or in a useful timing sequence. Some embodiments disclosed herein address one or more of these issues and/or other issues that can occur when using a catheter or while performing a conventional antimicrobial lock method with conventional equipment. In some embodiments, a medical fluid connector configured to provide an additive (e.g., an antimicrobial compound, etc.) to the catheter as a locking solution is provided. In some embodiments, as a medical fluid is passed through the connector, an initial volume of the medical fluid is unchanged or substantially unchanged, having little or no additive added to it, such that there is no clinically significant effect. In some embodiments, after the initial volume of medical fluid passes through the medical connector, the connector is configured to then permit removal of or distribute or expel (automatically, in some devices) an additive-infused or otherwise modified or different portion of medical fluid out of the connector and into the catheter. In some embodiments, a delayed release of additive into the medical fluid locks the catheter without infusing any (or substantially any or any clinically significant amount) of the locking solution (e.g., the additive-infused medical fluid) into the patient. For example, the initial liquid volume can be sufficient to flush the liquid container within the catheter into the patient (e.g., at least about 5 mL, or at least about 3 mL, or at least about 2 mL, etc.), and the volume of additive-infused liquid can be approximately equal to or less than the volume of liquid that is inside of the catheter in communication with the patient's blood flow (e.g., less than or equal to about 5 ml, or less than or equal to about 3 mL, or less than or equal to about 2 mL, etc.), or approximately equal to or less than the volume of liquid that is configured to be inside of the portion of the patient's catheter that is outside of the patient.

As illustrated in FIG. 1, in some embodiments, a medical fluid connector 100 can comprise a housing 120, a fluid inlet or upstream connector 102, a fluid entry region 106, a main fluid pathway 108, a secondary fluid pathway 110, an additive 112, a fluid exit region 114, and a fluid outlet or downstream connector 104. As with all embodiments in this specification, any component(s) can be omitted. For example, a medical fluid connector 100 can omit the fluid entry region 106 and/or fluid exit region 114 (e.g., the fluid can enter or exit directly into or from another part of the connector 100. In the example illustrated, the connector 100 can be configured to: (a) receive a medical liquid in the inlet 102, such as saline or water or another medical liquid (e.g., a glucose solution, a dextrose solution, a nutrient solution, a medicated or pharmaceutical solution, etc.); (b) permit a portion of the medical liquid to travel in the main fluid pathway 108 through to the fluid exit region 114 and out of the fluid outlet 104 without a clinically significant change to the liquid; and (c) permit another portion of the liquid to travel in the secondary fluid pathway 110 where it becomes mixed with an additive 112 and then moves into the fluid exit region 114 and out of the fluid outlet 104. In some embodiments, the medical liquid travelling through the secondary fluid pathway 110 can be offset in time, or out of phase, or delayed or advanced as compared to the medical liquid travelling through the main fluid pathway 108. In some embodiments, all or essentially all of the medical liquid infused into the connector is modified to include an additive, such as by first passing through a region of the connector containing a fluid modifier before exiting the connector. For example, in some embodiments, the main fluid pathway 108 and the secondary fluid pathway 110 are the same or overlap or are positioned in series flow rather than in parallel flow (as illustrated), such that all or essentially all of the medical liquid that is infused into the connector includes at least one additive before exiting the connector.

The main fluid pathway 108 and the secondary fluid pathway 110 can be separated by one or more physical barriers, or can constitute different portions of a single liquid flow being transported through the connector 100, or can represent a single liquid pathway in one or more different phases or configurations. In some embodiments, as shown, liquid that flows directly through the main fluid pathway 108, without deviating into the secondary fluid pathway 100, can be isolated or separated from the additive 112 or from a carrier, such as a matrix or substrate or other holder, of additive 112, during one or more phases, stages, or configurations of use. As illustrated, in some embodiments, the main fluid pathway 108 is essentially straight and/or is essentially co-linear or co-axial with the main central axis or longitude of the connector 200, while the secondary fluid pathway 110 can comprise at least a portion that is offset or spaced laterally from the main central axis or longitude of the connector 200, and/or non-parallel with the main central axis or longitude of the connector 200, and/or can include one or more turns or can follow a tortuous pathway through the connector 200. As shown, the secondary fluid pathway 110 can create more turbulence during fluid flow than the main fluid pathway 108, and/or can be configured to direct fluid through at least a portion of the secondary fluid pathway 110 in a direction that is different from or generally or completely opposite from the direction of fluid flow through the main fluid pathway 108. In situations where the main fluid pathway 108 and the secondary fluid pathway 110 are separated by one or more physical barriers, a first diversion region 111 can be a location or a structure where the pathways 108, 110 separate or are caused to separate; and a second diversion region 113 can be a location or a structure where the separate pathways 108, 110 recombine or are caused to recombine. In many embodiments, either or both of the first and second diversion regions 111, 113 are omitted. In some embodiments, as shown in FIGS. 2A-3F and 6A-13, the first and second diversion regions 111, 113 can be positioned in the same location or substantially the same location (e.g., in or around a transitional region 274, 274A, 274B, 274C, 274D), and/or can exist or take effect at different times, depending on fluid-flow dynamics or changing configurations or positions of the structure of the connector 100. In some embodiments, as shown in FIG. 1, the first and second diversion regions are not at the same location. In some embodiments, including those illustrated in FIG. 2A, a carrier of the additive 112 or the additive 112 itself does not block or clog or impede the flow of fluid through the main fluid pathway 108 and/or the secondary fluid pathway 110 in a manner that would otherwise significantly diminish the fluid flow volume or rate.

Any of these steps and/or structures can be omitted. For example, in some embodiments, the connector 100 can be configured to permit all of the liquid to flow through a fluid pathway that includes one or more additives (e.g., if the additive is provided in the main fluid pathway and there is no secondary fluid pathway). In some embodiments, the one or more additives can be antimicrobial additives. As also described elsewhere herein, any other type of one or more additives can be used for any other type of patient therapy, with or without one or more antimicrobial additives.

As illustrated, in some embodiments, the connector 100 can comprise a fluid modifier 116 to alter one or more qualities of the liquid flow through the connector 100, such as by modifying the direction or size or shape of the liquid pathway through the connector 100 (e.g., in the secondary fluid pathway 110 and/or in the main fluid pathway 108), and/or by modifying the composition of the liquid flowing through the connector 100, such as by adding one or more additives 112 to the liquid flowing through the connector 100. A fluid modifier 116 may perform a single function or multiple functions. For example, in some embodiments, the fluid modifier 116 can: (a) permit the secondary fluid pathway to temporarily increase in size or volume or length; and/or (b) the fluid modifier 116 can affect the timing or sequence of the passage of liquid through the secondary fluid pathway, such as by delaying the passage of liquid that enters and/or that travels through the secondary fluid pathway 110 as compared to the passage of liquid through the main fluid pathway 108 (e.g., liquid that passes by and/or does not travel through the secondary fluid pathway 110); and/or (c) the fluid modifier 116 can include a coating or a dusting or an impregnation or any other suitable application or placement or attachment of one or more additives on or in or underneath or covered by or surrounded by the fluid modifier 116 that can be dispersed from or by the fluid modifier 116 into the liquid passing through or around the fluid modifier 116 in a dosage, timing, and/or sequence that is clinically effective for a therapeutic use, such as for providing an anti-microbial lock.

For example, in some embodiments, the connector 100 can be configured to receive through the fluid inlet 102 a first medical liquid, such as saline or water or some other medical liquid, and to deliver out of the fluid outlet 104 a predetermined initial volume of saline or water or some other medical liquid that has the same or essentially or substantially the same composition or the same or substantially the same clinical effect as the first medical liquid, and then subsequently to deliver out of the fluid outlet 104 a predetermined secondary volume of a second medical liquid that is comprised of the first medical liquid plus a clinically significant concentration of one or more additives 112 that can be used to provide an effective therapy to a patient, such as an anti-microbial lock in a catheter line. Any other desired liquid delivery profile can be accomplished, such as an additional or alternative fluid delivery concentration or composition or sequence. For example, the first medical liquid can include a clinically significant concentration of one or more additives, followed by a second medical liquid that does not include a clinically significant concentration of one or more additives or that includes a different clinically significant concentration of one or more additives (e.g., if the main fluid pathway 108 and the secondary fluid pathway 110 both include one or more additives, or if there is an additional fluid pathway or if there are layers of additives positioned within the pathway); or a generally uniform concentration of one or more additives can be provided through substantially the entire period of infusion of liquid through the connector 100. In some embodiments, the fluid modifier 116 or the connector 100 does not include any additive 112, but may accomplish one or more other purposes, such as performing a delay in the delivery of fluid or a pre-determine liquid-delivery sequence.

In some embodiments, as also described elsewhere herein, the secondary pathway 110 can fill as a result of, for example, a threshold volume and/or threshold rate of liquid passing into and/or through the main fluid pathway 108.

In some embodiments, the connector 100 comprises one or more additional fluid pathways (not shown) that fill before or after or while the secondary fluid pathway fills or is filled. In some embodiments, as described elsewhere herein, the additional pathways can fill as a result of, for example, a specific (e.g., threshold) volume and/or rate of liquid passing through the main fluid pathway and/or as a result of a specific (e.g., threshold) volume and/or rate of liquid passing through or into the secondary fluid pathway. In some embodiments, using a multistage configuration allows multiple infusion profiles or infusion profiles with multiple stages or changes to be obtained. In some embodiments, multiple connectors can be used (e.g., connected)

serially or in any other way to achieve any of various clinically significant infusion profiles.

In some embodiments, there can be a boundary 118 that is in contact with or surrounding either or both of the main fluid pathway 108 and the secondary fluid pathway 110 or that is positioned between the main fluid pathway 108 and the secondary fluid pathway 100. The boundary can be configured to move, thereby changing either or both of the volumes or path lengths of the main fluid pathway 108 and the secondary fluid pathway 110, such as in a generally inverse relationship. In some embodiments, one or more valves can be provided between the main fluid pathway 108 and the secondary fluid pathway 110. For example, either or both of diversion regions 111, 113 can comprise a valve for selectively permitting or impeding fluid flow from the fluid entry region 106 and/or into the fluid exit region 114. The valve can transition between open and closed positions manually by a user or automatically (e.g., based upon a quantity of fluid flow or volume or a change in fluid pressure, or in some other way). In some embodiments, the valve or valves are responsive to a certain volume or force achieved in the main fluid pathway and/or in the secondary fluid pathway. In some embodiments, the connector 100 is configured to provide a desired dosage or concentration of one or more additives after a pre-determined period of time or after a pre-determined volume of liquid has passed through the connector 100, and/or during a pre-determined period of time or while a pre-determined volume of liquid is passing through the connector, in the medical liquid that flows out of the fluid outlet 104 of the connector 100.

In some embodiments, the fluid modifier 116 can be omitted or can be configured to have no effect on the size, shape, and/or length of the fluid pathway. For example, in some embodiments, the size and/or length of the secondary fluid pathway 110 and the main fluid pathway 108 are both static, and/or the size and/or length of the secondary fluid pathway 110 can be greater than the main fluid pathway 108, thereby delaying the delivery of liquid through the secondary fluid pathway 110 as compared to the main fluid pathway 108. The secondary fluid pathway 110 can include one or more additives that can be dispersed into the liquid flowing through the connector 100, with or without a fluid modifier 116 to disperse the one or more additives into the liquid.

In some embodiments, the connector 100 is configured to deliver or to infuse a specific and/or adjustable volume of medical fluid with the additive. In some embodiments, as also described elsewhere herein, this volume is controllable depending on the length, volume, or other dimensions of the secondary fluid pathway 110. In some embodiments, the connector is configured to distribute sufficient additive-infused liquid to fill or substantially fill the catheter to which it is attached. In some embodiments, the connector is selected and/or configured to provide a volume of additive-infused liquid that fills only a portion of the catheter (e.g., a portion of tubing external to the patient's body) and/or a volume insufficient to overflow out of the catheter into the patient. For example, the volume of additive-infused liquid to be emitted from the connector 100 can be configured to be less than or approximately equal to the interior fluid-carrying volume of the patient's catheter or less than or approximately equal to a portion of the patient's catheter that is configured to be positioned outside of the patient's body during use. In some embodiments, the volume of additive-infused liquid is less than or equal to about: 0.25 mL, 0.5 mL, 2 mL, 5 mL, 10 mL, 25 mL, values between the aforementioned values, ranges spanning those values, or otherwise. In some configurations, the connector can be configured to receive a volume sufficient to fill or overfill the catheter and/or to deliver a small amount of additive or the entire volume of additive infused liquid into the patient (e.g., when the additive is a medicament, etc.). In some embodiments, in a multistage configuration or other configuration, a volume of additive-infused liquid can be delivered from the connector, followed by an additive-free (or substantially additive-free) volume of medical fluid. In some embodiments, for example, where a therapeutic agent and locking agent are provided in a connector (or a series of connectors), the connector (or series) can be configured to deliver the therapeutic additive into the patient completely and to lock the catheter with the locking agent, which is retained or substantially retained in the catheter.

In some embodiments, the connector is configured to achieve one or more of the above-referenced volume distributions to the catheter when using any commercial catheter, including those selected from the group consisting of Hickman, Broviac, or Leonard tunneled catheters, including at least about 9 Fr or at least about 10 Fr Single or Double Lumen catheters, Double or Triple (e.g., red, blue, or white) Lumen catheters, at least about 12 Fr Double Lumen catheters, or at least about 12.5 Triple Lumen catheters. In some embodiments, the volume of additive-infused medical fluid distributed from (e.g., delivered out of) the connector is greater than or equal to about: 0.25 mL, 0.5 mL, 2 mL, 5 mL, values between the aforementioned values, ranges spanning those values, or otherwise. In some embodiments, the volume of additive-free medical fluid distributed from (e.g., delivered out of) the connector is greater than or equal to about: 0.25 mL, 0.5 mL, 2 mL, 5 mL, 10 mL, 25 mL, values between the aforementioned values, ranges spanning those values, or otherwise.

As also described in detail elsewhere herein, in some embodiments, at or near the termination of an infusion of medical liquid into the patient through the connector 100 (e.g., approximately at the point that the volume to be injected is achieved, the volume at which a plunger of a syringe used to infuse the fluid nears or reaches the terminal end of a syringe or bottoms out, at a point where the infusion is halted, etc.), the medical liquid in the secondary fluid pathway 110 exits the secondary fluid pathway 110 and passes through the fluid outlet 104. In some embodiments, this distribution of liquid from the secondary fluid pathway occurs automatically and/or without active manipulation of the connector by the user. In some embodiments, the medical fluid (e.g., the medical liquid without additive) and the additive-containing fluid (e.g., additive-infused liquid) mix at a location and/or time near or substantially at the end of the infusion of medical liquid through the connector 100 and/or form a locking solution at the fluid exit region 114 of the connector 100.

It is contemplated that any other embodiment that follows can include any feature, structure, component, material, step, or method of the connector 100 of FIG. 1, whether or not explicitly described and/or illustrated in such other embodiment for purposes of brevity. Nothing described or illustrated in connection with the connector 100 of FIG. 1 is required or essential or indispensable in connector 100 or in any other embodiment in this specification.

Figure 2A:
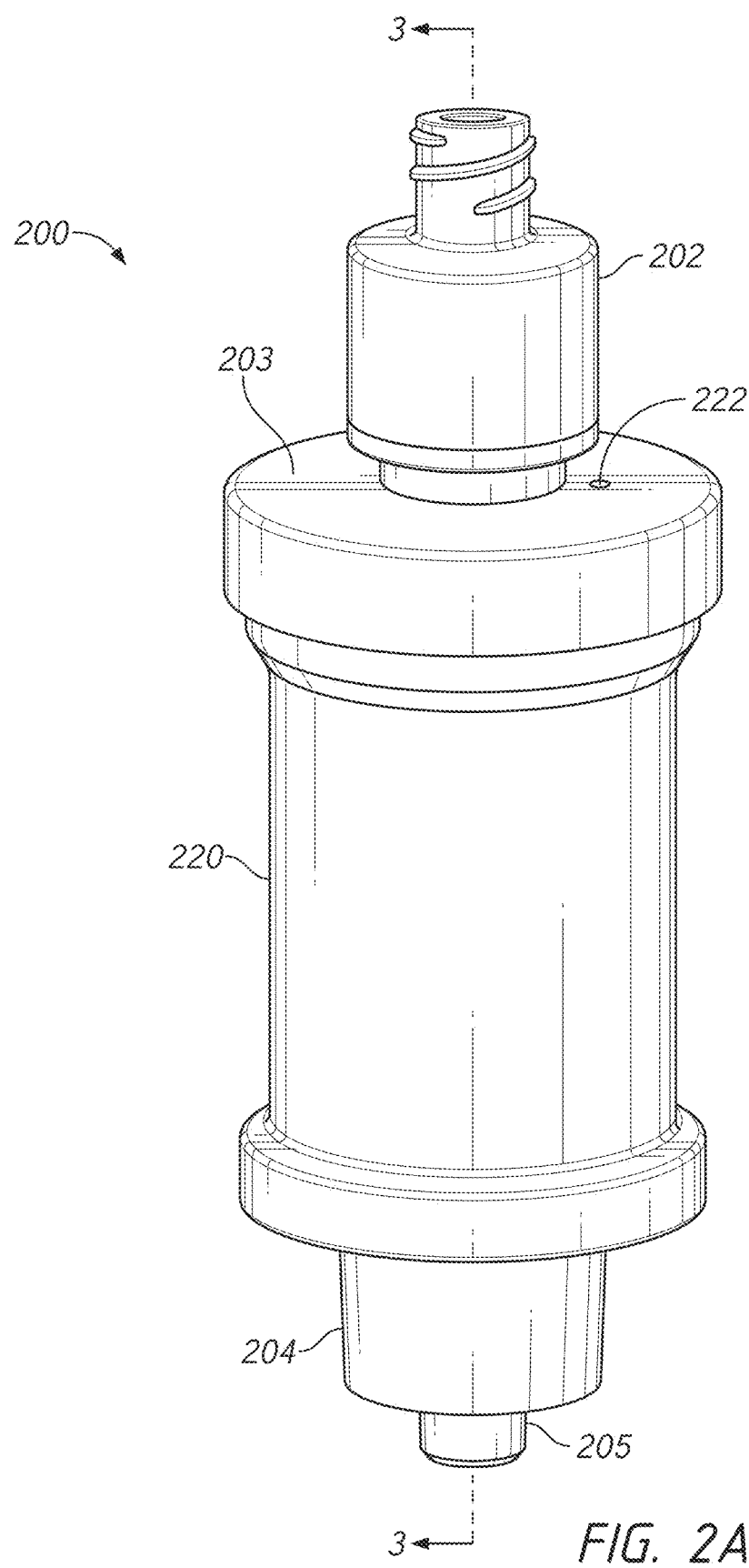
FIG. 2A is a front view of an example of a medical fluid connector of FIG. 1.

As illustrated in FIG. 2A, a connector 200 can include a fluid inlet 102 in the form of a first fluid-line attachment 202. The connector 200 can also include a cover cap 203, a housing 220, an air port 222, and a fluid outlet 104 in the form of a second fluid-line attachment 204. In some embodiments, the housing 220 can be formed of a rigid or substantially rigid material, such as polycarbonate. Either or both of the first or second fluid-line attachments can be closeable or resealable male or female connectors, such as a resealable female luer connector as the fluid inlet 202 and a resealable male luer connector with a male protrusion 205 as the fluid outlet 204, as shown. Any or all of the housing 220, the fluid guide 224, and/or the flexible carrier 232, and/or any other component or collection of components of the connector 200 can be made of, or can comprise a portion that is made of, a transparent or clear material to permit viewing of movement inside of the housing 220 or to permit viewing of liquid passing through the housing 220 or mixing with one or more additives inside of the housing 220. Any or all of the first fluid-line attachment 202, the housing 220, and the second fluid-line attachment 204 can be made of one or more rigid materials, such as polycarbonate or another form of plastic.

Figure 2B:
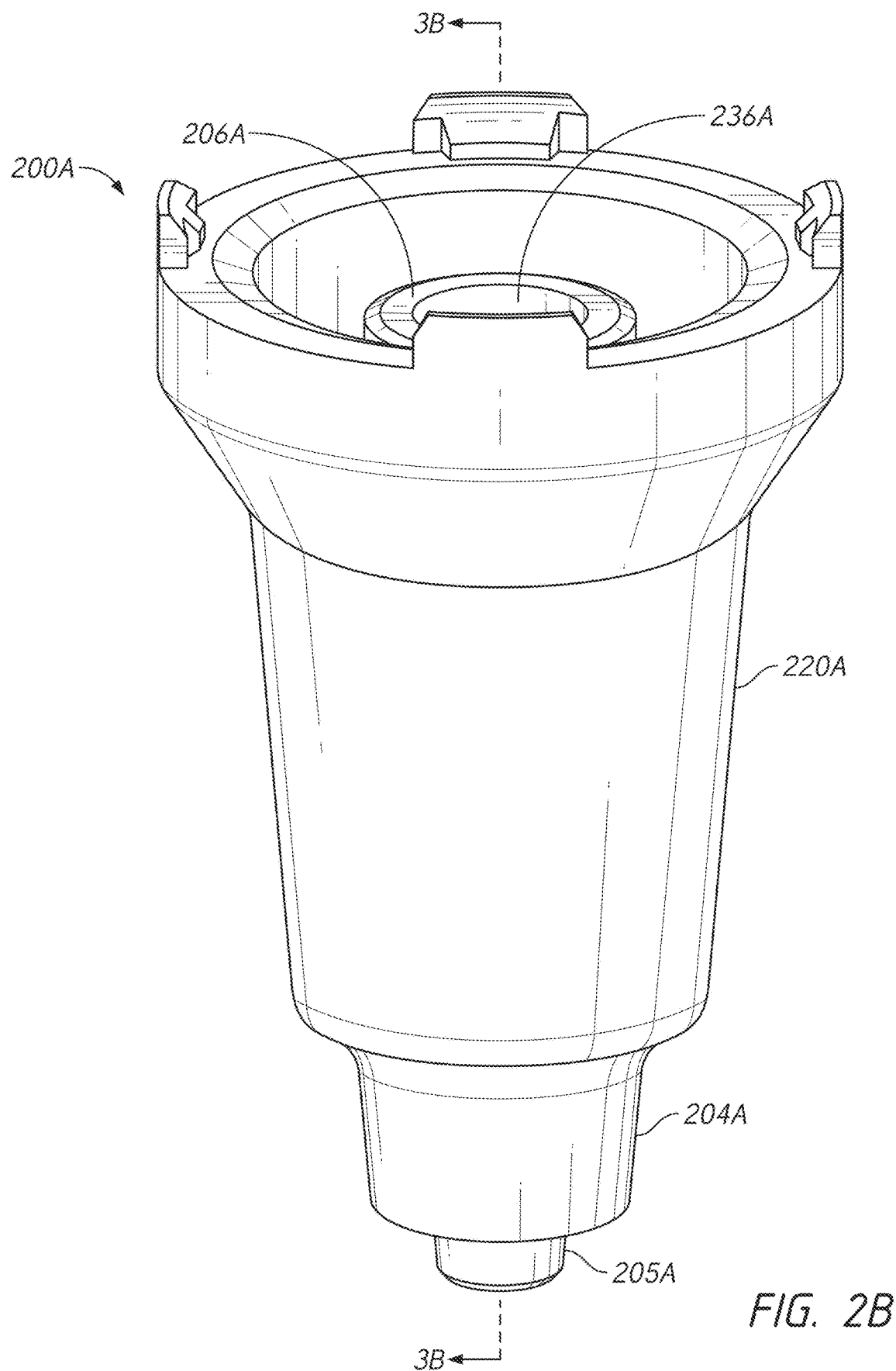
FIG. 2B is a front view of another example of a medical fluid connector of FIG. 1.
Figure 2C:
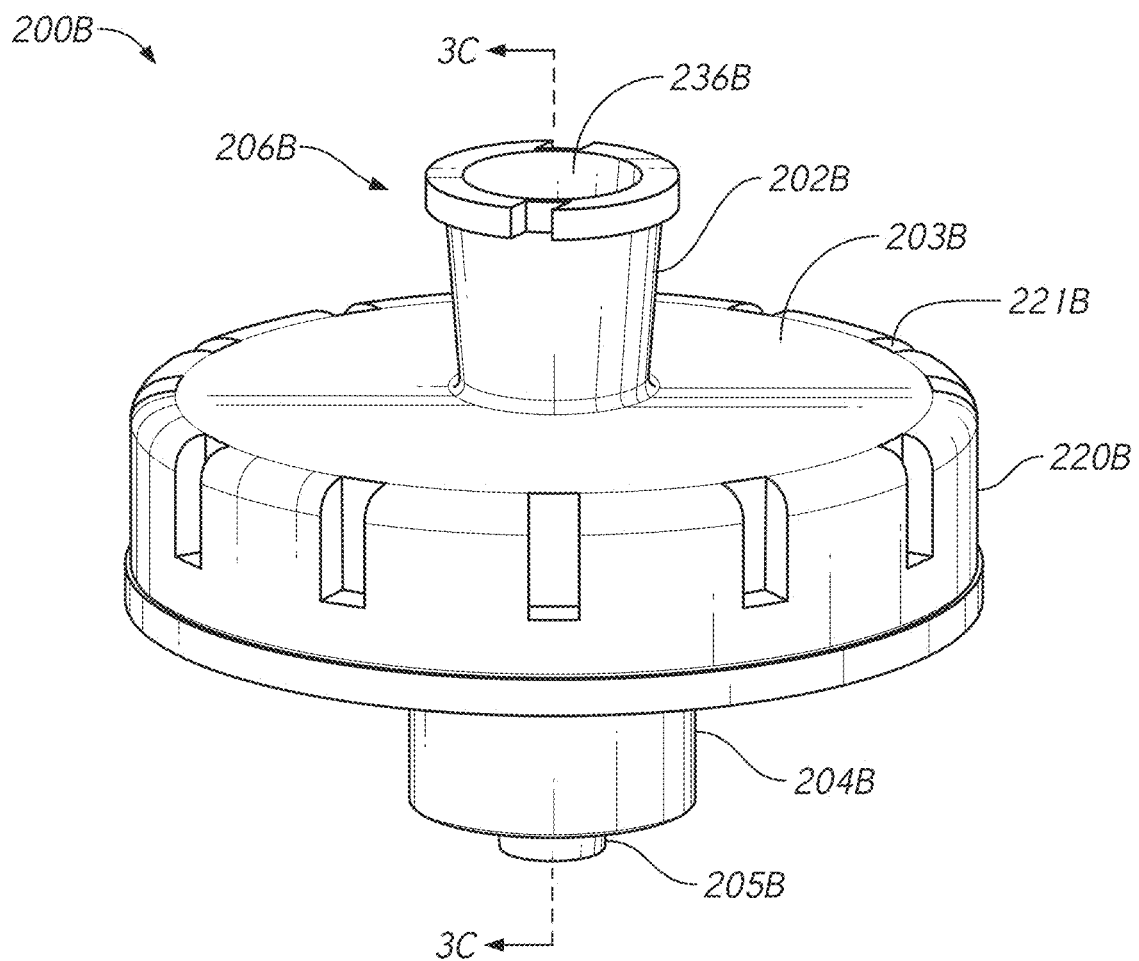
FIG. 2C is a front view of another example of a medical fluid connector of FIG. 1.
Figure 3A:
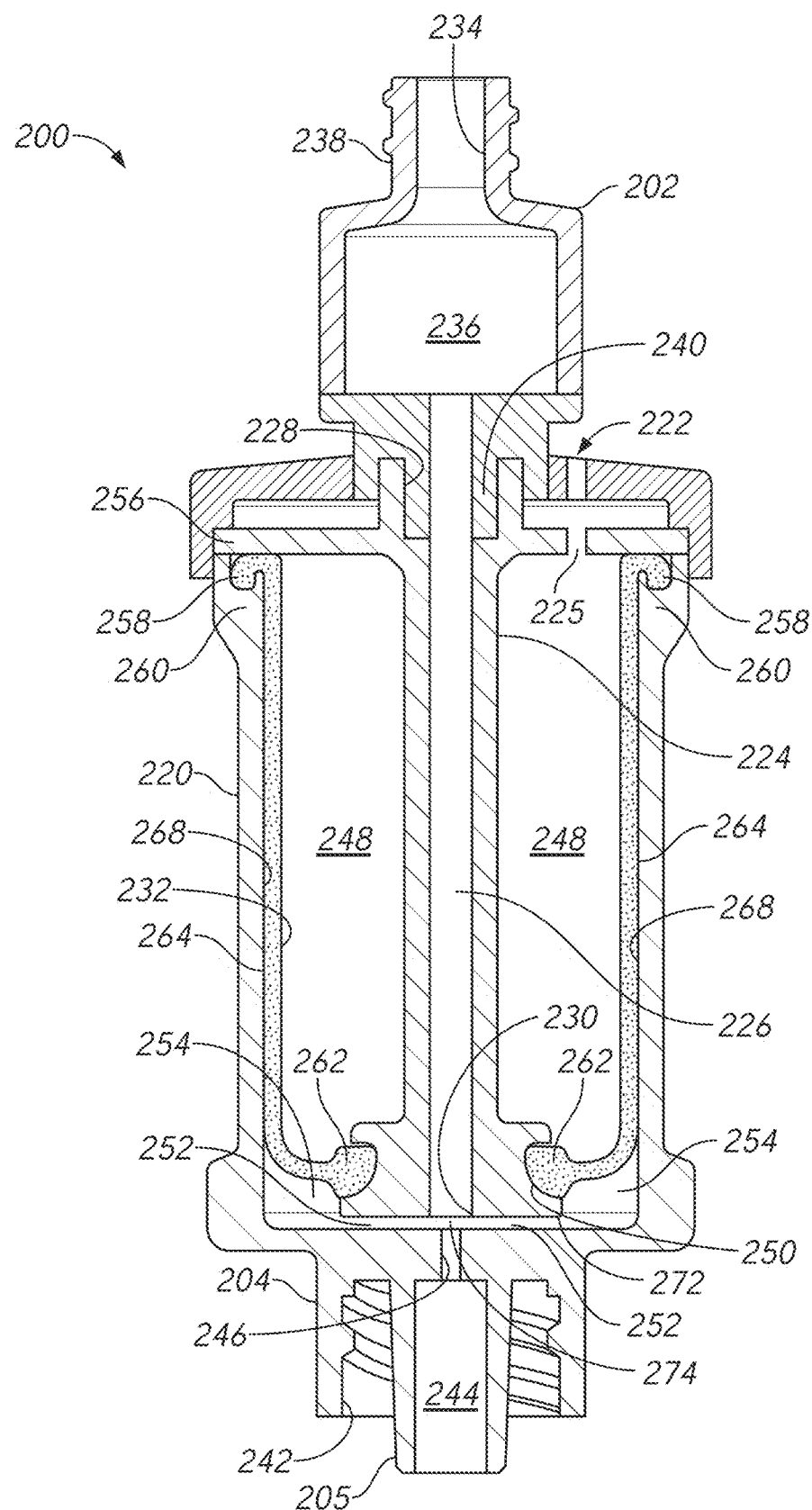
FIG. 3A is an example cross-sectional view of the medical fluid connector of FIG. 2A, taken along the line 3A-3A of FIG. 2A.

FIGS. 2B and 2C show other embodiments of medical connectors 200A, 200B. The embodiments of FIGS. 2B and 2C can include features that are the same as or that are different from features of the embodiment of FIG. 2A. FIG. 3A illustrates an example cross-section of the connector 200. FIGS. 3D-3E illustrate other example cross-sections of medical connectors 200C, 200D, although the connector 200C, 200D can have the same or substantially the same outer appearance as the connector 200 shown in FIG. 2A. The embodiments of FIGS. 3D-3F can include features that are the same as or that are different from features of the embodiment of FIGS. 2A and 3A. Any feature, structure, component, material, step, or method that is described and/or illustrated in one of FIGS. 2A-2C and 3A-3F can be used with or instead of any feature, structure, component, material, step, or method that is described and/or illustrated in any other embodiment in this specification. Similar features (e.g., fluid guides, internal fluid pathways, etc.) for different embodiments of the connectors are shown with coinciding numerical values but labeled with either a letter or a different letter (e.g., no letter for connector 200, the letter "A" for connector 200A, and the letter "B" for connector 200B, the letter "C" for connector 200C, and the letter "D" for connector 200D). For example, comparing the embodiment of FIG. 2A to the embodiment of FIG. 2B, the housing 220 of the connector 200 in FIG. 2A coincides to the housing 220A of the connector 200A in FIG. 2B. Likewise, comparing the embodiment of FIG. 2A or 2B to the embodiment of FIG. 2C, the housing 220 of the connector 200 in FIG. 2A or the housing 220A of the connector 200A in FIG. 2B coincides to the housing 220B of the connector 200B in FIG. 2C.

Figure 3B:
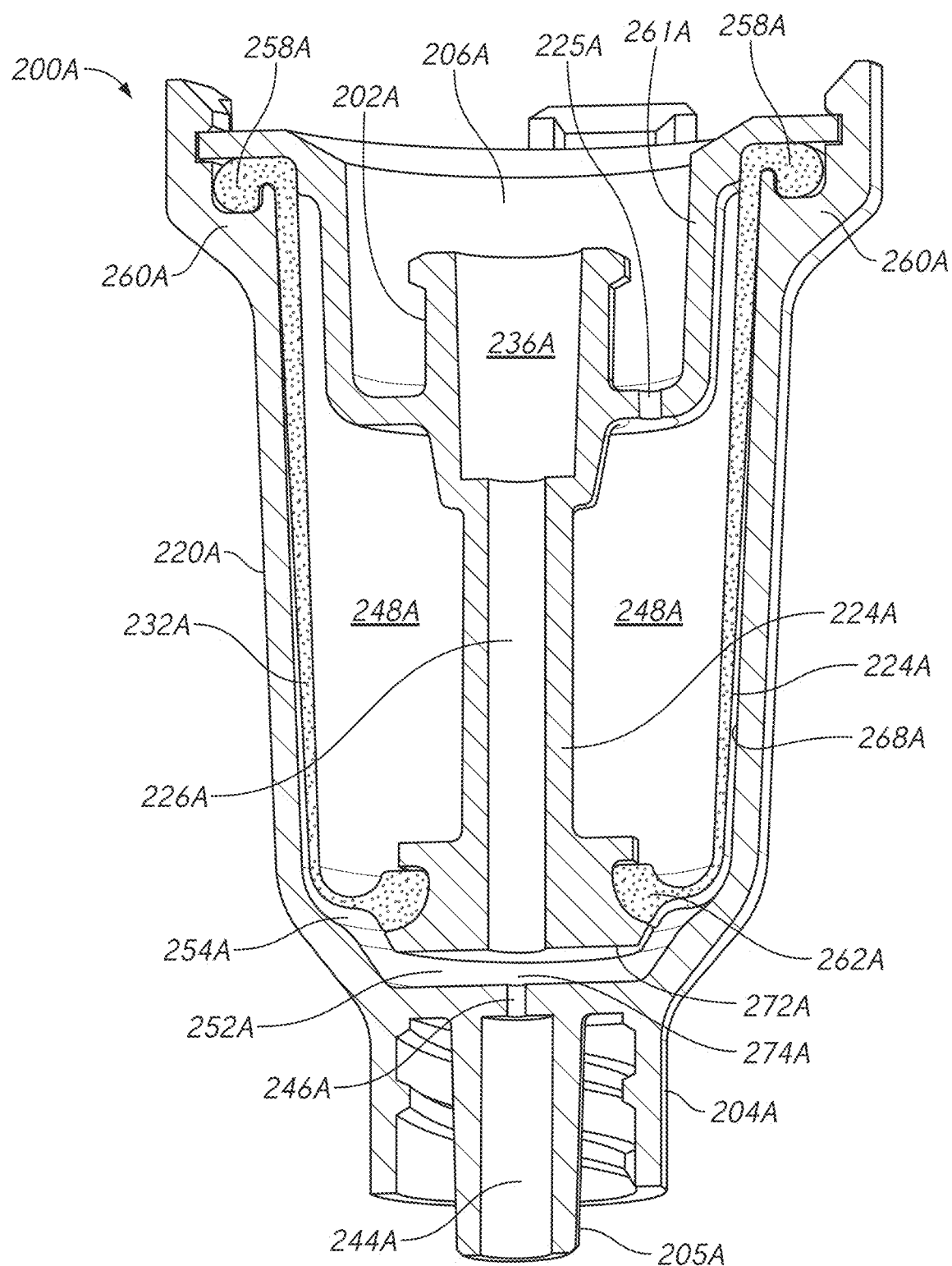
FIG. 3B is a cross-sectional view of the medical fluid connector of FIG. 2B, taken along the line 3B-3B of FIG. 2B.
Figure 3C:
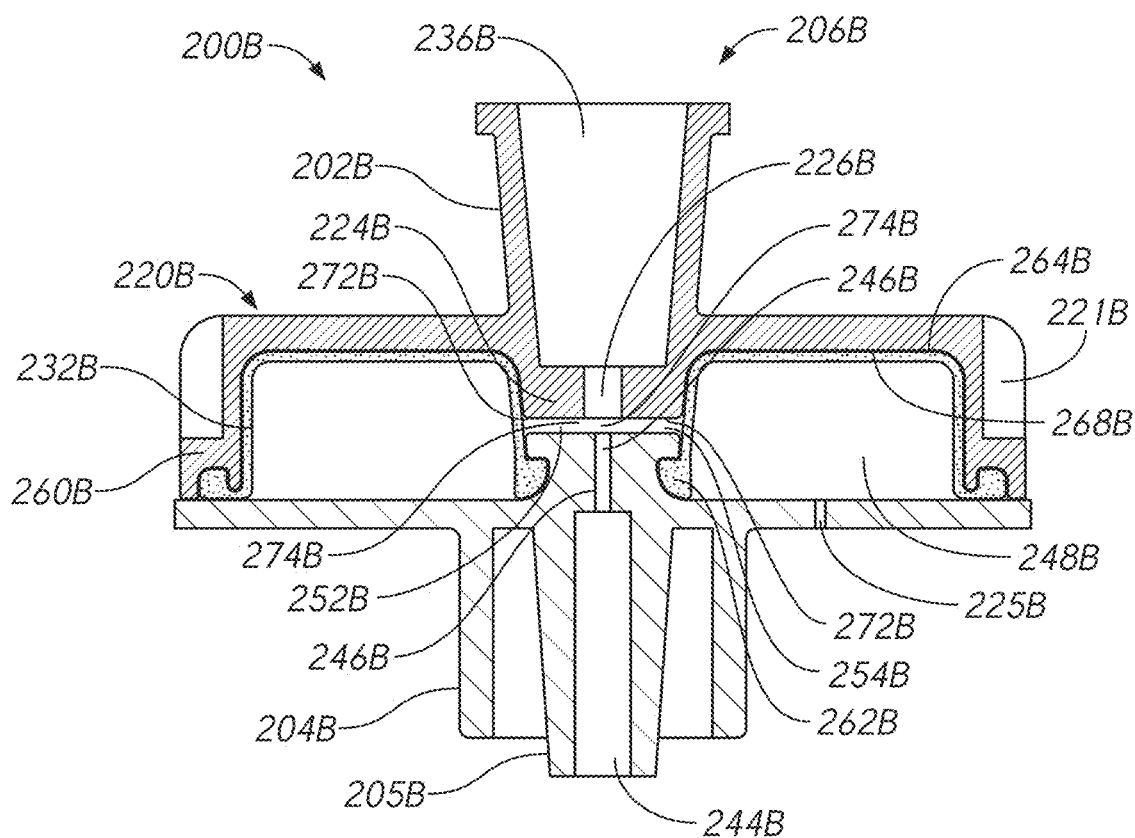
FIG. 3C is a cross-sectional view of the medical fluid connector of FIG. 2C, taken along line 3C-3C of FIG. 2C.
Figure 3D:
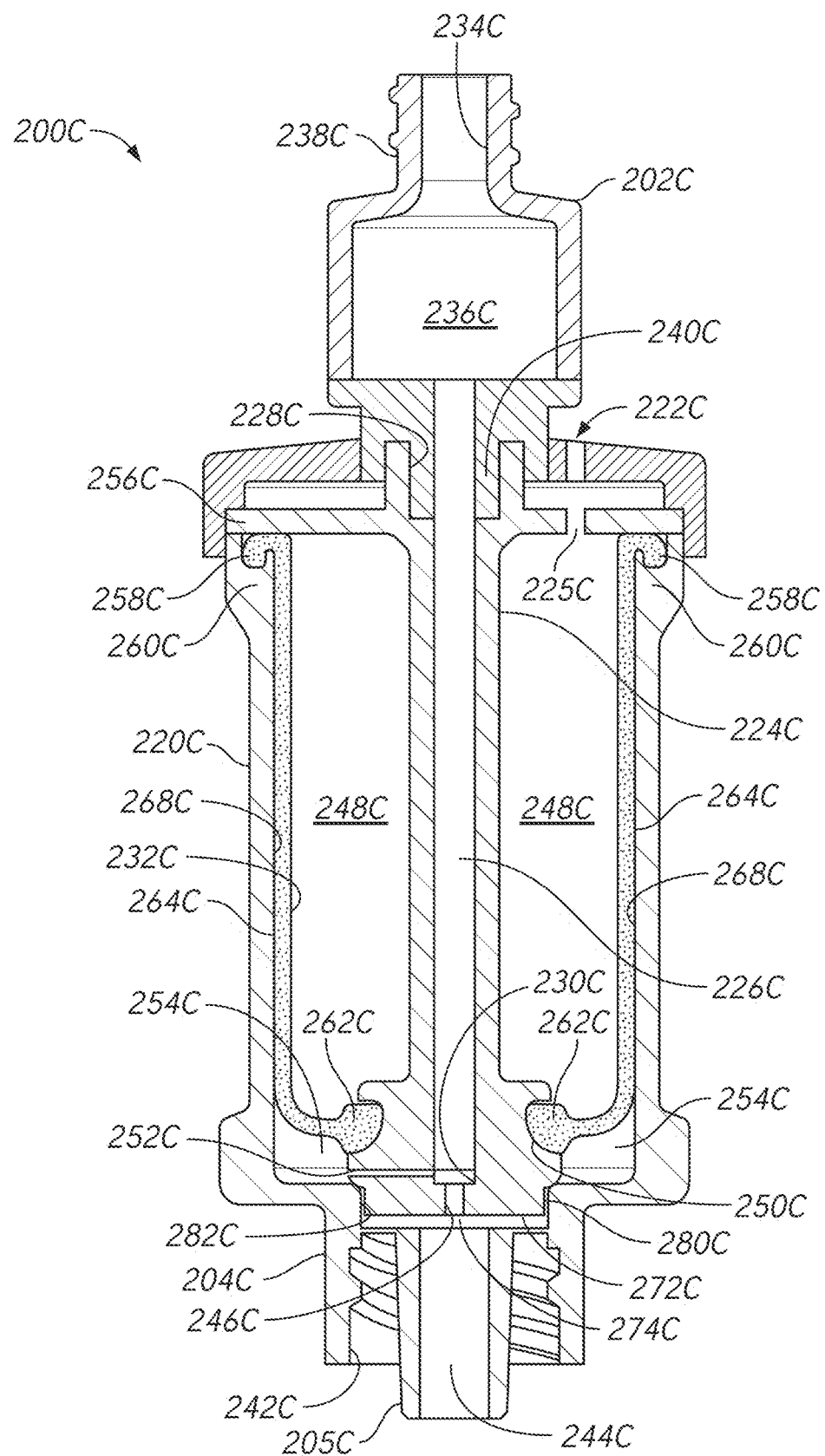
FIG. 3D is another example cross-sectional view of the medical fluid connector of FIG. 2A, taken along the line 3A-3A of FIG. 2A.
Figure 3E:
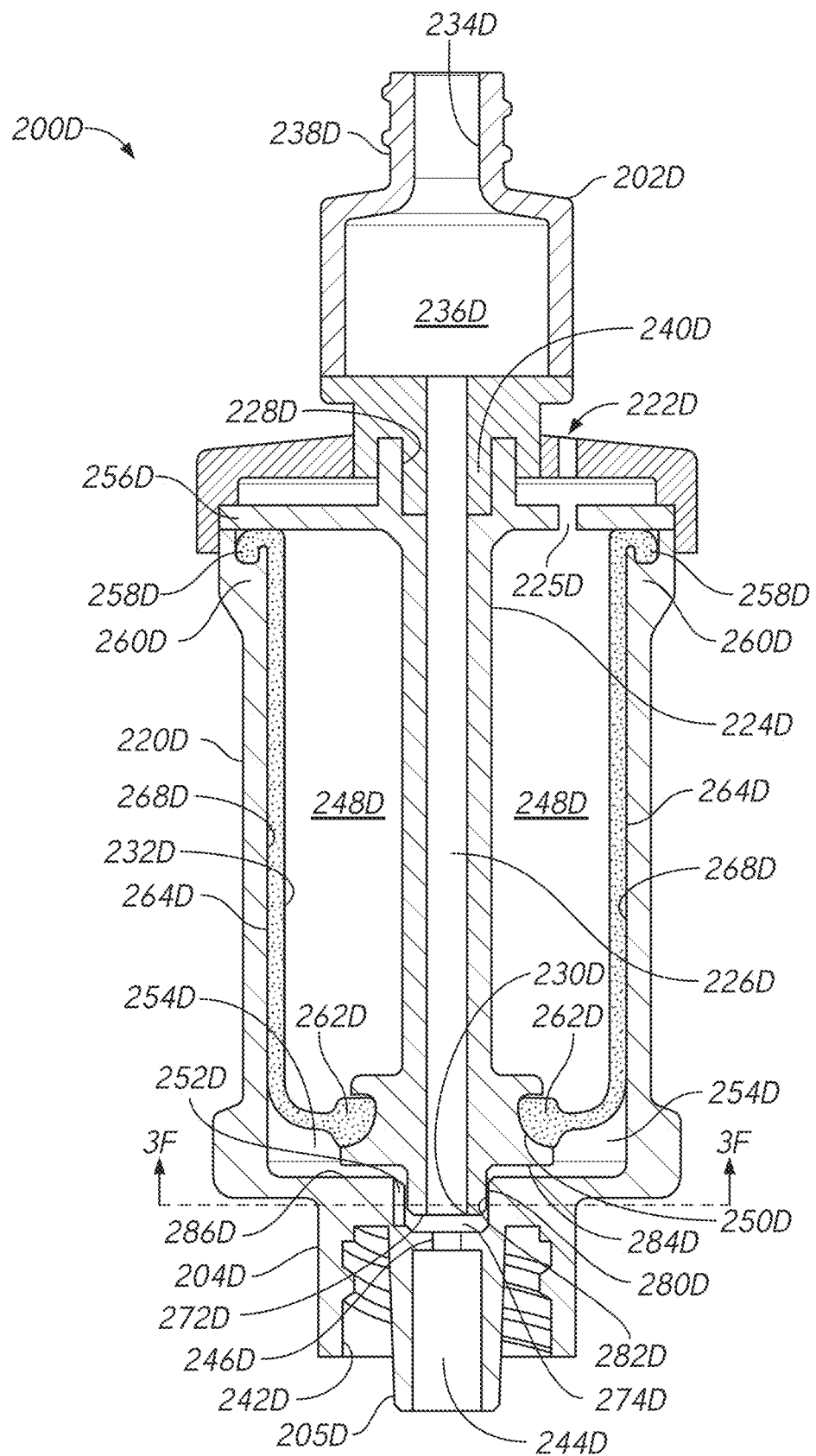
FIG. 3E is another example cross-sectional view of the medical fluid connector of FIG. 2A, taken along the line 3A-3A of FIG. 2A.
Figure 3F:
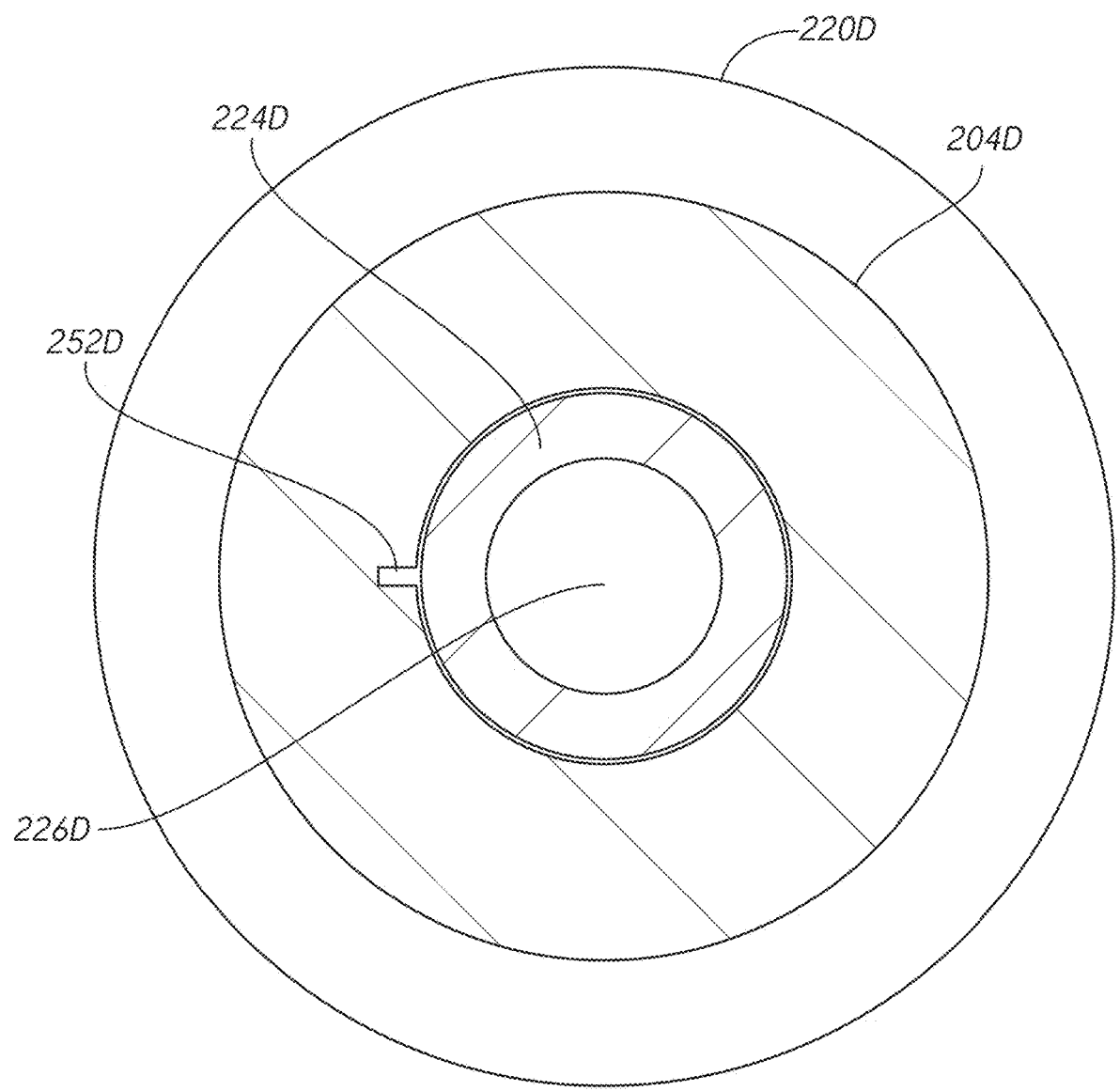
FIG. 3F is a cross-sectional view of the medical fluid connector of FIG. 3E, taken along the line 3F-3F of FIG. 3E.

For brevity, not every feature of the connector 200A of FIG. 3B, the connector 200B of FIG. 3C, the connector 200C of FIG. 3D, or the connector 200D of FIGS. 3E-3F are numerically indicated, though certain features of the connector 200A, 200B, 200C, or 200D are apparent by comparing it with the connector 200 of FIG. 3A and such features form part of the disclosure of FIGS. 3B-3F. In addition, just as the embodiments of FIGS. 3A-3F can have features that are the same or substantially the same, those embodiments can include one or more features that are different, as shown or otherwise. It should be appreciated that different features of the embodiments of FIGS. 3A-3F are for illustration only, and as disclosed elsewhere herein, any feature, structure, or component that is described and/or illustrated in one embodiment in this specification can be used with or instead of any feature, structure, or component that is described and/or illustrated in any other embodiment in this specification. Additionally, one or more of the features described for the illustrative embodiments herein can be excluded from other embodiments.

Figure 4:
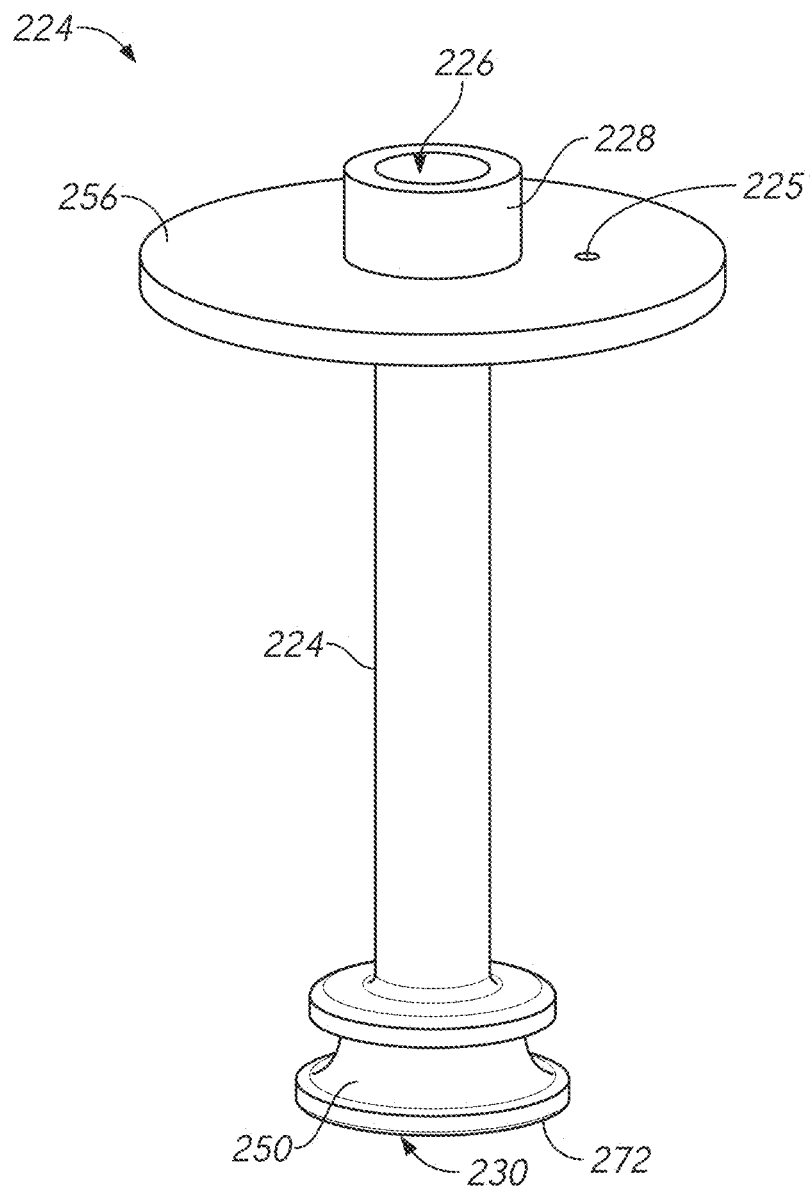
FIG. 4 is a front view of an internal fluid guide from the medical fluid connector of FIG. 2A.

As illustrated in FIG. 3A, an interior region of the connector 200 can comprise multiple components, including a fluid guide 224 with a proximal fluid port 228, a proximal cover region 256 (e.g., with a vent 225 (see also FIG. 4)), an internal fluid pathway 226, a distal fluid port 230 (see also FIG. 4), and a distal attachment region 250 (see also FIG. 4); and a fluid modifying region 254 and a fluid modifier 116 in the form of a flexible carrier 232 with an internal region 248. In some embodiments, as shown, the fluid modifier 116 can be held in place at a plurality of points or regions inside of the connector 100. For example, a proximal edge 258 of the flexible carrier 232 can be securely held between an upper region 260 (e.g., forming a lip, a projection, a barb, etc.) of the housing 220 and an underside of the outer edge of the cover region 256 of the fluid guide 224; and a distal end region 262 of the flexible carrier 232 can be securely held circumferentially in a fluid-tight manner in the distal attachment region 250 of the fluid guide 224, such as by forming a distal opening in the flexible carrier 232 that is slightly smaller than the outer circumference of the distal attachment region 250, causing the distal opening to exert a radially inwardly directed restoring force which tightly grips the distal attachment region 250 of the fluid guide 224. As shown, each of the connectors 200, 200A, 200B, 200C, 200D can be formed as a single integrated connector with any combination or all of the parts illustrated in the figures or described in the text permanently and non-removably attached to each other, and not configured to be attached together or removed from each other by a user in the normal course of use. Of course, in some embodiments, any components or combinations of components can be removable or attachable from each other by a user in suitable configurations, such as in modular configurations with different types of fluid modifiers that can be combined with different types of connector components. As illustrated in some embodiments, each of the connectors 200, 200A, 200B, 200C, 200D can be needle-free or needle-less or spike-less, without requiring an exposed metal or plastic needle or spike to pierce or penetrate a septum or seal or other structure to enable fluid flow.

As shown in FIGS. 3A, 3D, and 3E, the first fluid-line attachment 202, 202C, 202D can comprise an internal fluid channel 236, 236C, 236D that comprises a proximal female end 238, 238C, 238D (which in some embodiments can include an ISO 594-compliant luer taper) with a male-receiving region 234, 234C, 234D, and a male end 240, 240C, 240D that is coupled to the proximal fluid port 228, 228C, 228D of the fluid guide 224, 224C, 224D. In some embodiments, as shown in FIGS. 3A, 3D, and 3E, the proximal female end 238, 238C, 238D can be threaded. In some embodiments, the proximal female end is not threaded. The second fluid-line attachment 204, 204C, 204D can comprise an internal fluid channel 244, 244C, 244D, an internally threaded shroud 242, 242C, 242D, and a male luer protrusion 205, 205C, 205D (which in some embodiments can include an ISO 594-compliant luer taper). In some embodiments, the internal fluid pathway 226, 226C, 226D can have an internal diameter that is smaller than an internal diameter of the proximal internal fluid channel 236, 236C, 236D and/or an internal diameter of the internal fluid channel 244, 244C, 244D. In some embodiments, as shown in FIG. 3C, any shroud provided herein can lack threading or, as shown in FIG. 3B, any shroud provided herein can include threading. In some embodiments, any of the inlet or outlet adaptors (male or female) and shrouds disclosed herein can include threading or lack threading. In some embodiments, as shown in the connector 200, 200C, 200D, the main fluid pathway 108 can be provided in the form of the combination of the internal fluid channel 236, 236C, 236D of the first fluid-line attachment and the internal fluid pathway 226, 226C, 226D of the fluid guide 224, 224C, 224D. In some embodiments, either or both of the first or second fluid-line attachments 202, 202C, 202D, 204, 204C, 204D can comprise closeable, resealable, and/or swabbable medical fluid connectors.

As shown in FIG. 3B, in some embodiments, instead of a male connection, the connector 200A can include a fluid inlet 102 comprising a first fluid-line attachment 202A and a female luer connector 206A. In some embodiments, as shown in FIG. 3B, the female luer connector 206A can include a male-receiving region 236A configured to receive a male protrusion (which in some embodiments can include an ISO 594-compliant luer taper). In some embodiments, the fluid inlet 102 is recessed as shown in FIG. 3B. As shown, a recessed fluid-line attachment 202A can be disposed wholly within the connector and/or not protruding from the connector. In some embodiments, not shown, the fluid line attachment can be partially disposed in and/or partially protruding or exposed from the connector. Having a recessed fluid inlet 102 makes the connector 200A advantageously compact while still offering ease of manipulation by a user (e.g., providing a large area on the side of the connector for grasping between a finger and the thumb, allowing rotation and manipulation of the connector, for instance). In some embodiments, the recessed configuration facilitates bulk storage and/or transport of the connectors. In some embodiments, for example, the connectors 200A can be connected serially (e.g., end-to-end) and stored. As also disclosed elsewhere herein, serial connection or other connection of multiple connectors can advantageously be used to infuse more than one additive at a time. For instance, in some embodiments, where connectors are attached serially, each connector 200A in a series can comprise a different therapeutic and/or chemical agent. In some embodiments, during infusion of a medical fluid through serially linked connectors, different agents can be infused at once (e.g., with one infusion of medical fluid). In some embodiments, different connector configurations can be connected serially, in parallel, or in any other way to provide a desired additive infusion profile. The recessed configuration is also less bulky when in use, lowering chances that the connector is inadvertently contacted after insertion of the catheter into a patient, increasing the comfort level of the patient.

In some embodiments, as shown in FIG. 3B, the recessed fluid inlet provides a receptacle 261A configured to receive a shroud of, for example, a syringe or another connector having a male luer fitting. In some embodiments, the receptacle 261A is configured to snuggly receive an interfacing shroud (e.g., is snug-fit). In some embodiments, the snug fitting within the receptacle provides added strength and/or stability to the connection between the coupling features. In some embodiments, this strength and/or stability can beneficially prevent movement, bending, or breakage of the coupled components. In some embodiments, interaction between the receptacle 261A and a shroud of a coupled device also provides stability in configurations where multiple connectors are attached serially by, for instance, preventing or substantially lowering the amount of movement between attached components (e.g., reducing bending, etc.).

In some embodiments, the connector has a length measured generally from a first end (e.g., from the inlet 102) to a second end (e.g., to the outlet 104) along the direction of fluid flow. In some embodiments, the connector also has a diameter measured across the connector transverse to the direction of fluid flow from a first side of the connector to a second side laterally (e.g., extending radially outward from the fluid pathway). In some embodiments, this diameter of the connector can be greater than an outer diameter of the fluid inlet and/or the fluid outlet. In some embodiments, this diameter can improve ease of gripping of the connector between fingers of a user.

As shown in FIGS. 3A, 3B, 3D, and 3E, in some embodiments, the length of the connector can be greater than the diameter (or equal to or greater than the diameter). As shown in FIG. 3C, in some embodiments, the diameter can be greater than the length of the connector (or greater than or equal to the length).

In some embodiments, as also described elsewhere herein, having a length greater than the width of the connector also allows the user to easily grasp the connector and align it with the catheter during placement, replacement, or manipulation of the connector. In some embodiments, having a diameter greater than or equal to the length facilitates bulk storage and/or transport of the connectors. For example, as also described elsewhere herein, the connectors can be connected serially and stored or used (e.g., to infuse more than one additive or to infuse a greater quantity of additive). In some embodiments, in configurations where the diameter is greater than or equal to the length of the connector, serial or parallel connection and disconnection of the connectors is facilitated because the lateral sides of the connector protrude from the inlet and outlet portions of the connector, allowing easier access to and manipulation of individual connectors.

As shown in FIG. 3C, in some embodiments, any of the connectors disclosed herein can comprise traction features 221B to facilitate manipulation (e.g., placement, twisting, movement, etc.) of the connectors. For example, as shown in FIG. 3C, the connector 200B can comprise grips 221B (e.g., roughenings, knurlings, traction pads, dimples, protrusions, ribs, etc.) around the periphery or portion of the periphery of the exterior of the connector 200B.

As shown in FIG. 3C, in some embodiments, the connector 200B can include a fluid inlet 102 comprising a first fluid-line attachment 202B and a female luer connector 206B. As shown, the fluid inlet can lack a shroud. In some embodiments, as shown in FIG. 3C, the female luer connector 206B can include a male-receiving region 236B configured to receive a male protrusion (which in some embodiments can include an ISO 594-compliant luer taper). In some embodiments, the fluid outlet of the connector 200B comprises a second fluid-line attachment 204B. In some embodiments, the second fluid-line attachment comprises one or more of an internal fluid channel 244B, a shroud 242 (e.g., a non-threaded shroud), and a male luer protrusion 205B (which in some embodiments can include an ISO 594-compliant luer taper). In some embodiments, the fluid outlet 104 lacks a shroud.

In some embodiments, the flexible carrier can be placed in an orientation that allows it to deform towards different portions of the connector 200, 200A, 200B, 200C, 200D. For example, in the embodiments of FIGS. 3A, 3B, 3D, and 3E, the flexible carrier 232, 232A, 232C, 232D is configured to deform upwardly and in a lateral direction that is towards the internal fluid pathway 226, 226A, 226C, 226D. In FIG. 3C, the flexible carrier 232B configured to deform downwardly and laterally in a direction that is towards the housing 220B. In other embodiments, not shown, the flexible carrier can be placed in a position to deform in a direction towards the proximal end of the connector, or otherwise.

In some embodiments, such as shown in the embodiments of FIGS. 3A, 3D-3F, and 6A-9, the upwardly deforming configuration can advantageously utilize gravity as an additional restoring force when expelling the additive-infused liquid into the catheter. In other words, gravity (in addition to or instead of the elastic force of the fluid modifier) can provide a restoring force, pushing the additive-infused fluid out of the fluid modifying region. In some embodiments, as shown in FIGS. 3C and 10-13, a downwardly deforming configuration (e.g., where the fluid contacting the flexible carrier enters at an upper portion of the flexible carrier and pushes the flexible carrier downward as the flexible carrier is deformed) can advantageously utilize gravity as an additional deforming force when infusing the medical liquid into the catheter. In other words, gravity (in addition to flow force of the fluid) can push against the flexible carrier, deforming it, and allowing infusion of the medical fluid with the additive. In some embodiments, during infusion, the user can manipulate the orientation of the connector (e.g., by holding it so the outlet faces upwardly or downwardly) to allow gravity to either or both aid in the deformation or restoration of the flexible carrier.

In some embodiments, such as shown in the embodiment of FIG. 3C, the flexible carrier can be shaped in a manner that itself resists deformation. For example, the flexible carrier 232B of the embodiment of FIG. 3C is cross-sectionally arch-shaped or substantially arch-shaped. The restorative force of one or more resiliently-shaped configurations (arch-shaped, arc-shaped, semi-circular, etc.) can advantageously provide additional restorative force to expel the additive-infused liquid from the fluid modifying region 254B.

As illustrated, in some embodiments, the first diversion region 111 of the embodiment of FIG. 1 can be provided in the connector 200, 200A, 200B, 200D in the form of a plurality of alternative fluid pathways in the region between a distal end of the fluid guide 224, 224A, 224B, 224D and a constriction or diverter or divider 246, 246A, 246B, 246D, or near a distal end of the fluid guide 224C, with a diverter or divider 246C located proximal to the transitional region 274C. In some embodiments, the diverter or divider 246, 246A, 246B, 246C, 246D can comprise an opening that is narrower than the fluid pathway 226, 226A, 226B, 226C, 226D within the fluid guide 224, 224A, 224B, 224C, 224D. In some embodiments, the diverter or divider 246, 246A, 246B, 246C, 246D can include a constriction (such as shown in FIG. 3A-3E), a manifold, a valve, or any other structure that can allow some but not all of the fluid from the fluid pathway 226, 226A, 226B, 226C, 226D to pass to the internal flow channel 244, 244A, 244B, 244C, 244D. The change in cross-sectional width between the fluid pathway 226, 226A, 226B, 226C, 226D within the fluid guide 224, 224A, 224B, 224C, 224D and the opening in the diverter or divider 246, 246A, 246B, 246C, 246D can cause some of the liquid that is passing through connector 200, 200A, 200B, 200C, 200D to be diverted laterally into a lateral fluid region 252, 252A, 252B, 252C, 252D and then upwardly or downwardly into a fluid-modifying region 254, 254A, 254B, 254C, 254D such as a variable-volume fluid-modifying region 254, 254A, 254B, 254C, 254D between an interior wall 268, 268A, 268B, 268C, 268D of the housing 220, 220A, 220B, 220C, 220D and an exterior wall 264, 264A, 264B, 264C, 264D of the fluid modifier 116.

As shown in FIGS. 3A-3C, the transitional region 274, 274A, 274B can be located distal to the distal fluid port 230, 230A, 230B. The transitional region 274, 274A, 274B can include a gap separating a proximal end of the diverter or divider 246, 246A, 246B and a distal end 272, 272A, 272B of the fluid guide 224, 224A. The diverter or divider 246, 246A, 246B can be located distal to the transitional region 274, 274A, 274B. The transitional region 274, 274B in FIGS. 6A and 10 respectively can include the proximal opening of the diverter or divider 246, 246B and the lateral opening where the portion of the medical liquid 266, 266B is diverted laterally, and/or the space or volume located between these locations or structures. The lateral fluid region 252, 252A, 252B can extend radially and/or generally transverse to the fluid pathway 226, 226A, 226B.

As shown in FIG. 3D, the diverter or divider 246C can be proximal to the transitional region 274C and can extend distally from the distal fluid port 230C to the transitional region 274C. The fluid guide 224C can have an outer surface 280C near the distal end 272C of the fluid guide 224C to interface with an inner surface 282C of the housing 220C near a proximal end of the second fluid-line attachment 204C. The interface can be impermeable to liquid such that liquid cannot pass through between the outer surface 280C and the inner surface 282C (for example, via a tight fit at the interface). The lateral fluid region 252C can be located near or at the distal fluid port 230C. The lateral fluid region 252C can extend generally transversely from the fluid pathway 226C to the variable-volume fluid-modifying region 254C and can comprise a generally uniform cross-section. In some embodiments, the cross-section of the lateral fluid region 252C can be generally circular.

The opening in the diverter or divider 246C can have a greater cross-sectional area than the lateral fluid region 252C. In some embodiments, the cross-sectional area of the opening in the diverter or divider 246C can be about four times that of the lateral fluid region 252C. In some embodiments, the opening in the diverter or divider 246C can have a greater internal diameter or width than the lateral fluid region 252C. In some embodiments, the internal diameter of the opening in the diverter or divider 246C can be at least about two times that of the lateral fluid region 252C. In some embodiments, the internal diameter of the opening in the diverter or divider 246C can be about 0.032" and the internal diameter of the lateral fluid region 252C can be about 0.016".

As shown in FIG. 3E, the diverter or divider 246D can be located distal to the transitional region 274D so that the internal flow channel 244D extends distally from the diverter or divider 246D. The fluid guide 224D can have an outer surface 280D near the distal end 272D of the fluid guide 224D to interface with an inner surface 282D of the housing 220D near or at the proximal end of the second fluid-line attachment 204D. The interface can be liquid impermeable such that liquid cannot pass through between the outer surface 280D and the inner surface 282D (for example, via a tight fit at the interface). As shown in FIGS. 3E and 3F, the lateral fluid region 252D can be located to a lateral side of the transitional region 274D. The lateral fluid region 252D can be in fluid communication with the transitional region 274D at a distal end of the fluid region 252D, and can extend generally parallel to the fluid pathway 226D from the transitional region 274D to the variable-volume fluid-modifying region 254D. As shown in FIG. 3E, the variable-volume fluid-modifying region 254D can include a portion between a distal end 286D of the fluid-modifying region 254D and a shoulder 284D of the fluid guide 224D. The lateral fluid region 252D can be in fluid communication with fluid-modifying region 254D at a location within this portion. In some embodiments, such as shown in FIGS. 3E and 3F, the lateral fluid region 252D can be adjacent the outer surface 280D near the distal end 272D of the fluid guide 224D. In other embodiments, the lateral fluid region can be located more laterally, with a tunnel connecting the lateral fluid region and the transitional region 274D.

The lateral fluid region 252D can have a generally uniform cross-section. As shown in FIG. 3F, the lateral fluid region 252D can have a generally rectangular cross-section. In other embodiments, the cross section of the lateral fluid region 252D can have other shapes, such as semicircular, triangular, or others. The diverter or divider 246D can have an opening with a greater cross-sectional area than the lateral fluid region 252D. In some embodiments, the cross-sectional area of the opening in the diverter or divider 246D can be about four times that of the lateral fluid region 252D. In some embodiments, the opening in the diverter or divider 246D can have a greater internal dimension than the lateral fluid region 252D. In some embodiments, the internal diameter of the opening in the diverter or divider 246D can be greater than a width of the cross-section of the lateral fluid region 252D. In some embodiments, the internal diameter of the opening in the diverter or divider 246D can be about 0.032" (resulting in a cross-sectional area of about 0.0008 square inch) and the lateral fluid region 252C can have cross-sectional dimensions such as 0.020"×0.010", or any other dimensions resulting in a cross-sectional area of about 0.0002 square inch.

In some embodiments, such as shown in FIG. 3A, at least a portion of the fluid modifying region 254 can be created by a separation or by an increase in distance between the flexible carrier 232 and another component of the connector 200, such as an inner wall 268 of the connector 200, producing a variable volume into which liquid can flow. The secondary fluid pathway 110 of the embodiment of FIG. 1 can be provided in the connector 200, 200A, 200B, 200C, 200D of FIGS. 3A-3F in the form of the lateral fluid region 252, 252A, 252B, 252C, 252D and the fluid-modifying region 254, 254A, 254B, 254C, 254D, such as describedelsewhere herein. As illustrated in FIGS. 7-9 and FIGS. 11-13, the size or volume of the secondary fluid pathway 110 in the connector 200 (or 200C, 200D), 200B (or connector 200A, not shown) can be variable over time or variable as a function of the volume of fluid that has been infused into and/or out of the connector 200 (or 200C, 200D), 200B. In some embodiments, as shown in FIGS. 3A-3E and 6-13, the fluid modifier 116 is a flexible carrier. In some embodiments, the fluid modifier 116 is a structure or device that does not significantly bend or flex to change the volume or direction of the fluid flow path, but instead merely permits an additive to be emitted or eluted or leached out into the fluid flow path, such as by dissolving into the fluid or releasing into the fluid or permitting the fluid to flow in, through, or around the fluid modifier 116 while the fluid modifier 116 itself remains essentially or entirely static.

In some embodiments, the connector comprises a fluid pathway with at least a portion that has a completely or at least substantially unobstructed pathway (e.g., through the entirety of the connector). For instance, while the constriction or diverter or divider 246, 246A, 246B, 246C, 246D can divert a portion of the medical fluid from the primary fluid path, a portion of fluid can travel directly through the opening in the diverter or divider or constriction unimpeded 266 (or 266C, 266D), 266B (as shown in FIGS. 6A-13). In some embodiments, the medical connector is configured to allow at least a portion of the medical fluid to travel through it uninterrupted in a straight or substantially straight pathway and devoid (or substantially devoid) of additive. In some embodiments, as shown in FIGS. 3A-3E, the variable-volume fluid-modifying region 254, 254A, 254B, 254C, 254D is in fluidic communication with the fluid guide 224, 224A, 224B, 224C, 224D, the opening in the constriction or diverter or divider 246, 246A, 246B, 246C, 246D, and/or the internal fluid channel 244, 244A, 244B, 244C, 244D. Thus, while some embodiments can achieve certain objectives disclosed herein using a valve (e.g., to divert at least a portion of fluid into, for instance, a secondary fluid pathway of FIG. 1), in other embodiments, the connector lacks a valve. In some embodiments, the infusion of additive containing fluid into the catheter happens by virtue of the elasticity of the flexible carrier, automatically and without additional infusion steps taken by a user.

Figure 5:
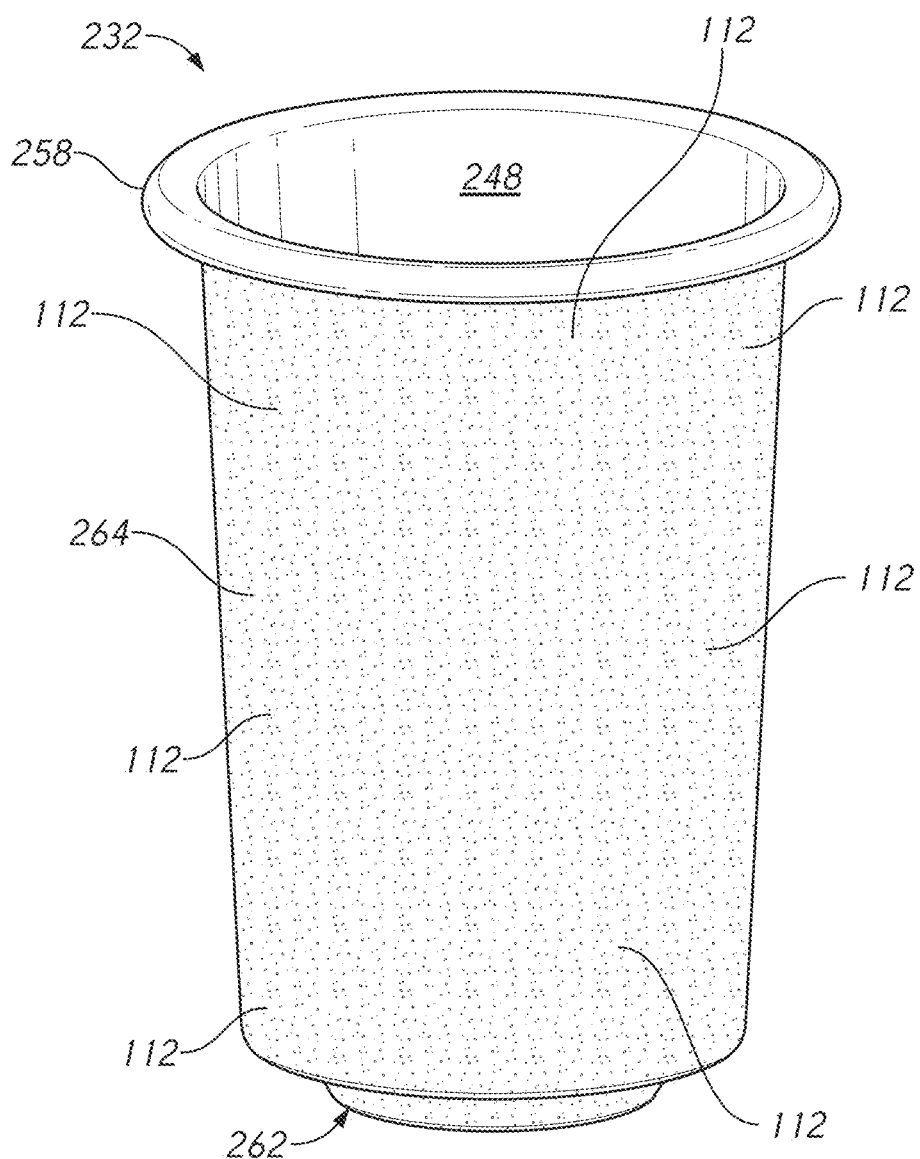
FIG. 5 is a front view of a fluid modifier from the medical fluid connector of FIG. 2A.

As shown in FIG. 5, in some embodiments, the flexible carrier 232 can be formed with a generally paraboloid shape, in which the exterior wall 264 comprises a wider proximal cross-sectional width and a narrower distal cross-sectional width. Any other suitable shape can be used (as shown in, for example, FIG. 3C). In some embodiments, as shown, the flexible carrier 232 can be made of a flexible, resilient, deformable, and/or compressible material, such as silicone or another polymeric material. In some embodiments, the compressible material is porous or adherent to allow temporary uptake or reception of a therapeutic or antibacterial agent that can be subsequently released into the medical fluid. As shown, in some situations, the additive 112 can be provided on only one side of the flexible carrier 232 (or on any other carrier of additive 112), especially in situations when the medical fluid only contacts the flexible carrier 232 on one side. Of course, in many embodiments, the additive 112 can be provided on multiple sides of the flexible carrier 232 or the flexible carrier 232 can be provided with additive 112 embedded within and/or throughout its structure, such as when the flexible carrier 232 is a matrix or otherwise has passages through which the medical fluid passes or in which the medical fluid is temporarily absorbed. In some embodiments, the flexible carrier 232, 232A, 232B, 232C, 232D can be molded or otherwise made in a natural or native shape as shown in FIGS. 3A-3E and 5. In some embodiments, the flexible carrier is woven or otherwise formed. In some situations, when the flexible carrier 232, 232A, 232B, 232C, 232D is deformed or compressed or moved in some way that is different from its natural or native shape, it can be configured to exert a restoring force to return resiliently to its natural or native shape. In some embodiments, the carrier can be formed of the additive 112 such that the carrier itself is partially or totally consumed or partially or totally dissolved away or leached into the medical fluid.

The flexible carrier 232, 232A, 232B, 232C, 232D can be configured to carry one or more additives 112 and to transfer the one or more additives 112 into the liquid that flows around or contacts the flexible carrier 232, 232A, 232B, 232C, 232D. In some embodiments, the one or more additives 112 can comprise any one or more of the following: an antimicrobial, an antibiotic, an antiseptic, an analgesic, an anesthetic, a blood-thinner, a chemotherapy drug, an immunosuppressive drug, a nutritional supplement, or any other therapeutic substance that is combinable with a liquid flowing through the connector 200, 200A, 200B, 200C, 200D. An example of an antimicrobial additive is chlorhexidine gluconate, which can be provided in powdered form and coated or dusted or positioned or otherwise placed around the outer surface of the exterior wall 264, 264A, 264B, 264C, 264D of the flexible carrier 232, 232A, 232B, 232C, 232D. In some embodiments, the one or more additives 112 can be temporarily adhered or bound or attached to the exterior wall 264, 264A, 264B, 264C, 264D of the flexible carrier 232, 232A, 232B, 232C, 232D, such as by electrostatic forces or in surface recesses or by a water-soluble or saline-soluble binder, such as glycerol. In some embodiments, the one or more additives 112 can be formed or trapped or bound to or into the structure of the exterior wall 264, 264A, 264B, 264C, 264D of the flexible carrier 232, 232A, 232B, 232C, 232D such as by being captured within a cross-linked matrix of the exterior wall 264, 264A, 264B, 264C, 264D in a manner that permits leaching out or eluting of the one or more additives into the liquid as the liquid flows around or through the flexible carrier.

In some embodiments, a degradable (e.g., biodegradable, water dissolvable, etc.) matrix is deposited on the exterior wall 264, 264A, 264B, 264C, 264D and/or on the flexible carrier 232, 232A, 232B, 232C, 232D. In some embodiments, the flexible carrier 232, 232A, 232B, 232C, 232D is a degradable matrix. In some embodiments, a portion of the degradable matrix dissolves upon exposure to medical fluid. In some embodiments, as the matrix degrades, sufficient additive is released into the medical fluid to permit locking of the catheter. In some embodiments, the degradable matrix can have a tailored or adjustable degradation rate and/or additive concentration such that the degradation rate and/or delivery concentration is sufficient to deliver an appropriate locking concentration throughout the estimated lifetime of the catheter or the connector. For example, if a catheter is estimated to require locking about 15 times over its lifetime, the flexible carrier 232, 232A, 232B, 232C, 232D can be tailored to allow 1, 2, 10, 15 or more locks of the catheter line with sufficient therapeutic agent to, for example, avoid microbial growth in the catheter during the average lifetime use of the catheter.

In some embodiments, the additive (e.g. as disposed in, around, or near the variable-volume fluid-modifying region 254, 254A, 254B, 254C, 254D or elsewhere in the connector) comprises antibiotic. In some embodiments, the antibiotic is a gram-positive antibacterial, a gram negative antibacterial, or a combination thereof. In some embodiments, the additive comprises one or more of chlorhexidine, chlorhexidine gluconate, vancomycin, cefazolin, ceftazidime, ciprofloxacin, gentamicin, and/or ampicillin.

In some embodiments, the additive comprises an anti-coagulant. In some embodiments, the anti-coagulent is heparin. The anti-coagulant can be provided as the only additive or as an additive in combination with other additives described elsewhere herein. In some embodiments, the anti-coagulant is provided at a concentration of at least about: 100 units/mL, 2500 units/mL, 5000 units/mL, values between the aforementioned values, ranges spanning those values, or otherwise.

In some embodiments, the connector is configured to provide an additive infused solution with a concentration of equal to or at least about 0.2 mg/mL, 0.5 mg/mL, 1.0 mg/mL, 2.5 mg/mL, 5.0 mg/mL, 10 mg/mL, values between the aforementioned values, ranges spanning those values, or otherwise.

As illustrated in FIGS. 6A-9 (for the embodiment shown in FIGS. 2A, 3A, and 3D-3F) and FIGS. 10-13 (for the embodiment shown in FIGS. 2C and 3C), some embodiments of the connector 200, 200C, 200D, 200B can provide fluid flow in a plurality of different stages with different fluid flow characteristics and/or different liquid compositions. For example, in a first stage of the connector 200, 200C, 200D, 200B, as illustrated in FIGS. 6A-6C and 10, the flexible carrier 232, 232C, 232D, 232B can be in a first or initial phase in which its shape, orientation, and/or location is in a default or natural or native position. When moved or modified away from this position to a second or modified phase, the flexible carrier 232, 232C, 232D, 232B can be configured to exert one or more restoring forces to return to the first or initial phase. As shown, in the first or initial phase, the outer exterior wall 264, 264C, 264D, 264B of the flexible carrier 232, 232C, 232D, 232B can be in contact with, cover, and/or overlay at least a portion of, or nearly entirely, or all of, an interior wall of the region of the housing 220, 220C, 220D, 220B of the connector 200, 200C, 200D, 200B in which the flexible carrier 232, 232C, 232D, 232B is disposed.

As shown in FIGS. 6A-6C and 10, as a medical liquid 266, 266C, 266D, 266B (e.g., saline) is infused into the proximal end of the connector 200, 200C, 200D, 200B, such as from a syringe 270 (not shown in FIGS. 6B and 6C), 270B or other medical implement, the medical liquid passes through the first fluid-line attachment 202, 202C, 202D, 202B, into the internal pathway 226, 226C, 226D, 226B of the fluid guide 224, 224C, 224D, 224B, and then to the transitional region 274, 274C, 274D, 274B. The transitional region 274, 274D, 274B can be between the distal end 272, 274D, 272B of the fluid guide 224, 224D, 224B and the diverter or divider 246, 246D, 246B. The transitional region 274C can be distal of the distal end 272C of the fluid guide 224C and the diverter or divider 246C. As shown, the cross-sectional width or diameter of the constriction or opening in the diverter or divider 246, 246C, 246D, 246B is smaller than the cross-sectional width or diameter of the internal pathway 226, 226C, 226D, 226B of the fluid guide 224, 224C, 224D, 224B.

Some of the medical liquid 266, 266C, 266D, 266B passes from the transitional region 274, 274D, 274B directly through the constriction or opening in the diverter or divider 246, 246D, 246B, or from the internal fluid pathway 226C directly through the opening in the diverter or diverter 246C, into the interior of the male protrusion 205, 205C, 205D, 205B. In some embodiments, as illustrated, the portion of the medical liquid 266, 266C, 266D, 266B that passes directly through can be essentially unchanged; that is, it can have the same or essentially the same composition as before it entered the connector 200, 200C, 200D, 200B, and/or it can be therapeutically or clinically the same (e.g., the medical liquid can have no concentration of additive or clinically insignificant concentration, which can be a low enough concentration of additive dissolved in the medical liquid such that the medical fluid can be infused directly into a patient or otherwise be used as though it were completely additive-free). This essentially unchanged medical liquid 266, 266C, 266D, 266B passes very quickly through the connector 200, 200C, 200D, 200B, without a clinically significant delay, and emerges from and continues to be emitted from the second fluid-line attachment 204, 204C, 204D, 204B during an initial time period or over a period during which an initial volume of liquid is dispensed from the connector 200, 200C, 200D, 200B.

Figure 6A:
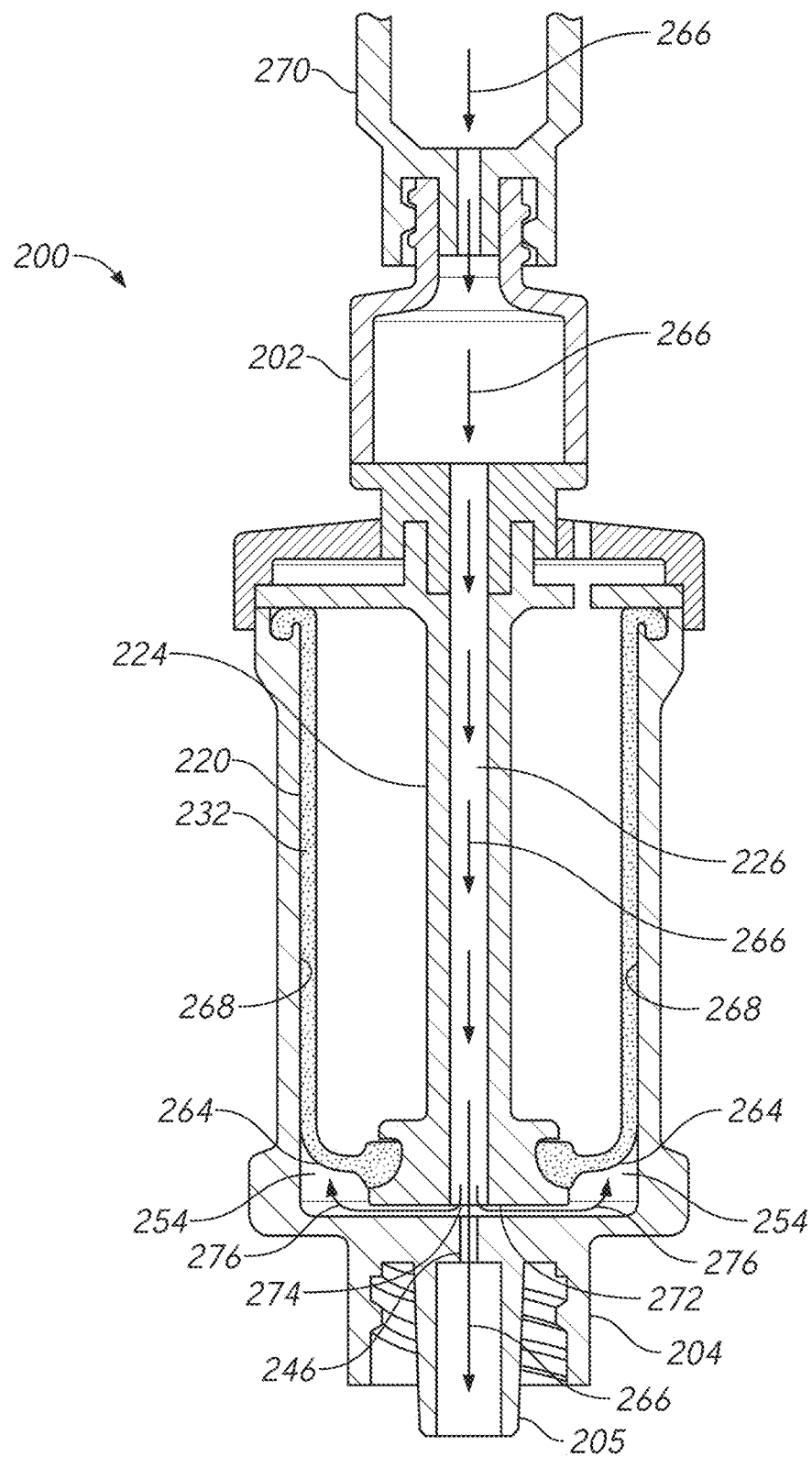
FIG. 6A is an example cross-sectional view of the medical fluid connector of FIG. 3A with a cross-sectional view of a distal end of a syringe attached to an inlet end of the connector in a first stage of fluid flow.
Figure 6B:
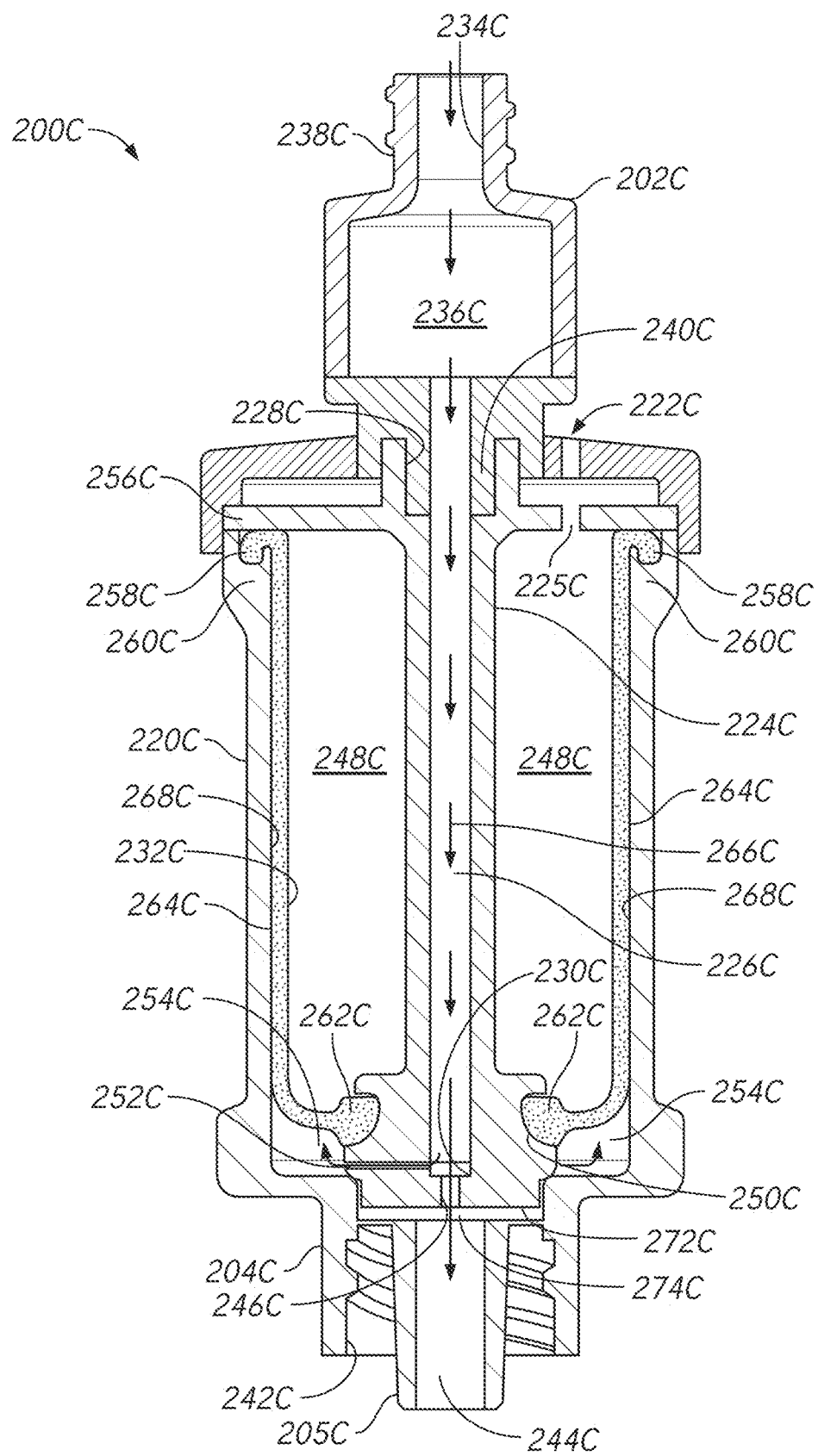
FIG. 6B is another example cross-sectional view of the medical fluid connector of FIG. 3D in a first stage of fluid flow.
Figure 6C:
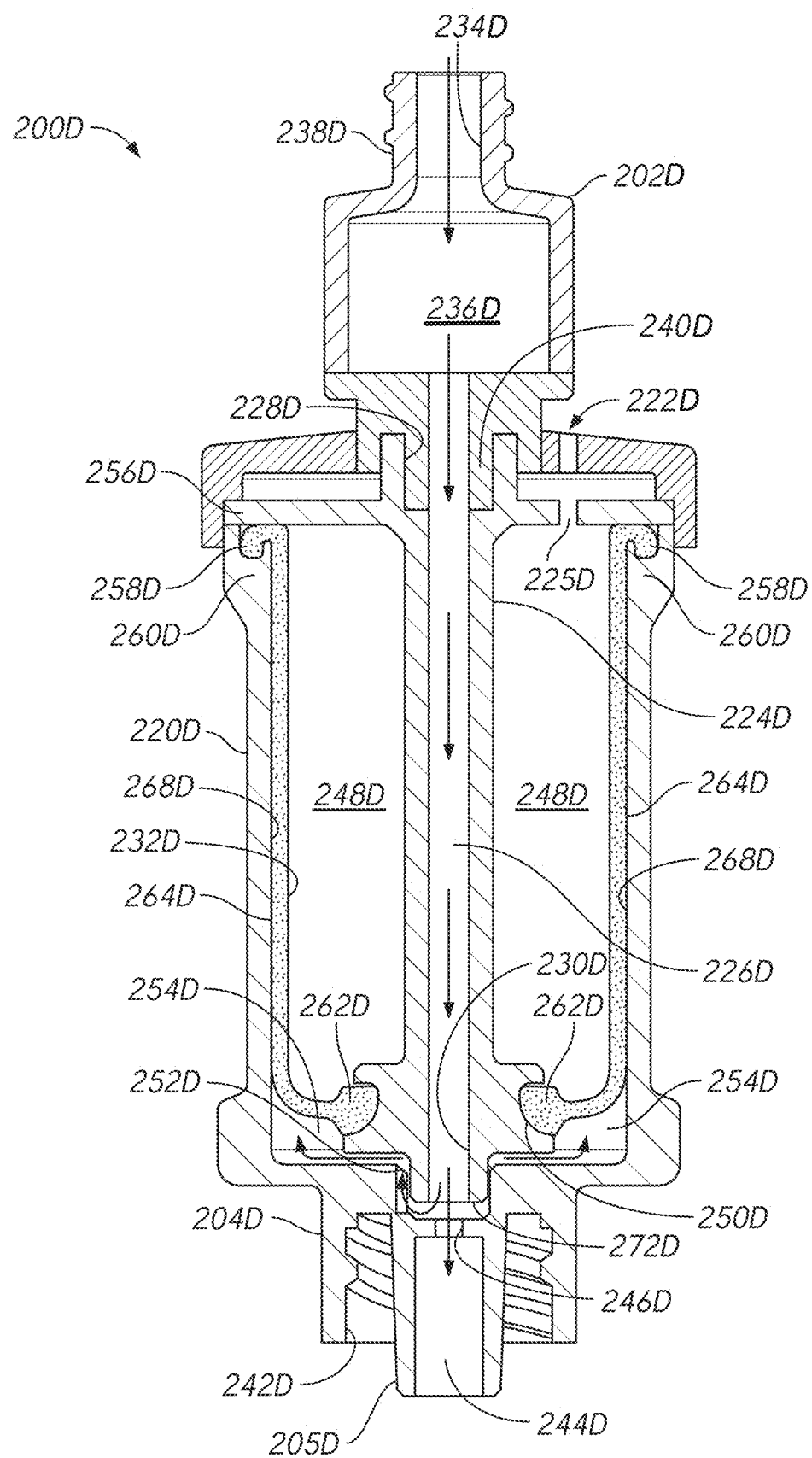
FIG. 6C is another example cross-sectional view of the medical fluid connector of FIGS. 3E-F in a first stage of fluid flow.
Figure 7:
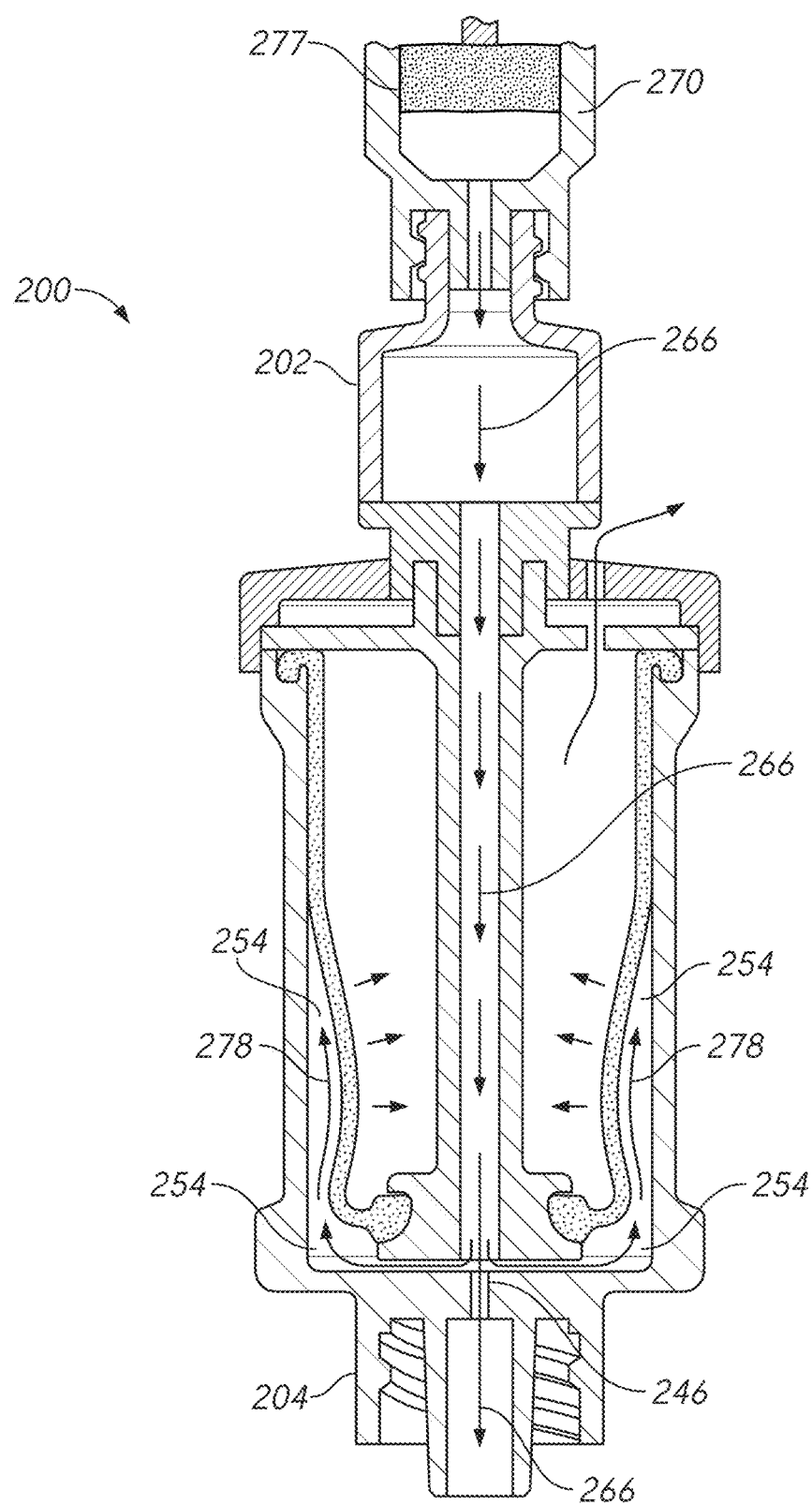
FIGS. 7 and 8 are example cross-sectional views of the medical fluid connector of FIG. 3A with a cross-sectional view of a distal end of a syringe attached to an inlet end of the connection in a second stage of fluid flow.

Generally simultaneously, another portion of the medical liquid 266, 266C, 266D, 266B is diverted laterally because the opening in the diverter or divider 246, 246C, 246D, 246B creates a lower flow rate (volume/time) of medical liquid 266, 266C, 266D, 266B entering from the wider internal fluid pathway 226, 226C, 226D, 226B of the fluid guide 224, 224C, 224D, 224B (and the transitional region 274, 274D, 274B) into the opening in the diverter or divider 246, 246C, 246D, 246B. As described above, the transitional region 274, 274D, 274B in FIGS. 6A, 6C, and 10 respectively can include the proximal opening of the diverter or divider 246, 246D, 246B and the lateral opening where the portion of the medical liquid 266, 266D, 266B is diverted laterally, and/or the space or volume located between these locations or structures. As described above, the lateral fluid region 252C and the diverter or divider 246C in FIG. 6B can both be located proximal to the transitional region 274C. A ratio of the flow rate of medical fluid, and hence a volume of medical fluid, entering into the opening in the diverter or divider and into the lateral fluid region can be proportional to a ratio of the cross-sectional areas of the opening in the diverter or divider and the lateral fluid region. In some embodiments, such as shown in FIGS. 6B and 6C, the cross-sectional area of the opening in the diverter or divider 246C, 246D can be at least about three times or at least about four times that of the lateral fluid region 252C, 252D. When a volume of the medical fluid 266C, 266D enters the fluid pathway 226C, 226D, at least about 70% or at least about 80% of the volume of the medical fluid 266C, 266D enters the opening in the diverter or divider 246C, 246D, and less than or equal to about 30% or less than or equal to about 20% of the volume of the medical fluid 266C, 266D enters the lateral fluid region 252C, 252D. The ratio of the volume of medical fluid entering into the opening in the diverter or divider and into the lateral fluid region can be adjusted by adjusting the ratio of the cross-sectional areas of the opening in the diverter or divider and the lateral fluid region. In some embodiments, such as shown in FIGS. 6B and 6C, the ratio of the cross-sectional areas of the opening in the diverter or divider and the lateral fluid region can be adjusted by changing the size of the opening in the diverter or divider 246C, 246D, and/or the size of the lateral fluid region 252C, 252D.

In some embodiments, the diverted or laterally flowing liquid 276, 276C, 276D, 276B moves into the variable-volume fluid-modifying region 254, 254C, 254D, 254B and begins to: (a) exert a modifying force on the flexible carrier 232, 232C, 232D, 232B; and/or (b) contacts the exterior wall 264, 264C, 264D, 264B of the flexible carrier 232, 232C, 232D, 232B. In some embodiments of the connector 200, 200C, 200D, 200B, where the fluid modifier 116 is a flexible member but not a flexible carrier 232, 232C, 232D, 232B (e.g., because the fluid modifier 116 does not carry an additive 112), the variable-volume fluid-modifying region 254, 254C, 254D, 254B can contain the additive 112 or some other region or structure of the connector 200, 200C, 200D, 200B can contain or hold the additive 112 (e.g., a portion of a fluid-contacting inner wall 268, 268C, 268D, 268B of the housing 220, 200C, 200D, 220B or a portion of the fluid guide 224, 224C, 224D, 224B or one or more of any other structures or components of the connector 200, 200C, 200D, 200B, or any combination of structures or components). In some embodiments, the additive 112 can be omitted.

As shown in FIGS. 7-8 and 11-12, in a second stage of the connector 200, 200B, as more medical liquid 266, 266B is infused into the connector 200, 200B (such as by distally advancing and/or depressing a syringe plunger 277, 277B in the syringe 270, 270B), more medical liquid 266, 266B continues to pass through the diverter or divider 246, 246B and more liquid is forced into the variable-volume fluid-modifying region 254, 254B. The connector 200C, 200D can also have a second stage that can have substantially the same features as disclosed herein with reference to FIGS. 7 and 8 and that is not repeated for brevity. The additional liquid in the variable-volume fluid-modifying region 254, 254B causes the liquid to exert a force against the flexible carrier 232, 232B which causes at least a portion of the flexible carrier 232, 232B, such as a wall of the flexible carrier, to flex, bend, contract, collapse, deform, or otherwise move away from its default or natural or native position. The fluid-modifying region 254, or any component thereof, including the flexible carrier 232, 232B, can comprise a material that is softer, more pliable, more resilient, and/or more flexible than the material of the housing 220 of the connector 200. In some embodiments, at the same time, air contained within the internal region 248, 248B of the flexible carrier 232, 232B can be forced outside of the flexible carrier and through the vent 225, 225B and air port 222, 222B into the atmosphere. As shown, this escaping air can be sealed off from the flow of liquid through the connector 200, 200B. In some embodiments, the connector 200, 200B lacks a vent 225, 225B and the internal region 248, 248B is closed. In the illustrated embodiments, the mixing and emitting of additive into the medical liquid, and the fluid flow within the connector 200, are not accomplished through erosion or dissolving or washing away of one or more layers that are configured to initially block mixing or emitting of the additive, but rather by a dynamic movement of one or more components of the connector that changes the direction, position, orientation, and/or volume of one or more fluid flow paths within the connector 200. Some embodiments can include one or more processes of mixing or emitting that include eroding or dissolving or washing away of one or more layers into the surrounding fluid.

As illustrated, in some embodiments, the movement of the flexible carrier 232, 232B can create a void between the exterior wall 264, 264B of the flexible carrier 232, 232B and the interior wall 268, 268B of the connector 200, 200B, which can increase the size of the variable-volume fluid-modifying region 254, 254B and temporarily store or retain liquid within the increasingly large fluid-modifying region 254, 254B. Once the flexible carrier 232, 232B begins to deform, it exerts a restoring force in opposition to the force of the entering liquid. In some embodiments, the force of the entering liquid is greater than the restoring force of the flexible carrier 232, 232B during the infusion stage. Simultaneously, the liquid in the fluid-modifying region 254, 254B can come into contact with and mix with one or more additives 112 on the flexible carrier 232, 232B or otherwise, transforming the liquid into a therapeutic liquid 278, 278B (e.g., an additive-containing liquid). In some embodiments, the therapeutic liquid 278, 278B can flow or swirl generally circumferentially around the interior of the housing 220, 220B of the connector 200, 220B in a general vortex pathway as medical liquid is infused into the connector 200, 200B, between the interior wall 268, 268B of the housing 220, 220B and the exterior wall 264, 264B of the flexible carrier 232, 232B, providing thorough mixing and consistency of concentration of additive 112 in the therapeutic liquid 278, 278B.

Figure 8:
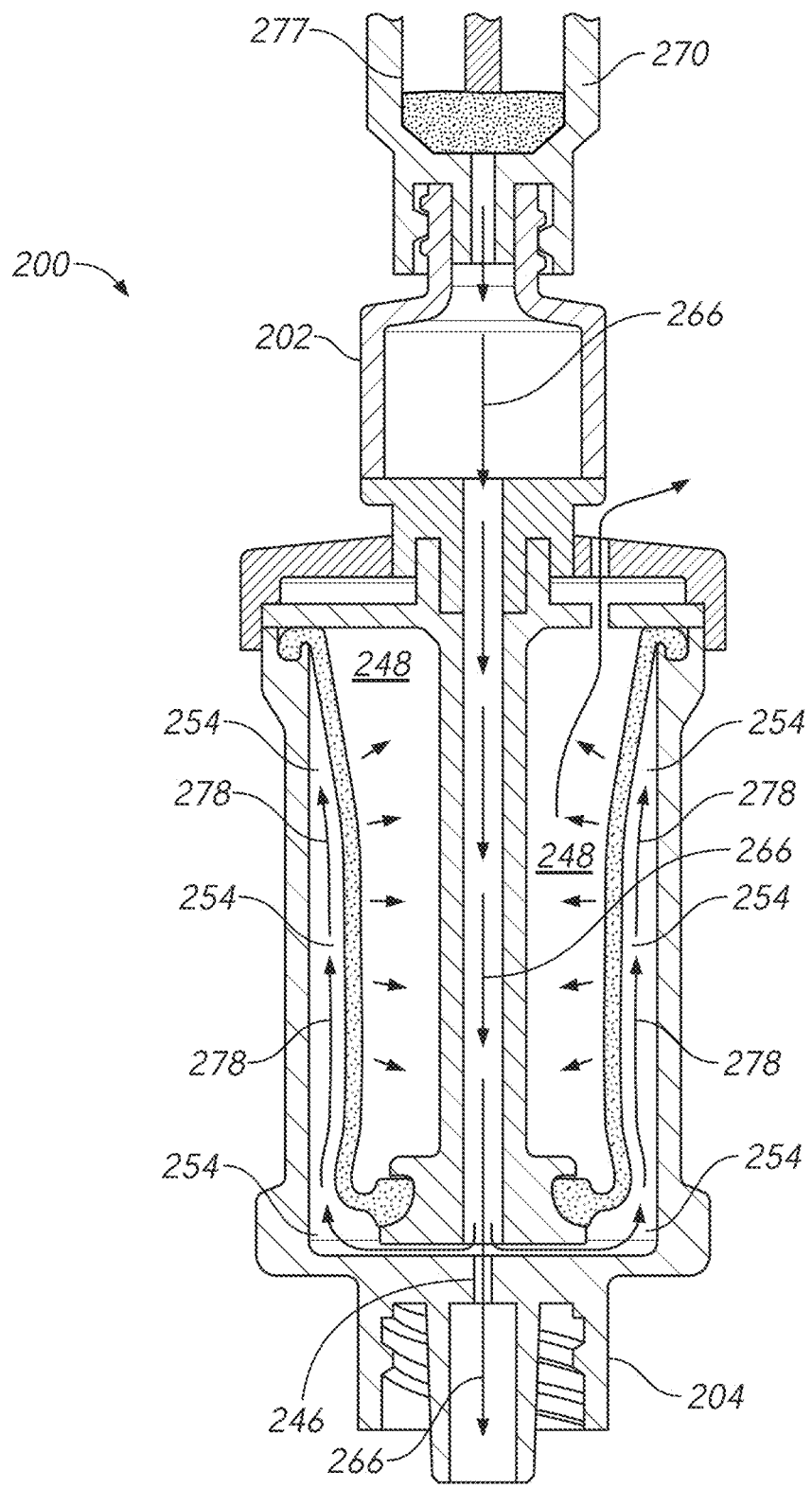
Figure 12:
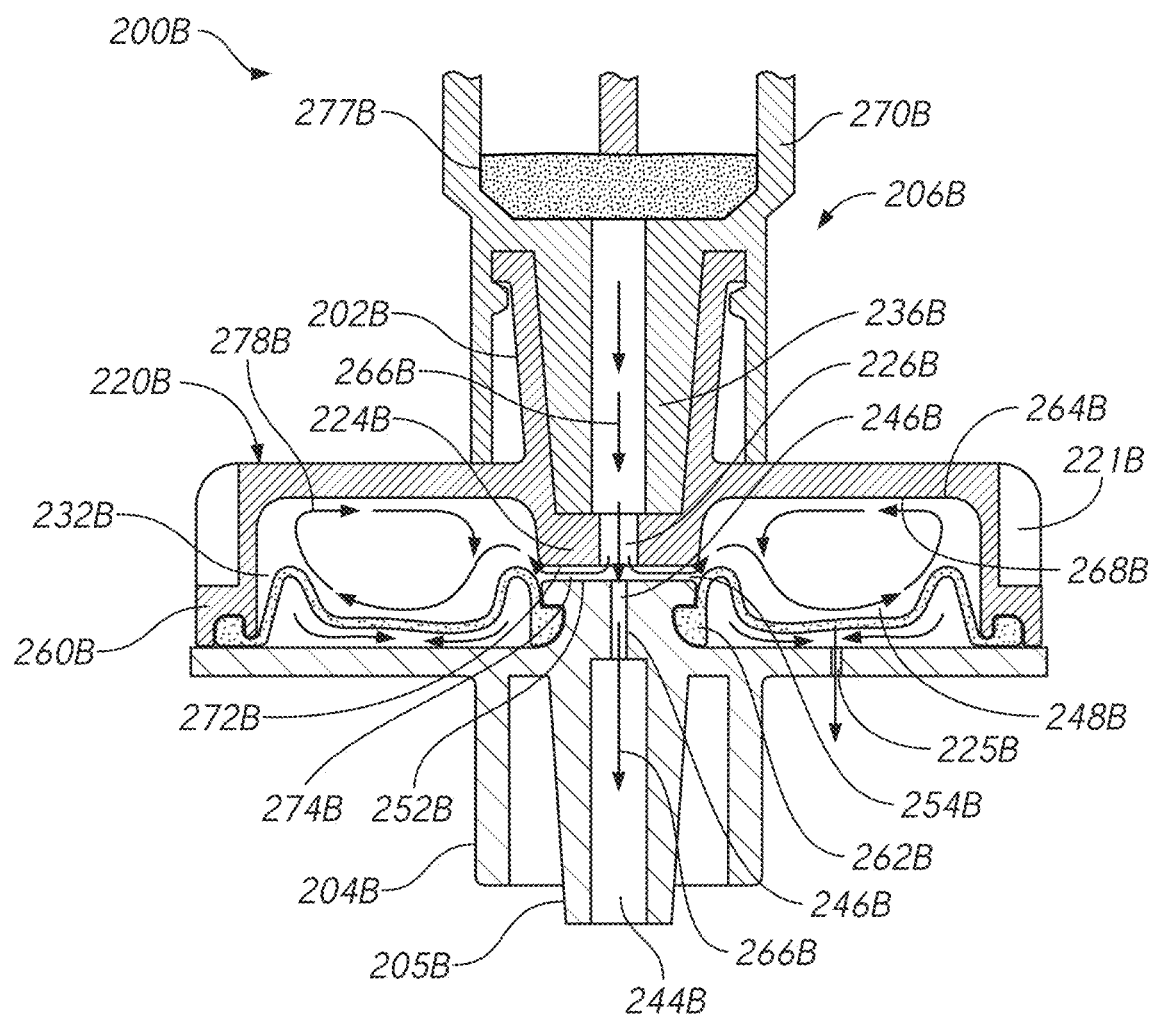

As shown in FIGS. 8 and 12, the second stage of the connector 200, 200B can end when the infusion of medical liquid 266, 266B into the connector 200, 200B ends, such as when the plunger 278, 278B of the syringe 270, 270B stops or bottoms out or moves to its distal end point within the syringe barrel. At this point, the fluid pressure within the main fluid pathway can decrease, and medical liquid 266, 266B can stop flowing from the first fluid-line attachment 202, 202B through the connector 200, 200B to the second fluid-line attachment 204, 204B.

Figure 9:
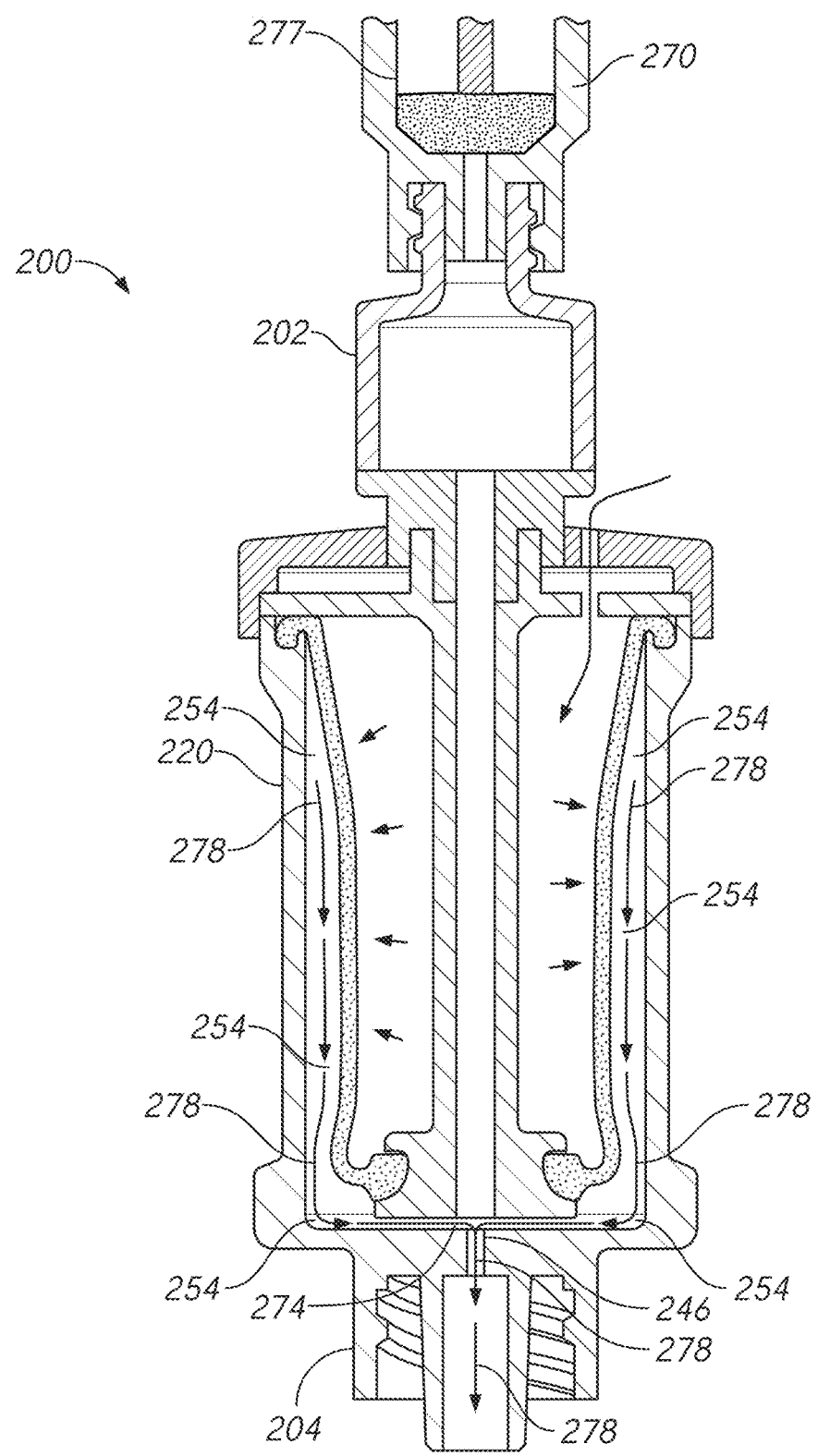
FIG. 9 is an example cross-sectional view of the medical fluid connector of FIG. 3A with a cross-sectional view of a distal end of a syringe attached to an inlet end of the connection in a third stage of fluid flow.
Figure 10:
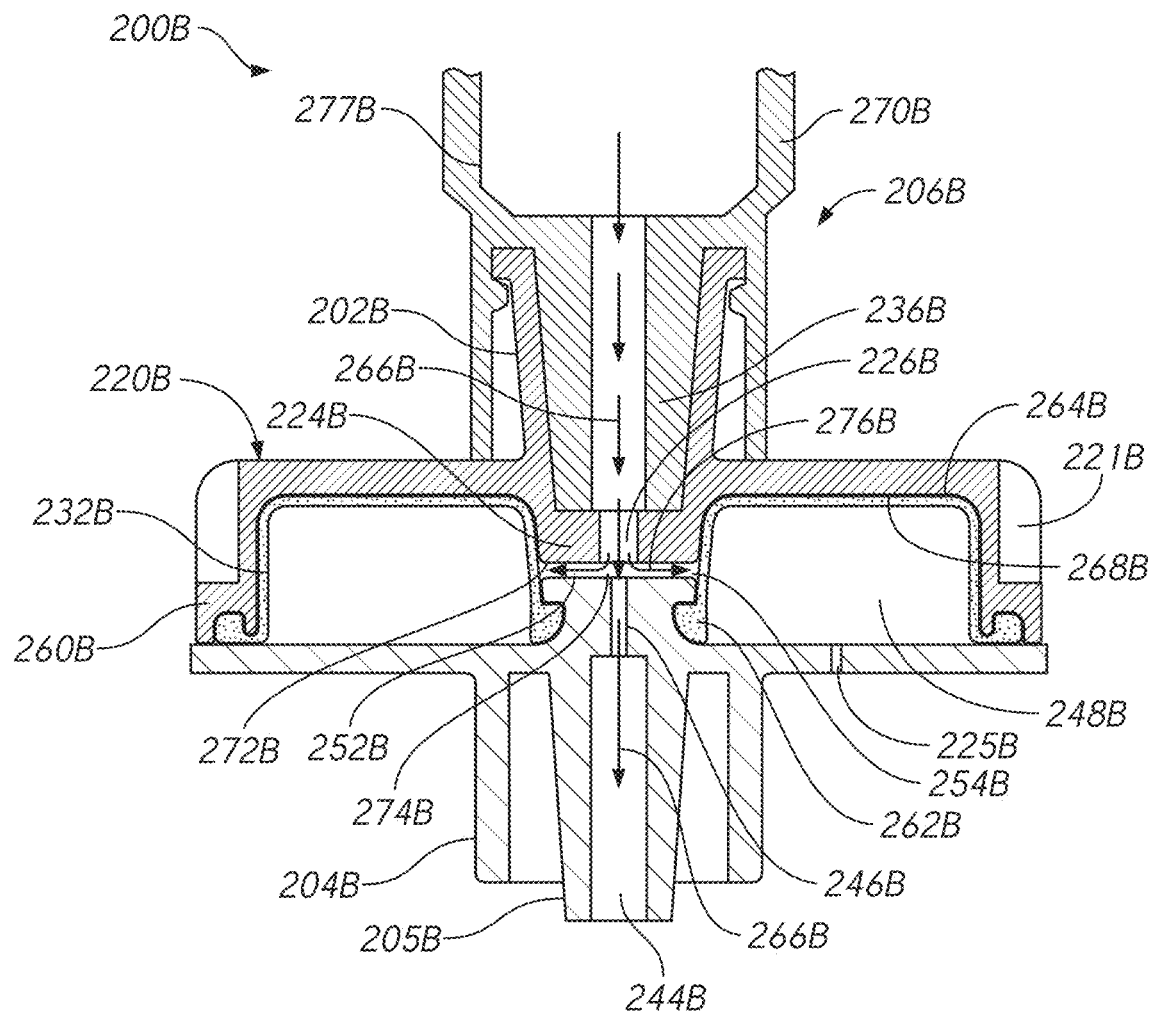
FIG. 10 is a cross-sectional view of the medical fluid connector of FIG. 2C with a cross-sectional view of a distal end of a syringe attached to an inlet end of the connector in a first stage of fluid flow.
Figure 11:
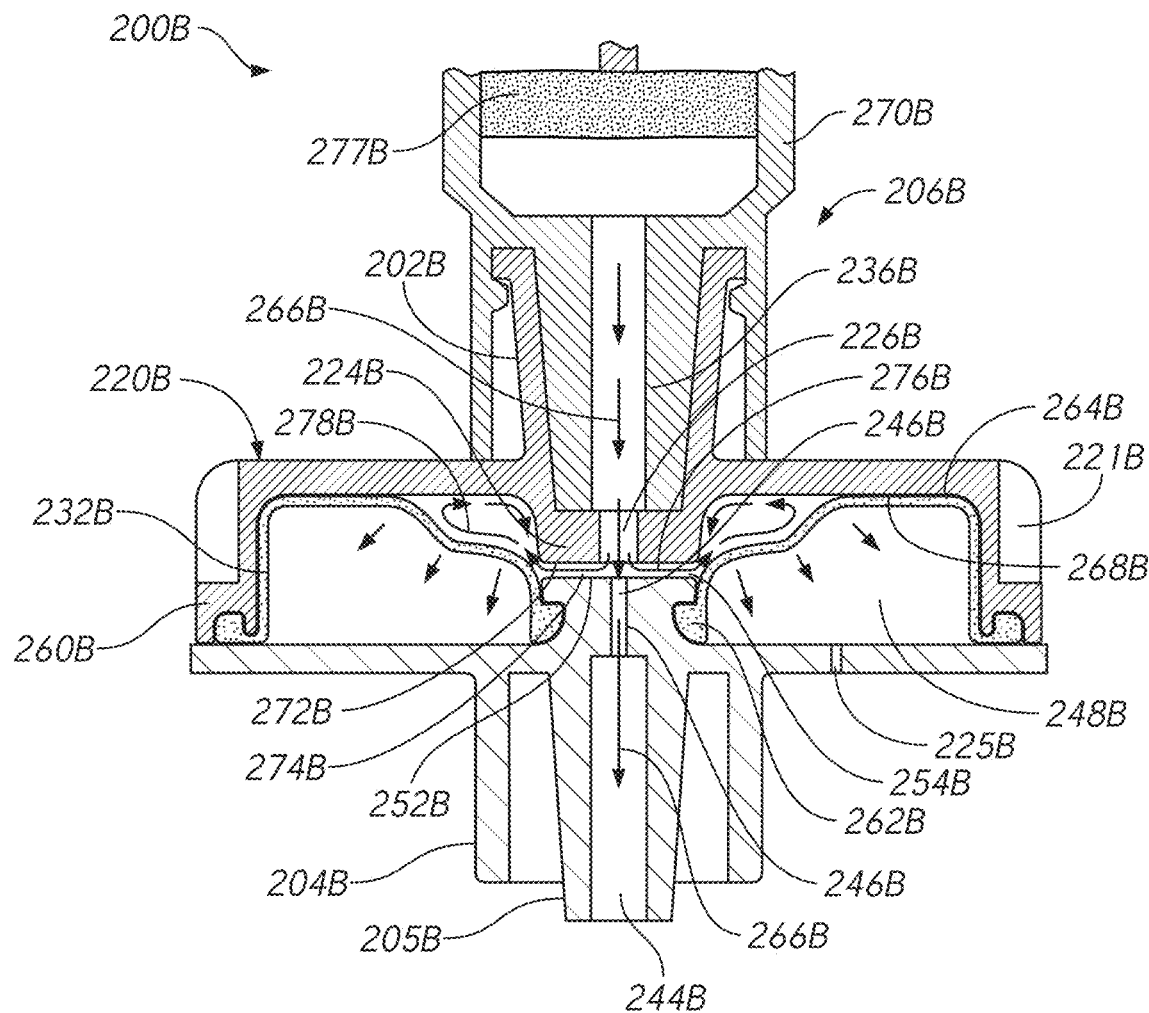
FIGS. 11 and 12 are cross-sectional views of the medical fluid connector of FIG. 2C with a cross-sectional view of a distal end of a syringe attached to an inlet end of the connector in a second stage of fluid flow.
Figure 13:
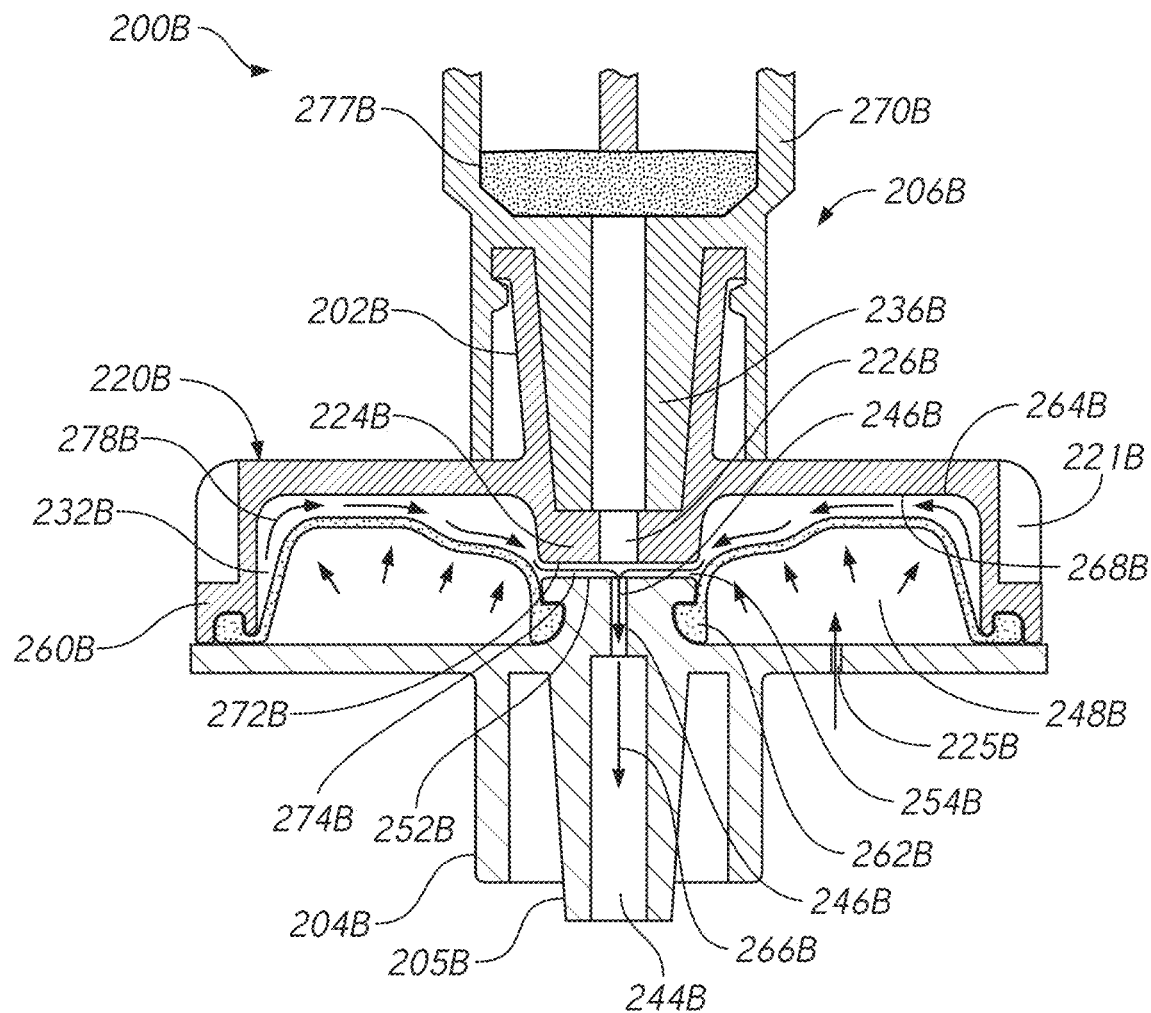
FIG. 13 is a cross-sectional view of the medical fluid connector of FIG. 2C with a cross-sectional view of a distal end of a syringe attached to an inlet end of the connector in a third stage of fluid flow.

As illustrated in FIGS. 9 and 13, a third stage of the connector 200, 200B can begin upon completion of the second stage, or at any other suitable time (such as after a delay after completion of the second stage). The connector 200C, 200D can also have a third stage that can have substantially the same features as disclosed herein with reference to FIG. 9 and that is not repeated for brevity. In the third stage, the therapeutic liquid 278, 278B stored in the fluid-modifying region 254, 254B is no longer under pressure from the medical liquid 266, 266B that was previously being infused into the connector 200, 200B during stage two of the connector 200, 200B, and the restoring force exerted by the flexible carrier 232, 232B can then move the flexible carrier 232, 232B back toward its default or native or natural position in its first or initial phase. As the flexible carrier 232, 232B moves back toward its first or initial phase, the fluid modifying region 254, 254B shrinks or contracts or otherwise moves to decrease in size, and the therapeutic liquid 278, 278B in the fluid-modifying region 254, 254B is forced out, passing through the transitional region 274, 274B and the diverter or divider 246, 246B, into the male protrusion 205, 205B, and out of the connector 200, 200B. Thus, in some embodiments, the third stage can begin after infusion from the source (e.g., the syringe 270, 270B) of medical liquid 266, 266B stops, at which point a volume of therapeutic fluid 278, 278B is then dispensed from the distal end of the connector 200, 200B. In embodiments where the internal region of the connector is closed (e.g., in embodiments that lack a vent 225, 225B), the internal region increases in pressure upon deformation of the flexible carrier during depression of the syringe plunger. This pressure increase can be used to aid in forcing the additive-infused fluid out of the connector by exerting pressure on the flexible carrier, forcing the flexible carrier back into its original position.

Any of the first or second or third or other stages can be combined or eliminated. Any steps or methods that are described and/or illustrated in any particular stage can be performed additionally or alternatively in another stage. The descriptions and/or illustrations of stages are not intended to be exhaustive or limiting. In some embodiments, as illustrated, any transition from any stage to any other stage can be automatic. For example, one or more transitions between any stages can be governed by fluid-flow and/or fluid pressure parameters, not by one or more intentional or direct user adjustments or modifications of the connector. In some embodiments, one or more connector features can be manipulated and used collectively and/or singularly to adjust and/or manipulate the ratio of medical fluid that remains substantially additive-free versus the amount of medical fluid infused with an additive (or additives). In some embodiments, multiple connector types with various features can be mixed and matched and attached serially for the infusion of multiple additives and/or to achieve multiple infusion profiles. As shown, in some embodiments, any of the connectors 200, 200A, 200B, 200C, 200D can be different from long-term medical pumps (e.g., bladder pumps or ambulatory pumps) in that the fluid-flow emitted from the downstream or outflow end or region of the connectors 200, 200A, 200B, 200C, 200D can terminate or stop generally simultaneously with or shortly after the fluid-flow infused or inserted into the upstream or inflow end or region of the connectors 200, 200A, 200B, 200C, 200D. For example, in some embodiments, as illustrated, the time between the beginning of fluid-flow infused or inserted into the upstream or inflow end or region of the connectors 200, 200A, 200B, 200C, 200D and the end of fluid-flow infused or inserted into the upstream or inflow end or region of the connectors 200, 200A, 200B, 200C, 200D can be generally equal to or greater than the time between the end of fluid-flow infused or inserted into the upstream or inflow end or region of the connectors 200, 200A, 200B, 200C, 200D and the end of fluid-flow emitted from the downstream or outflow end or region of the connectors 200, 200A, 200B, 200C, 200D, such that the connectors 200, 200A, 200B, 200C, 200D do not provide a long-term pumping function. Of course, in some embodiments, one or more structures, methods, functions, and/or components that are illustrated in the accompanying figures and/or described anywhere in this specification can be used in or with medical pumps or can be used as medical pumps with appropriate modifications.

In some embodiments, the cross-sectional area (e.g., diameter) of the internal fluid pathway is larger than the cross-sectional area of the fluid pathway through (or the opening in) the constriction or diverter or divider. In some embodiments, the diverter or divider can be a constriction. In some embodiments, the ratio of the cross-sectional area of the internal fluid pathway 226, 226A, 226B, 226C, 226D and the cross-sectional area of the opening in the diverter or divider or constriction 246, 246A, 246B, 246C, 246D can be changed from connector to connector to divert more or less liquid into the fluid modifying region. For example, if only a small volume of liquid is being infused, it may be advantageous to divert a larger volume of liquid into the fluid modifying region to allow sufficient additive to be infused into the medical fluid. As the cross-sectional area of the internal fluid pathway becomes larger relative to the cross-sectional area of the fluid pathway at the diverter or divider or constriction, more fluid pressure builds at the diverter or divider or constriction diverting more fluid into the fluid modifying region. In some embodiments, the ratio of a cross-sectional area of the internal fluid pathway to the cross-sectional area of the fluid pathway through the diverter or divider or constriction is equal to or less than about: 5:4, 4:3, 2:1, 5:1, values between the aforementioned ratios, ranges spanning those ratios, or otherwise.

Alternatively or additionally, in some embodiments, the cross-sectional area of the entrance (e.g., the lateral fluid region) to the fluid modifying region is larger than the cross-sectional area of the fluid pathway through the diverter or divider or constriction. In some embodiments, the ratio of the cross-sectional area of the entrance of the fluid modifying region to the cross-sectional area of the opening in the diverter or divider or constriction can be different among a plurality of connectors to divert more or less liquid into the fluid modifying region, depending upon clinical needs. When the cross-sectional area of the entrance to the fluid modifying region is larger than the cross-sectional area of the fluid pathway at the diverter or divider or constriction, more fluid can be diverted into the fluid modifying region. In some embodiments, the ratio of a cross-sectional area of the entrance to fluid modifying region to the cross-sectional area of the fluid pathway through the diverter or divider or constriction is equal to or less than about: 2:1, 5:1, 10:1 values between the aforementioned ratios, ranges spanning those ratios, or otherwise.

Figure 14:
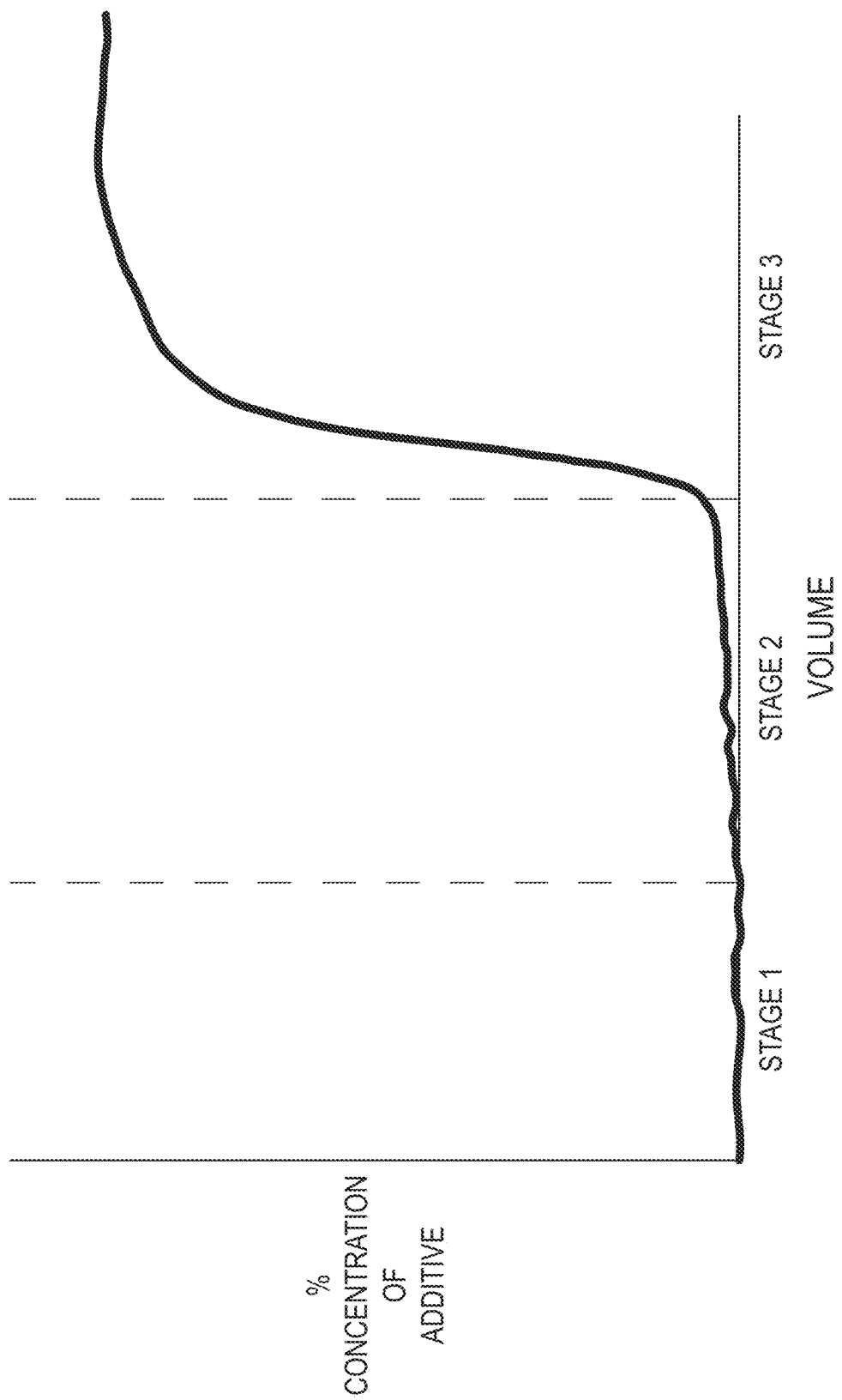
FIG. 14 is a graph showing an example of an infusion of liquid through a connector of FIG. 2A, that illustrates a relationship between the concentration of additive as compared to infused volume.

In some embodiments, the volume of the secondary pathway can be adjusted and/or the volume of the primary fluid pathway can be adjusted. In some embodiments, the capacity of the secondary fluid pathway (e.g., the volume of liquid the secondary pathway can hold when filled) is equal to or at least about: 0.125 mL, 0.25 mL, 0.5 mL, 2 mL, 5 mL, values between the aforementioned values, ranges spanning those values, or otherwise. In some embodiments, capacity of the primary fluid pathway is equal to or at least about: 0.1 mL, 0.2 mL, 0.5 mL, 1 mL, values between the aforementioned values, ranges spanning those values, or otherwise. In some embodiments, by making the volume of the secondary fluid pathway 110 larger than the volume of the main fluid pathway 108, a larger volume of additive-infused medical liquid can be infused into the catheter. As shown in FIGS. 14 and 15, differing volume ratios of the main fluid pathway and secondary fluid pathway can be used to achieve different release profiles. In some embodiments, the ratio of the volume of the secondary fluid pathway to the volume of the main fluid pathway is equal to or greater than about: 0.5:1, 1:1, 2:1, 4:1, ratios between the aforementioned ratios, ranges spanning those ratios, or otherwise. In some embodiments, the ratio of the length of the secondary fluid pathway to the length of the main fluid pathway can be adjusted. In some embodiments, the ratio of the length of the secondary fluid pathway to the length of the main fluid pathway is equal to or greater than about: 0.5:1, 1:1, 2:1, 4:1, ratios between the aforementioned ratios, ranges spanning those ratios, or otherwise. In some embodiments, the connector can be configured to have a low retained volume of fluid after the third stage is complete. In some embodiments, the retained volume of fluid in the connector after the third stage is less than or equal to about: 0.5 mL, 0.2 mL, 0.1 mL, values between the aforementioned values, ranges spanning those values, or otherwise.

In some embodiments, as discussed elsewhere herein, the medical fluid can enter the secondary fluid pathway 110 (or an additional fluid pathway) based in part on the rate and/or the volume of medical fluid injected into the connector 100. In some embodiments, for example, the amount of deformation of the flexible carrier and/or the amount of fluid that enters the secondary pathway depends on the rate at which a fluid is passed through main fluid pathway of the connector. In some embodiments, the secondary fluid pathway 110 is filled with medical fluid and/or the flexible carrier deforms when an infusion from, for example, a syringe into the connector reaches a rate of equal to, or at least, about: 0.25 mL/sec, 0.5 mL/sec, 2 mL/sec, 5 mL/sec, values between the aforementioned values, ranges spanning those values, or otherwise. In some embodiments, the additive can be completely or substantially distributed into the medical fluid with an infusion rate from a syringe (or other infusion device) of equal to, or at least, about: 0.25 mL/sec, 0.5 mL/sec, 2 mL/sec, 5 mL/sec, values between the aforementioned values, ranges spanning those values, or otherwise.

In some embodiments, the amount of deformation of the flexible carrier and/or the amount of fluid that enters the secondary pathway depends on the volume of fluid that is passed through the connector. In some embodiments, the secondary fluid pathway 110 is filled with medical fluid when an infusion volume is equal to or at least about: 2.5 mL, 5 mL, 10 mL, values between the aforementioned values, ranges spanning those values, or otherwise. In some embodiments, the additive can be completely or substantially completely distributed into the medical fluid using an infusion volume of equal to or at least about: 2.5 mL, 5 mL, 10 mL, values between the aforementioned values, ranges spanning those values, or otherwise.

In some embodiments, the resiliency and/or the modulus of the flexible carrier can be selected to provide different release characteristics. In some embodiments, stiff materials deform less and result in less additive being added to the medical fluid but can expel the additive at a greater pressure and in less time. In some embodiments, the resilience of the flexible carrier is at least about: 0.1 $J/m^3$, 1 $J/m^3$, 10 $J/m^3$, 100 $J/m^3$, values between the aforementioned values, ranges spanning those values, or otherwise. In some embodiments, the modulus of the flexible carrier is greater than or equal to about: 0.01 GPa, 0.1 GPa, 1 GPa, 2 GPa, values between the aforementioned values, ranges spanning those values, or otherwise.

In some embodiments, a portion of the flexible carrier can comprise an indicator, for instance, a colored, luminescent, or fluorescent dye (not shown). In some embodiments, the indicator dissolves into the medical fluid with the additive. In some embodiments, the indicator is located on a portion of the flexible carrier that is away from or distal to the transitional region so that the indicator is only infused into the medical fluid after all or substantially all the additive is infused into the medical fluid. In some embodiments, where the indicator is present, the indicator only enters into the medical fluid when an appropriate rate and/or volume of medical fluid enters the variable-volume fluid-modifying region 254, 254A, 254B, 254C, 254D. In some embodiments, the indicator can be used to visually demonstrate that the additive has been appropriately infused into the medical fluid. In some embodiments, the indicator may also be used to visualize the distance that the lock solution (or any other therapeutic solution) has traveled in the catheter line.

In some embodiments, as shown in at least FIGS. 6A-9 and FIGS. 10-13, the connector 200, 200C, 200D, 200B can be structured and/or configured to: (a) initially direct liquid into the secondary fluid pathway 110 (e.g., the lateral fluid region 252, 252C, 252D, 252B and the variable-volume fluid-modifying region 254, 254C, 254D, 254B) in an entrance direction and then subsequently direct that same liquid, in a modified form, back out of the secondary fluid pathway 110, in a substantially or primarily opposite exit direction; (b) simultaneously provide a first fluid pathway through an interior or central region of the connector 200, 200C, 200D, 200B (e.g., internal fluid pathway 226, 226C, 226D, 226B) and a second fluid region or pathway (e.g., the lateral fluid region 252, 252C, 252D, 252B and the variable-volume fluid-modifying region 254, 254C, 254D, 254B) through or around or into a peripheral or outer region of the connector 200, 200C, 200D, 200B; (c) simultaneously permit some portion of fluid conveyed within the connector 200, 200C, 200D, 200B to move primarily in a distal direction (e.g., in the fluid guide 224, 224C, 224D, 224B) and some portion of fluid conveyed within the connector 200, 200C, 200D, 200B to move primarily in a proximal direction (e.g., into the variable-volume fluid-modifying region 254, 254C, 254D, 254B); (d) provide a single fluid exit (e.g., diverter or divider or constriction 246, 246C, 246D, 246B) for both the main fluid pathway 108 and the secondary fluid pathway 110; (e) automatically continue emitting fluid out of the fluid exit region 114 (e.g., out of the male protrusion 205, 205C, 205D, 205B) for a clinically significant period of time after infusion of fluid into the fluid entry region 106 has stopped and/or produce an automatic delay in stopping the flow of fluid or permit a continuation in delivering or emitting a substantial or clinically significant amount of fluid (e.g., at least about 20% of the fluid-holding capacity of the overall connector 200, 200C, 200D, 200B or at least about 5 mL or at least about 10 mL) out of the fluid exit region 114 (e.g., male protrusion 205, 205C, 205D, 205B) after the infusion of fluid into the fluid entry region 106 (e.g., the first fluid-line attachment 202, 202C, 202D, 202B) has stopped; (f) provide an internal fluid pathway 226, 226C, 226D, 226B that does not move with respect to the housing 220, 220C, 220D, 220B of the connector 200, 200C, 200D, 200B; (g) provide a rigid internal fluid pathway (e.g., internal fluid pathway 226, 2226C, 226D, 226B) that extends across and/or within a flexible member (e.g., flexible carrier 232, 232C, 232D, 232B); (h) provide fluid flow both inside and outside of a flexible member (e.g., flexible carrier 232, 232C, 232D, 232B); (i) provide fluid contact and/or fluid flow across or around or on an outside surface of a flexible member; and/or (j) provide a rigid internal fluid pathway (e.g., internal fluid pathway 226, 226C, 226D, 226B) that extends across and/or within a flexible member (e.g., flexible carrier 232, 232C, 232D, 232B), the internal fluid pathway being longitudinally stationary with respect to the flexible member. Any of these features can be included in or omitted from any embodiment in this application.

Figure 15:
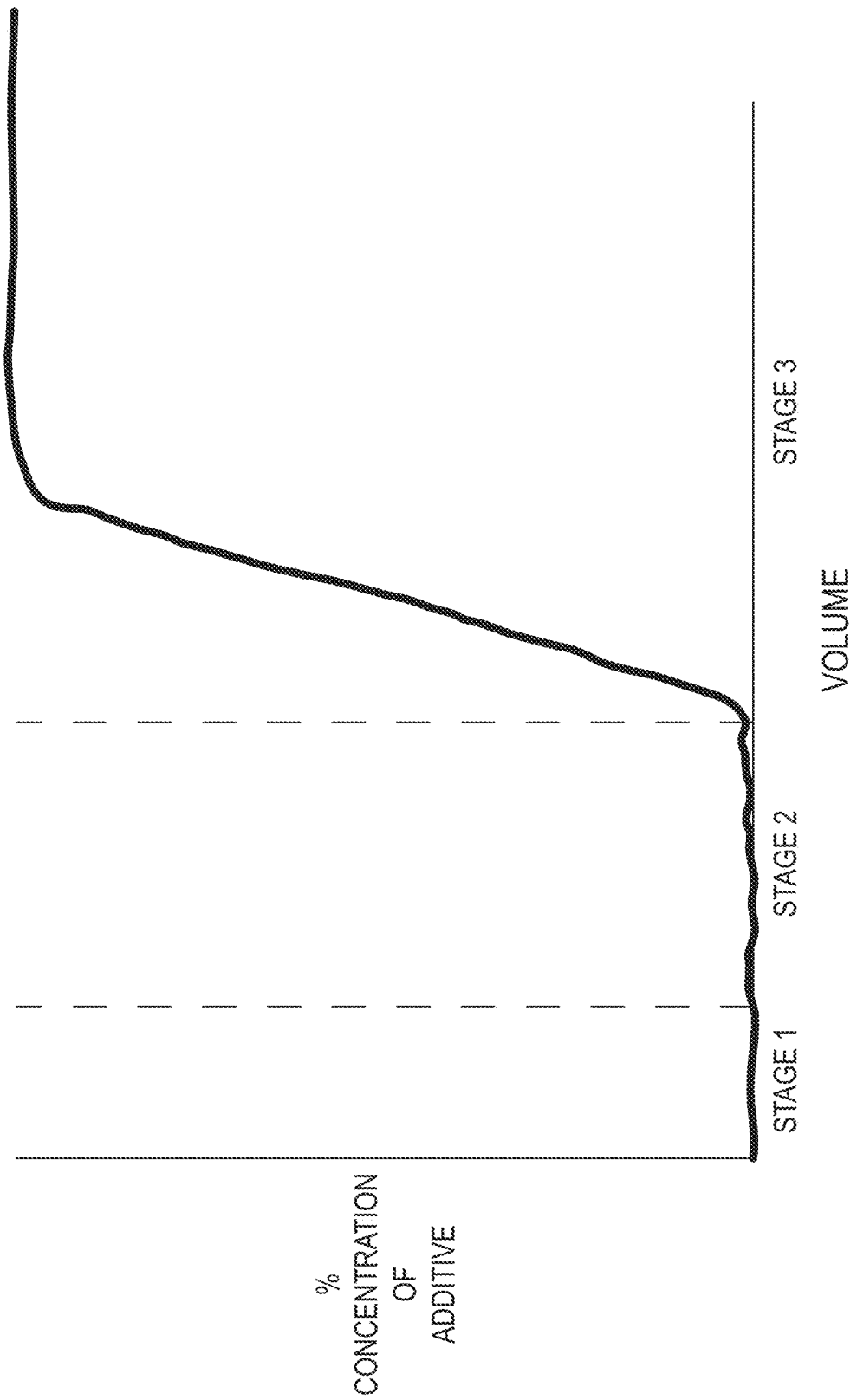
FIG. 15 is a graph showing an example of an infusion of liquid through a connector of FIG. 2C, that illustrates a relationship between the concentration of additive as compared to infused volume.

FIGS. 14 and 15 provide examples of liquid dispensing profiles created by liquid flowing through and/or out of a fluid source, such as connector 200 (or connector 200C, 200D) and connector 200B, respectively. In the first stage, which in some embodiments can correspond to the condition of the connector 200, 200B shown in FIGS. 6A and 10, medical fluid 266, 266B can pass into and out of the connector 200, 200B in an unchanged or essentially unchanged state such that the concentration of additive 112 is essentially non-existent or essentially zero or clinically insignificant. In the second stage, which in some embodiments can correspond to the condition of the connector 200, 200B shown in FIGS. 7-8 and 11-12, medical fluid 266, 266B can pass into and out of the connector with very little, if any change (e.g., not clinically significant), but some of the medical fluid can be internally mixing with additive 112 and can be temporarily retained or stored inside of the connector 200, 200B. In the second stage, medical fluid 266, 266B can also pass into and out of the connector in an unchanged or essentially unchanged state. Finally, in the third stage, which in some embodiments can correspond to the condition of the connector 200, 200B shown in FIGS. 9 and 13, medical fluid 266, 266B can stop being infused into the connector 200, 200B, and/or therapeutic fluid 278, 278B can be expelled or dispensed or emitted from a liquid storage or liquid retaining region inside of the connector 200, 200B with a high concentration of additive 112 in the therapeutic fluid 278, 278B, which is clinically significant (e.g., for an antimicrobial product, the concentration of antimicrobial additive can be sufficient to provide antimicrobial protection in a catheter that diminishes the risk of microbial invasion into the catheter to a level that is clinically acceptable according to one or more applicable industry standard practices or guidelines). For example, during the third or final stage, in some embodiments, the maximum concentration of additive can be at least about 3% or at least about 10% or at least about 30% of the total liquid volume or weight, and/or no more than about 5% or no more than about 12% or no more than about 40% of the total liquid volume or weight, depending upon the particular type of additive used and the therapeutic purposes of the treatment. As illustrated in FIGS. 14 and 15, the concentration of the additive can rapidly increase from essentially none (or a clinically insignificant amount) to any of the foregoing clinically significant concentrations (or any other clinically significant concentration) in a short time or while a small amount of liquid passes through the connector, such as within less than or equal to about 0.25 second or less than or equal to about 1.0 second at an average fluid flow rate through a medical connector, or while less than or equal to about 1, 2, or 5 mL of liquid passes through the connector. In some embodiments, the percentage of concentration of additive, such as an antimicrobial additive and/or an antibiotic additive, can rise from essentially zero in the first stage to at least about 0.2% or at least about 1.5% in a subsequent stage (e.g., the third stage). Many other different types and stages and concentrations of fluid-dispensing profiles can be provided, depending upon therapeutic needs. In some embodiments, the volume of liquid that is dispensed or expelled out of the connector during the first stage and/or the second stage (or any other initial or intermediate stage) can be greater than or equal to about the volume of liquid capacity of a catheter to which the connector is intended to be attached, such that the liquid dispensed or expelled out of the connector during the first stage and/or the second stage can provide a flush of basic, standard, non-therapeutic, non-pharmaceutical, or inert medical liquid (such as medical liquid without an additive, e.g. saline or other medical liquid without an additive) from the connector into the patient catheter to flush essentially the entire patient catheter before subsequent use. In some embodiments, the volume of liquid that is dispensed or expelled out of the connector during the third stage (or during any other intermediate or final stage or any stage that is subsequent to the first stage or to the second stage) can be less than or equal to about the volume of liquid capacity of the patient catheter to which the connector is intended to be attached, such that the liquid dispensed or expelled out of the connector during this stage does not become infused into the patient or does not become infused into the patient in any clinically significant volume, but rather is configured to remain in the catheter during a locking or antimicrobial phase. Many other different configurations can be used, including configurations that do not provide a locking or antimicrobial phase. The volumes in each stage can be designed or configured to fit a variety of different clinical needs or therapeutic purposes.

Some embodiments pertain to methods of using medical fluid connectors as disclosed herein. Any device or structure illustrated or described in this specification can be used with any method in this specification. In some embodiments, a method includes the step of obtaining a connector. In some embodiments, a method includes the step of attaching the connector to a catheter. In some embodiments, a method includes the step of obtaining a syringe or device capable of holding a medical fluid. In some embodiments, a method includes the step of attaching the syringe or other device to the connector. In some embodiments, a method includes the step of introducing medical fluid into the connector and/or the catheter using the syringe or other medical fluid carrying device. In some embodiments, a method includes the step of introducing an additive to the fluid as it passes through the connector. In some embodiments, a first portion of fluid that is substantially additive-free is introduced to the catheter. In some embodiments, a second portion of fluid that contains additive is introduced to the catheter. In some embodiments, a first portion of fluid that contains additive (e.g., a therapeutic) is introduced to the catheter and/or passed through the catheter to the patient. In some embodiments, a second portion of fluid that is contains additive is introduced to the catheter. In some embodiments, the method includes the step of locking the catheter with an antimicrobial-containing medical fluid.

Some embodiments pertain to methods of preparing medical fluid connectors. In some embodiments, a method includes the step of obtaining one or more of a fluid guide, a proximal cover region (e.g., with a vent), and/or a distal fluid port. In some embodiments, a method includes the step of attaching a fluid modifier in place at a plurality of points or regions inside of the connector. In some embodiments, a method includes the step of affixing a proximal edge of the flexible carrier securely between an upper region (e.g., forming a lip, a projection, a barb, etc.) of the housing and an underside of the outer edge of a region of the fluid guide (e.g., a cover region). In some embodiments, a distal end region of the flexible carrier is fastened circumferentially (e.g., securely and/or in a fluid-tight manner) at the distal attachment region of the fluid guide, such as by affixing a distal opening in the flexible carrier that is slightly smaller than the outer circumference of the distal attachment region, causing the distal opening to exert a radially inwardly directed restoring force which tightly grips the distal attachment region of the fluid guide. In some embodiments, the fluid guide and/or the flexible carrier can be placed into the housing of the connector. In some embodiments, a cap can be placed over the fluid guide, securing it in place. In some embodiments, a first fluid line attachment can be affixed or placed on the fluid guide.

Certain features that are described in this disclosure in the context of separate implementations can also be implemented in combination in a single implementation. Conversely, various features that are described in the context of a single implementation also can be implemented in multiple implementations separately or in any suitable subcombination. Moreover, although features may be described above as acting in certain combinations, one or more features from a claimed combination can in some cases be excised from the combination, and the combination may be claimed as a subcombination or variation of a sub combination.

Any portion of any of the steps, processes, structures, and/or devices disclosed or illustrated in one embodiment, flowchart, or example in this disclosure can be combined or used with (or instead of) any other portion of any of the steps, processes, structures, and/or devices disclosed or illustrated in a different embodiment, flowchart, or example. The embodiments and examples described herein are not intended to be discrete and separate from each other. Combinations, variations, and other implementations of the disclosed features are within the scope of this disclosure.

Some embodiments have been described in connection with the accompanying drawings. Moreover, while operations may be depicted in the drawings or described in the specification in a particular order, such operations need not be performed in the particular order shown or in sequential order, and/or one or more of the operations may be omitted entirely, to achieve desirable results. Other operations that are not depicted or described can be incorporated in the example methods and processes. For example, one or more additional operations can be performed before, after, simultaneously, or between any of the described operations. Additionally, the operations may be rearranged or reordered in other implementations. Also, the separation of various components in the implementations described above should not be understood as requiring such separation in all implementations, and it should be understood that the described components and systems can generally be integrated together in a single product or packaged into multiple products. Additionally, other implementations are within the scope of this disclosure.

The following is claimed:

1. A medical fluid-modifying device configured to modify a medical fluid by inserting an additive into the medical fluid, the medical fluid-modifying device comprising:
    an upstream connector;
    a downstream connector;
    a main fluid pathway; and
    a secondary fluid pathway that is different from the main fluid pathway, the secondary fluid pathway including a carrier of additive, the carrier of additive being flexible, wherein at a diversion region between the main fluid pathway and the secondary fluid pathway, the main fluid pathway stays open to a flow of the medical fluid;
    wherein the main fluid pathway is configured to convey unchanged a portion of the medical fluid that is inserted into the fluid-modifying device from the upstream connector to the downstream connector,
    wherein the secondary fluid pathway is configured to add an additive into a portion of the medical fluid that is inserted into the fluid-modifying device, and
    wherein the unchanged portion of the medical fluid is configured to be conveyed through the medical fluid-modifying device before the portion of the medical fluid in which the additive is added.

2. The medical fluid-modifying device of claim 1, wherein the unchanged portion of the medical fluid is configured to have a sufficient volume to flush out a patient catheter to be used with the medical fluid-modifying device before a clinically significant amount of additive is added to the medical fluid by the medical fluid-modifying device.

3. The combination of the medical fluid-modifying device of claim 2 and the patient catheter.

4. The fluid-modifying device of claim 1, wherein the flexible carrier of additive is configured to change the volume within the secondary fluid pathway.

5. The medical fluid-modifying device of claim 1, wherein at the diversion region between the main fluid pathway and the secondary fluid pathway, the main fluid pathway has a first cross-sectional area and the secondary fluid pathway has a second cross-sectional area, the first cross-sectional area being greater than the second cross-sectional area.

6. The medical fluid-modifying device of claim 5, wherein the first cross-sectional area is at least about four times larger than the second cross-sectional area.

7. A medical fluid connector configured to receive and dispense medical fluid, the medical fluid connector comprising:
    an initial stage in which the connector is configured to permit at least a portion of a medical fluid that is infused into the connector to be dispensed out of the connector essentially unchanged; and
    a subsequent stage in which the connector is configured to dispense a therapeutic liquid out of the connector after infusion of the medical fluid into the connector has stopped such that the therapeutic liquid comprises a portion of the medical fluid that was infused into the connector in the initial stage plus a therapeutic additive;
    wherein the connector is configured to automatically transition from the initial stage to the subsequent stage initiated by stopping of infusion of the medical fluid into the connector.

8. The medical fluid connector of claim 7 comprising a fluid modifier.

9. The medical fluid connector of claim 8 in which the fluid modifier is a flexible carrier.

10. The medical fluid connector of claim 9 in which the flexible carrier comprises one or more additives.

11. The medical fluid connector of claim 10 in which the one or more additives comprise an antimicrobial agent.

12. The medical fluid connector of claim 11 in which the antimicrobial agent is chlorhexidine.

13. A medical fluid connector configured to receive and dispense medical fluid, the medical fluid connector comprising:
    an inlet configured to receive into the connector a volume of a medical fluid; and
    an outlet configured to dispense a volume of the medical fluid out of the connector in at least a first stage and a second stage, the medical fluid connector being configured to move at least a portion of the medical fluid through the connector along a different fluid path in the second stage than in the first stage, wherein in the first stage, the connector is configured to dispense the medical fluid out of the connector without a therapeutic additive or at least without a clinically significant concentration of the therapeutic additive; and wherein in the second stage, the connector is configured to dispense the medical fluid out of the connector with a therapeutic additive of a clinically significant concentration, and wherein the connector is configured to automatically increase the concentration of additive in the dispensed medical fluid within the second stage initiated by stopping the flowing of the medical fluid into the inlet of the connector.

14. The medical fluid connector of claim 13, wherein the medical fluid connector is configured to dispense the medical fluid during the second stage even after the medical fluid is no longer being received into the connector.

15. A medical fluid-modifying device configured to modify a medical fluid by inserting an additive into the medical fluid, the medical fluid-modifying device comprising:
an upstream connector;
a downstream connector;
a main fluid pathway; and
a secondary fluid pathway that is different from the main fluid pathway, wherein at a diversion region between the main fluid pathway and the secondary fluid pathway, the main fluid pathway stays open to a flow of the medical fluid, and wherein at the diversion region between the main fluid pathway and the secondary fluid pathway, the main fluid pathway has a first cross-sectional area and the secondary fluid pathway has a second cross-sectional area, the first cross-sectional area being at least about four times larger than the second cross-sectional area;

wherein the main fluid pathway is configured to convey unchanged a portion of the medical fluid that is inserted into the fluid-modifying device from the upstream connector to the downstream connector, and wherein the secondary fluid pathway is configured to add an additive into a portion of the medical fluid that is inserted into the fluid-modifying device.

16. The medical fluid-modifying device of claim 15, wherein the unchanged portion of the medical fluid is configured to be conveyed through the medical fluid-modifying device before the portion of the medical fluid in which the additive is added.

17. The medical fluid-modifying device of claim 15, wherein the unchanged portion of the medical fluid is configured to have a sufficient volume to flush out a patient catheter to be used with the medical fluid-modifying device before a clinically significant amount of additive is added to the medical fluid by the medical fluid-modifying device.

18. The combination of the medical fluid-modifying device of claim 17 and the patient catheter.

19. The fluid-modifying device of claim 16, wherein the secondary fluid pathway includes a carrier of additive.

20. The fluid-modifying device of claim 19, wherein the carrier of additive is configured to change the volume within the secondary fluid pathway.

* * * * *